US005604224A

United States Patent [19]

Dority, Jr. et al.

[11] Patent Number: 5,604,224

[45] Date of Patent: Feb. 18, 1997

[54] SUBSTITUTED HETEROCYCLYLISOQUINOLINIUM SALTS AND COMPOSITIONS AND METHODS OF USE THEREOF

[75] Inventors: John A. Dority, Jr., Upper Providence Township; William G. Earley, East Vincent Township; Virendra Kumar, Tredyffrin Township; John P. Mallamo, Uwchlan Township; Matthew S. Miller, Lower Makefield Township; Chakrapani Subramanyam, Towamencin Township, all of Pa.

[73] Assignee: Sterling Winthrop Inc., New York, N.Y.

[21] Appl. No.: 452,941

[22] Filed: May 30, 1995

Related U.S. Application Data

[60] Division of Ser. No. 283,319, Jul. 29, 1994, which is a continuation-in-part of Ser. No. 121,389, Sep. 14, 1993, abandoned.

[51] Int. Cl.$^6$ .......................... A61K 31/54; A01N 43/66; A01N 43/78; A01N 43/40

[52] U.S. Cl. .................................... 514/726.8; 514/727.2; 514/228.5; 514/228.8; 514/241; 514/245; 514/246; 514/750; 514/254; 514/255; 514/257; 514/258; 514/277; 514/278; 514/289; 514/299; 514/300; 514/307; 514/308; 514/311; 514/318; 514/321; 514/322; 514/338; 514/339; 514/361; 514/363; 514/364; 514/366; 514/373; 514/375; 514/379; 514/383; 514/393; 514/403

[58] Field of Search .............................. 514/226.8, 227.2, 514/228.5, 228.8, 241, 245, 246, 250, 254, 255, 257, 258, 277, 278, 289, 299, 300, 307, 308, 311, 318, 321, 322, 338, 339, 361, 363, 364, 366, 373, 375, 379, 383, 393, 403

[56] References Cited

U.S. PATENT DOCUMENTS 5,180,831 1/1993 Powers et al. .......................... 546/291

OTHER PUBLICATIONS

Bradsher et al, J. Het. Chem. 1972, 9(2) 177–181.

*Primary Examiner*—C. Warren Ivy
*Assistant Examiner*—Raymond Covington
*Attorney, Agent, or Firm*—Paul E. Dupont; William J. Davis

[57] ABSTRACT

Substitutued heterocyclylisoquinolinium salts, pharmaceutical compositions containing them and methods for the treatment or prevention of neurodegenerative disorders or neurotoxic injuries utilizing them.

21 Claims, No Drawings

SUBSTITUTED HETEROCYCLYLISOQUINOLINIUM SALTS AND COMPOSITIONS AND METHODS OF USE THEREOF

CROSS REFERENCE TO RELATED APPLICATIONS

This application is a division of application Ser. No. 08/283,319 filed Jul. 29, 1994 pending, which in turn is a continuation-in-part of our prior application Ser. No. 08/121,389, filed Sep. 14, 1993 now abandoned

BACKGROUND OF THE INVENTION (a) Field of the Invention

The invention relates to substituted heterocyclylisoquinolinium salts, to compositions containing the same and to the method of use thereof in the treatment or prevention of neurodegenerative disorders or neurotoxic injuries.

(b) Information Disclosure Statement

Bradsher et al., J Het. Chem. 1972, 9(2), 177–181, disclose 5,10,12,13-tetrahydro-1,2-diphenyl-11H-5,10-endocyclopent-1H-imidazo[1,2-b]isoquinolin-4-ium bromide, 11-carbazol-9-yl-5,10-dihydro-1-(3-trifluoromethylphenyl)-2-phenyl-5,10-ethano-1H-imidazo[1,2-b]isoquinolin-4-ium bromide, and 12-(2-pyrrolidinone-1-yl)-6,11-ethano-6,11-dihydro-3-phenylpyrazino[1,2-b]isoquinolin-5-ium bromide; as well as a series of Diels-Alder adducts prepared from 3-R-pyrazino[1,2-b]isoquinolin-5-ium 2-oxide perchlorates (R=H,$CH_3$, Ph) and cyclopentadiene, N-vinyl-2-pyrrolidinone, 9-vinylcarbazole and ethylvinyl ether. No utility is disclosed for these compounds.

SUMMARY OF THE INVENTION

The invention relates to compounds of the Formula I:

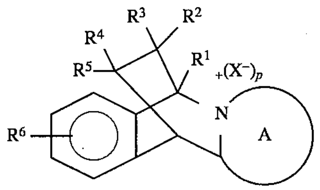

I wherein:

$R^1$ is hydrogen, or lower-alkyl;

$R^2$ and $R^3$ are independently hydrogen, or lower-alkyl; or $R^2$ and $R^3$ together form a cycloalkyl ring, or a lower-alkylidene group;

$R^4$ and $R^5$ are independently lower-alkynyl, lower-alkoxy, phenyl (or phenyl substituted by lower-alkoxy, halogen, lower-alkyl, polyfluorolower-alkyl, polychlorolower-alkyl, or hydroxy), a 5- or 6-membered monocyclic aromatic heterocyclic ring system containing from one to three, the same or different, heteroatoms selected from the group consisting of nitrogen, oxygen and sulfur (or said 5- or 6-membered monocyclic aromatic heterocyclic ring system substituted on any available carbon atom thereof by hydroxy, lower-alkyl, oxo, nitro, halogen, or lower-alkoxy; or on any available nitrogen atom thereof by lower-alkyl, tri-lower-alkylsilyl, trilower-alkylsilyl-lower-alkoxy-lower-alkyl, or phenyl-lower-alkyl (or said phenyl-lower-alkyl group substituted on the phenyl group by lower-alkoxy, lower-alkyl or halogen)); a 9- or 10-membered bicyclic aromatic heterocyclic ring system containing from one to two, the same or different, heteroatoms selected from the group consisting of oxygen, nitrogen and sulfur (or said 9- or 10-membered bicyclic aromatic heterocyclic ring system substituted at any available carbon atom thereof by hydroxy, lower-alkyl, oxo, nitro, halogen, or lower-alkoxy; or on any available nitrogen atom thereof by lower-alkyl, trilower-alkylsilyl, trilower-alkylsilyl-lower-alkoxy-lower-alkyl, or phenyl-lower-alkyl (or said phenyl-lower-alkyl group substituted on the phenyl group by lower-alkoxy, lower-alkyl, or halogen)); or a 5- or 6-membered monocyclic nonaromatic heterocyclic ring system containing from one to two, the same or different, heteroatoms selected from the group consisting of nitrogen, oxygen and sulfur (or said 5- or 6-membered nonaromatic heterocyclic ring system substituted on any available carbon atom thereof by hydroxy, lower-alkyl, oxo, nitro, halogen, or lower-alkoxy, or on any available nitrogen atom thereof by lower-alkyl, trilower-alkylsilyl, trilower-alkylsilyl-lower-alkoxy-lower-alkyl, or phenyl-lower-alkyl (or said pheny-lower-alkyl group substituted on the phenyl group by lower-alkoxy, lower-alkyl or halogen));

or $R^2$ and $R^4$ and/or $R^3$ and $R^5$ taken together with the carbon atoms to which they are attached form a bicyclic ring system of the formula

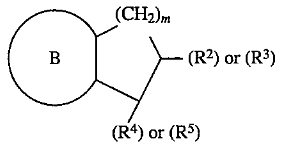

wherein B is: phenyl, or a 5- or 6-membered monocyclic aromatic heterocyclic ring system containing from one to three, the same or different, heteroatoms selected from the group consisting of nitrogen, oxygen and sulfur, (or said B ring substituted on any available carbon atom thereof by lower-alkoxy, or lower-alkyl), and n is an integer from one to three;

$R^6$ is hydrogen, or from one to four, the same or different, substituents in any of the 7-, 8-, 9-, or 10-positions (if A is a six-membered ring), or in any of the 6-, 7-, 8-, or 9-position (if A is a five-membered ring) selected from the group consisting of lower-alkyl, lower-alkanoyloxy, halogen, nitro, hydroxy, lower-alkoxy, methylenedioxy, polychlorolower-alkyl, $OCO(CH_2)_m$, C(O)O alkyl, OC(O)alkyl, C(O)Oalkyl, $CO_2^-$, carboxy, sulfo, $SO_3^-$, $PO_3H$, $PO_3^-$, cyano, polyfluorolower-alkyl, OC(O) alkyl-CH=CH-alkyl, OC(O)-lower-alkenyl-C(O)alkyl, alkoxy, OC(O)alkylC(O)Oalkyl, amino, and lower-alkylsulfonylamino, wherein m is an integer from one to four;

A together with the carbon and nitrogen atoms to which it is attached forms a 5- or 6-membered monocyclic aromatic heterocycle containing from two to three, the same or different, heteroatoms selected from the group consisting of nitrogen, oxygen and sulfur (or said 5- or 6-membered monocyclic aromatic heterocycle substituted on any available carbon atom thereof by hydroxy, OC(O)alkyl-CH=CH-alkyl, OC(O)alkyl, OC(O)lower-alkenyl-C(O)Oalkyl, alkoxy, OC(O)alkylC(O)Oalkyl, nitro, amino, lower-alkylsulfonylamino, lower-alkyl, lower-alkoxy, or halogen; or on any available nitrogen atom thereof by phenyl (or said phenyl group substituted by lower-alkoxy, lower-alkyl or halogen), diphenylmethyl, naphthyl-lower-alkyl (or said naphthyl-lower-alkyl group substituted on the naphthyl group by lower-alkoxy, lower-alkyl or halogen), lower-alkyl, or phenyl-lower-alkyl (or said phenyl-lower-alkyl group substituted on the phenyl group by lower-alkoxy, lower-alkyl or halogen));

$X^-$ is an anion; and p is zero when $R^6$ is a negatively charged radical, and p is one when $R^6$ is other than a negatively charged radical; or a pharmaceutically acceptable acid-addition salt of basic members thereof; or a hydrate thereof; or a stereoisomer thereof.

The compounds of Formula I bind to the PCP receptor and are thus useful in the treatment or prevention of neurodegenerative disorders or neurotoxic injuries.

Compounds within the ambit of Formula I above are those wherein:

$R^1$ is hydrogen, or lower-alkyl;

$R^2$ and $R^3$ are independently hydrogen, or lower-alkyl; or $R^2$ and $R^3$ together form a cycloalkyl ring, or a lower-alkylidene group;

$R^4$ and $R^5$ are independently lower-alkynyl, lower-alkoxy, phenyl (or phenyl substituted by lower-alkoxy, halogen, lower-alkyl, polyfluorolower-alkyl, polychlorolower-alkyl, or hydroxy), a 5- or 6-membered monocyclic aromatic heterocyclic ring system containing from one to three, the same or different, heteroatoms selected from the group consisting of nitrogen, oxygen and sulfur (or said 5- or 6-membered monocyclic aromatic heterocyclic ring system substituted on any available carbon atom thereof by lower-alkyl, oxo, nitro, halogen, or lower-alkoxy; or on any available nitrogen atom thereof by lower-alkyl, tri-lower-alkylsilyl, trilower-alkylsilyl-lower-alkoxy-lower-alkyl, or phenyl-lower-alkyl (or said phenyl-lower-alkyl group substituted on the phenyl group by lower-alkoxy, lower-alkyl or halogen)); a 9- or 10-membered bicyclic aromatic heterocyclic ring system containing from one to two, the same or different, heteroatoms selected from the group consisting of oxygen, nitrogen and sulfur (or said 9- or 10-membered bicyclic aromatic heterocyclic ring system substituted at any available carbon atom thereof by lower-alkyl, oxo, nitro, halogen, or lower-alkoxy; or on any available nitrogen atom thereof by lower-alkyl, trilower-alkylsilyl, trilower-alkylsilyl-lower-alkoxy-lower-alkyl, or phenyl-lower-alkyl (or said phenyl-lower-alkyl group substituted on the phenyl group by lower-alkoxy, lower-alkyl, or halogen)); or a 5- or 6-membered monocyclic nonaromatic heterocyclic ring system containing from one to two, the same or different, heteroatoms selected from the group consisting of nitrogen, oxygen and sulfur (or said 5- or 6-membered nonaromatic heterocyclic ring system substituted on any available carbon atom thereof by lower-alkyl, oxo, nitro, halogen, or lower-alkoxy, or on any available nitrogen atom thereof by lower-alkyl, trilower-alkylsilyl, trilower-alkylsilyl-lower-alkoxy-lower-alkyl, or phenyl-lower-alkyl (or said pheny-lower-alkyl group substituted on the phenyl group by lower-alkoxy, lower-alkyl or halogen));

or $R^2$ and $R^4$ and/or $R^3$ and $R^5$ taken together with the carbon atoms to which they are attached form a bicyclic ring system of the formula

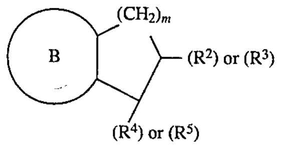

wherein B is: phenyl, or a 5- or 6-membered monocyclic aromatic heterocyclic ring system containing from one to three, the same or different, heteroatoms selected from the group consisting of nitrogen, oxygen and sulfur, (or said B ring substituted on any available carbon atom thereof by lower-alkoxy, or lower-alkyl), and n is an integer from one to three;

$R^6$ is hydrogen, or from one to four, the same or different, substituents in any of the 7-, 8-, 9-, or 10-positions (if A is a six-membered ring), or in any of the 6-, 7-, 8-, or 9-position (if A is a five-membered ring) selected from the group consisting of lower-alkyl, lower-alkanoyloxy, halogen, nitro, hydroxy, lower-alkoxy, methylenedioxy, polychlorolower-alkyl, $OCO(CH_2)_m$ C(O)Oalkyl, OC(O)alkyl, C(O)Oalkyl, $CO_2^-$, carboxy, sulfo, $SO_3^-$, $PO_3H$, $PO_3^-$, cyano, and polyfluorolower-alkyl, wherein m is an integer from one to four;

A together with the carbon and nitrogen atoms to which it is attached forms a 5- or 6-membered monocyclic aromatic heterocycle containing from two to three, the same or different, heteroatoms selected from the group consisting of nitrogen, oxygen and sulfur (or said 5- or 6-membered monocyclic aromatic heterocycle substituted on any available carbon atom thereof by lower-alkyl, lower-alkoxy, or halogen; or on any available nitrogen atom thereof by lower-alkyl, or phenyl-lower-alkyl (or said phenyl-lower-alkyl group substituted on the phenyl group by lower-alkoxy, lower-alkyl or halogen));

$X^-$ is an anion; and p is zero when $R^6$ is a negatively charged radical, and p is one when $R^6$ is other than a negatively changed radical; or a pharmaceutically acceptable acid-addition salt of basic members thereof; or a hydrate thereof; or a stereoisomer thereof.

Preferred compounds of Formula I above are those wherein:

$R^1$ is hydrogen; or lower-alkyl;

$R^2$ and $R^3$ are independently hydrogen, or lower-alkyl;

$R^4$ and $R^5$ are independently lower-alkoxy, phenyl (or phenyl substituted by lower-alkoxy, halogen, lower-alkyl, polyfluorolower-alkyl, polychlorolower-alkyl, or hydroxy), or a 5-membered monocyclic aromatic heterocyclic ring system containing from one to three, the same or different, heteroatoms selected from the group consisting of nitrogen, oxygen, and sulfur (or said 5-membered monocyclic aromatic heterocyclic ring system substituted on any available carbon atom thereof by lower-alkyl, oxo, or lower-alkoxy; or on any available nitrogen atom thereof by lower-alkyl, or phenyl-lower-alkyl (or said phenyl-lower-alkyl group substituted on the phenyl group by lower-alkoxy, lower-alkyl or halogen); and $R^6$ is hydrogen, or one substituent in any of the 6-,7-,8- or 9-positions selected from the group consisting of lower-alkyl, halogen, hydroxy, and lower-alkoxy;

A together with the carbon and nitrogen atoms to which it is attached forms a 5-membered monocyclic aromatic heterocycle containing from two to three, the same or different, heteroatoms selected from the group consisting of nitrogen, oxygen and sulfur (or said 5-membered monocyclic aromatic heterocycle substituted on any available carbon atom thereof by lower-alkyl, lower-alkoxy, or halogen; or on any availabe nitrogen atom thereof by lower-alkyl, or phenyl-lower-alkyl (or said phenyl-lower-alkyl group substituted on the phenyl group by lower-alkoxy, lower alkyl or halogen); and $X^-$ is an anion; or a pharmaceutically acceptable acid-addition salt of basic members thereof; or a hydrate thereof; or a stereoisomer thereof.

Particularly preferred compounds of the Formula I above are those wherein:

$R^1$ is hydrogen;

$R^2$ and $R^3$ are independently hydrogen, or lower-alkyl;

$R^4$ and $R^5$ are independently lower-alkoxy, phenyl, or a 5-membered monocyclic aromatic heterocyclic ring system containing from one to two, the same or different, heteroatoms selected from the group consisting of nitrogen and oxygen (or said 5-membered monocyclic aromatic heterocyclic ring system substituted on any available carbon atom thereof by oxo, or on any available nitrogen atom thereof by phenyl-lower-alkyl (or said phenyl-lower-alkyl group substituted on the phenyl group by lower-alkoxy);

$R^6$ is hydrogen, or one lower-alkoxy substituent in any of the 6-, 7-,8- or 9-positions;

A together with the carbon and nitrogen atoms to which it is attached forms a 5-membered monocyclic aromatic heterocycle containing from two to three, the same or different, heteroatoms selected from the group consisting of nitrogen and sulfur (or said 5-membered monocyclic aromatic heterocycle substituted on any available carbon atom thereof by lower-alkyl; or on any available nitrogen atom thereof by lower-alkyl, or phenyl-lower-alkyl (or said phenyl-lower-alkyl group substituted on the phenyl group by lower alkoxy); and $X^-$ is an anion; or a pharmaceutically acceptable acid-addition salt of basic members thereof; or a hydrate thereof; or a stereoisomer thereof.

Other compounds of the Formula I above are those wherein $R^6$ is from one to four, the same or different, substituents in any of the 7-, 8-, 9-, or 10-positions (if A is a six-membered ring), or in any of the 6-, 7-, 8-, or 9-positions (if A is a five-membered ring) selected from the group consisting of OC(O)alkyl-CH═CH-alkyl, OC(O)-lower-alkenyl-C(O)Oalkyl, alkoxy, OC(O)alkylC(O)Oalkyl, amino and lower-alkylsulfonylamino; and $R^1$, $R^2$, $R^3$, $R^4$, $R^5$, A and $X^-$ are as defined hereinabove on pages 2 to 4.

Still other compounds of the Formula I above are those wherein A together with the carbon and nitrogen atoms to which it is attached forms a 5- or 6-membered monocyclic aromatic heterocycle containing from two to three, the same or different, heteroatoms selected from the group consisting of nitrogen, oxygen and sulfur with said 5- or 6-membered monocyclic aromatic heterocycle being substituted on any available carbon atom thereof by hydroxy, OC(O)alkyl-CH═CH-alkyl, OC(O)alkyl, OC(O)-lower-alkenyl-C(O)Oalkyl, alkoxy, OC(O)alkylC(O)Oalkyl, nitro, amino, or lower-alkylsulfonylamino; or on any available nitrogen atom thereof by phenyl (or said phenyl group substituted by lower-alkoxy, lower-alkyl or halogen), diphenylmethyl, or naphthyl-lower-alkyl (or said naphthyl-lower-alkyl group substituted on the naphthyl group by lower-alkoxy, lower-alkyl, or halogen), and $R^1$, $R^2$, $R^3$, $R^4$, $R^5$, $R^6$ and $X^-$ are as defined hereinabove on pages 2 to 4.

Preferred compounds of the Formula I within this latter group are those wherein:

$R^1$, $R^2$ and $R^3$ are as defined hereinabove on page 2;

$R^4$ and $R^5$ are independently a 5- or 6-membered monocyclic aromatic heterocyclic ring system selected from the group consisting of furanyl, thienyl, oxazolyl, thiazolyl, pyrazolyl, triazolyl, pyrrolyl, imidazolyl, isoxazolyl, oxadiazolyl, and thiadiazolyl;

$R^6$ is hydrogen, or one substituent in any of the 6-, 7-, 8- or 9-positions selected from the group consisting of lower-alkoxy and hydroxy;

A together with the carbon and nitrogen atoms to which it is attached forms a 5-membered monocyclic aromatic heterocycle selected from the group consisting of imidazolyl and triazolyl, with said 5-membered monocyclic aromatic heterocycle being substituted on any available nitrogen atom thereof by phenyl, diphenylmethyl, or naphthyl-lower-alkyl; and $X^-$ is an anion.

The invention further relates to pharmaceutical compositions which comprise a compound of the Formula I above together with a pharmaceutically acceptable carrier, adjuvant, diluent, or vehicle.

The invention further relates to a method for the treatment or prevention of neurodegenerative disorders, or neurotoxic injuries which comprises administering to a patient in need of such treatment an effective amount of a compound of the Formula I above.

DETAILED DESCRIPTION INCLUSIVE OF PREFERRED EMBODIMENTS

The term lower-alkyl as used herein means linear or branched hydrocarbon chains having one to about four carbon atoms and thus includes methyl, ethyl, propyl, isopropyl, n-butyl, sec-butyl, and the like.

The term lower-alkoxy as used herein means linear or branched alkyloxy substituents having one to about four carbon atoms and thus includes methoxy, ethoxy, propoxy, isopropoxy, butoxy, sec-butoxy, and the like.

The term alkyl as used herein means linear or branched hydrocarbon chains having one to about sixteen carbon atoms and thus includes methyl, ethyl, 1,1-dimethylethyl propyl, isopropyl, n-butyl, sec-butyl, t-butyl, n-pentyl, 2-methyl-3-butyl, 1-methylbutyl, 2-methylbutyl, neopentyl, n-hexyl, 1-methylpentyl, 3-methylpentyl, 1-ethylbutyl, 2-ethylbutyl, 2-hexyl, 3-hexyl, n-heptyl, 2-heptyl, n-octyl, 2,4,4-trimethylpentyl, n-nonyl, 3,5,5-trimethylhexyl, n-decyl, 3,7-dimethyloctyl, n-undecyl, n-dodecyl, n-tridecyl, n-tetradecyl, n-pentadecyl, n-hexadecyl, and the like.

The term alkoxy as used herein means linear or branched alkyloxy substituents having from one to about sixteen carbon atoms and thus includes methoxy, ethoxy, propoxy, isopropoxy, butoxy, sec-butoxy, t-butoxy, n-pentyloxy, 2-methyl-3-butyloxy, 1-methylbutytoxy, 2-methylbutyloxy, neopentyloxy, n-hexyloxy, 1-methylpentyloxy, 3-methylpentyloxy, 1-ethylbutyloxy, 2-ethylbutyloxy, 2-hexyloxy, 3-hexyloxy, n-heptyloxy, 2-heptyloxy, n-octyloxy, 2,4,4-trimethylpentyloxy, n-nonyloxy, 3,5,5-trimethylhexyloxy, n-decyloxy, 3,7-dimethyloctyloxy, n-undecyloxy, n-dodecyloxy, n-tridecyloxy, n-tetradecyloxy, n-pentadecyloxy, n-hexadecyloxy, and the like.

The term halogen or halide as used herein means bromine, chlorine, iodine, or fluorine.

The term lower-alkanoyloxy as used herein means linear or branched hydrocarbon chains having two to about four carbon atoms and thus includes acetyloxy, propionyloxy, isobutyryloxy, and the like.

The term cycloalkyl as used herein means $C_3$ to $C_7$ unsaturated monocylic hydrocarbon residues and thus includes cyclopropyl, cyclobutyl, cyclopentyl, cyclohexyl and cycloheptyl.

The term lower-alkylidene as used herein means linear or branched hydrocarbon chains having one to about four carbon atoms and thus includes methylidene, ethylidene, propylidene, isopropylidene, sec-butylidene, and the like.

The term lower-alkenyl as used herein means linear or branched unsaturated hydrocarbon radicals having two to about four carbon atoms and thus includes ethenyl, 1-propenyl, 2-propenyl, isopropenyl, 1-methyl-2-propenyl, 2-butenyl, isobutenyl and the like.

The term lower-alkynyl as used herein means linear or branched unsaturated radicals having two to about four carbon atoms and thus includes ethynyl, 1-propynyl, 2-propynyl, 1-methyl-2-propynyl, 2-butynyl and the like.

The term anion ($X^-$) as used herein means the anion of an organic acid (includes anions of organic monoacids, as well as monoanions of organic diacids) which is at least as strong as acetic acid, and thus includes anions of such acids as acetic acid, methanesulfonic acid, toluensulfonic acid, trifluoromethanesulfonic acid, (−)-dibenzoyl-L-tartaric acid [(−)-DBT], (+)dibenzoyl-D-tartaric acid [(+)-DBT], and the like; or it means an inorganic acid anion such as chloride, bromide, perchlorate, $PF_6^-$ and the like, preferably chloride.

The term 5- or 6-membered monocyclic aromatic heterocyclic ring system as used herein means 5- or 6-membered monocyclic aromatic heterocyclic ring systems containing from one to three, the same or different, heteroatoms selected from the group consisting of nitrogen, oxygen and sulfur (or said 5- or 6-membered monocyclic aromatic heterocyclic ring system substituted on any available carbon atom thereof by hydroxy, lower-alkyl, oxo, nitro, halogen, or lower-alkoxy; or on any available nitrogen atom thereof by lower-alkyl, trilower alkylsilyl, trilower-alkylsilyl-lower-alkoxy-lower-alkyl or phenyl-lower-alkyl (or said phenyl-lower-alkyl group substituted on the phenyl group by lower-alkoxy, lower-alkyl, or halogen)). Representative examples of such 5- or 6-membered monocyclic aromatic heteocyclic ring systems include, but are not limited to, furan, pyridine, thiophene, oxazole, thiazole, pyrazole, triazole, pyrrole, imidazole; isoxazole, oxadiazole, pyrazine, pyridazine, pyrimidine, triazine, thiadiazole and the like; or said 5- or 6-membered monocyclic aromatic heterocyclic ring systems substituted on any available carbon or nitrogen atom thereof as described hereinabove.

The term 9- or 10-membered bicyclic aromatic heterocyclic ring system as used herein means 9- or 10-membered bicyclic aromatic heterocyclic ring systems containing from one to three, the same or different, heteroatoms selected from the group consisting of oxygen, nitrogen and sulfur (or said 9- or 10-membered bicyclic aromatic heterocyclic ring system substituted on any available carbon atom thereof by hydroxy, lower-alkyl, oxo, nitro, halogen, or lower-alkoxy; or on any available nitrogen atom thereof by lower-alkyl, trilower-alkylsilyl, trilower-alkylsilyl-lower-alkoxy-lower-alkyl or phenyl-lower-alkyl (or said phenyl-lower-alkyl group substituted on the phenyl group by lower-alkoxy, lower-alkyl, or halogen)). Representative examples of such 9- or 10-membered bicyclic aromatic heterocyclic ring systems include, but are not limited to, benzofuran, benzimidazole, thianaphthene, benzisothiazole, quinoline, isoquinoline, quinoxaline, quinazoline, indole, 1,8-naphthyridine, benzothiazole, benzoxazole, indazole, benzotriazole and the like; or said 9- or 10-membered bicyclic aromatic heterocyclic ring system substituted on any available carbon or nitrogen atom thereof as described hereinabove.

The term 5- or 6-membered monocyclic nonaromatic heterocyclic ring system as used herein means 5- or 6-membered nonaromatic heterocyclic ring systems containing from one to two, the same or different, heteroatoms selected from the group consisting of nitrogen, oxygen and sulfur (or said 5- or 6-membered monocyclic nonaromatic heterocyclic ring system substituted on any available carbon atom thereof by hydroxy, lower-alkyl, oxo, nitro, halogen, or lower-alkoxy; or on any available nitrogen atom thereof by lower-alkyl, trilower-alkylsilyl, trilower-alkylsilyl-lower-alkoxy-lower-alkyl, or phenyl-lower-alkyl (or said phenyl-lower-alkyl group substituted on the phenyl group by lower-alkoxy, lower-alkyl or halogen)). Representative examples of such 5- or 6- membered monocyclic nonaromatic heterocyclic ring systems include, but are not limited to, pyrrolidine, thiazolidine, tetrahydrofuran, tetrahydrothiophene, thiomorpholine, morpholine, piperazine, piperidine, tetrahydropyran, 1,4-thioxan, and the like; or said 5- or 6-membered monocyclic nonaromatic heterocyclic ring system substituted on any available carbon or nitrogen atom thereof as described hereinabove.

The term 5- or 6-membered monocyclic aromatic heterocycle as used herein means 5- or 6-membered monocyclic aromatic heterocycles containing from two to three, the same or different, heteroatoms selected from the group consisting of nitrogen, oxygen and sulfur or said 5- or 6-membered monocyclic aromatic heterocycles substituted on any available carbon atom thereof by hydroxy, OC(O)alkyl-CH=CH-alkyl, OC(O)alkyl; OC(O)lower-alkenyl-C(O)Oalkyl, alkoxy, OC(O)alkylC(O)Oalkyl, nitro, amino, lower-alkylsulfonylamino, lower-alkyl, lower-alkoxy, or halogen; or on any available nitrogen atom thereof by phenyl (or said phenyl group substituted by lower-alkoxy, lower-alkyl or halogen), diphenylmethyl, naphthyl-lower-alkyl (or said naphthyl-lower-alkyl group substituted on the naphthyl group by lower-alkoxy, lower-alkyl or halogen), lower-alkyl, or phenyl-lower-alkyl (or said phenyl-lower-alkyl group substituted on the phenyl group by lower-alkoxy, lower-alkyl, or halogen)). Representative examples of such heterocycles include, but are not limited to, thiazolyl, imidazolyl, triazolyl, pyrazinyl, pyrimidinyl, pyridazinyl, oxazolyl, oxadiazolyl, pyrazolyl, triazinyl and the like; or said heterocycles substituted on any available carbon atom or nitrogen atom thereof as described hereinabove.

It will be appreciated that in the compounds of the formulas I and II, $X^-$ is an anion when p, in the term $(X^-)_p$, is one; however, when the compounds of the Formula I and II contain a negatively charged radical, e.g. when $R^6$ is $CO_2^-$, $SO_3^-$, or $PO_3^-$, p, in the term $(X^-)_p$, is zero and the compounds exist as zwitterionic species.

The numbering system used throughout the specification is shown in the ring systems, labelled C and D, which are illustrated below. Throughout the specification the compounds of the invention wherein A is a 5-membered monocyclic aromatic heterocycle (ting system C) will be named as substituted 5,10-ethano-5,10-dihydroheterocyclylisoquinolinium salts; and the compounds

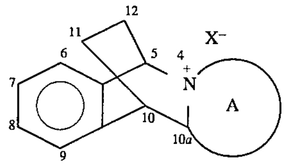
C

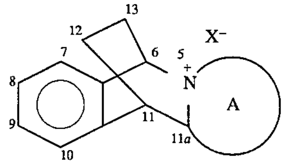
D of the invention wherein A is a 6-membered monocyclic aromatic heterocycle (ring system D) will be named as a substituted 6,11-ethano-6,11-dihydroheterocyclylisoquinolinium salts.

The synthesis of the compounds of the invention may be outlined as shown in Scheme A:

Scheme A

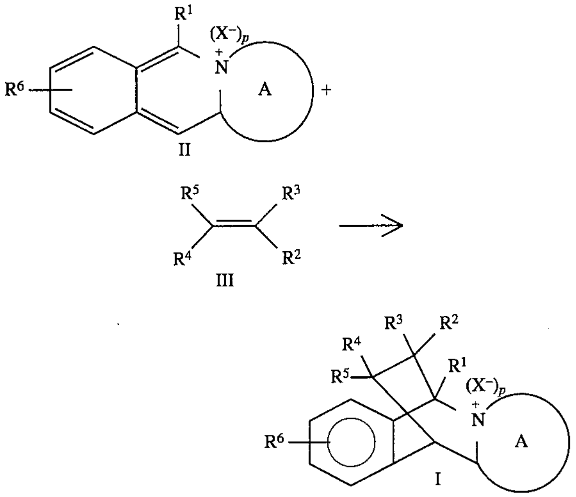

II III I

A suitably substituted heterocyclylisoquinolinium salt of the formula II in an appropriate organic solvent, e.g. acetonitrile, nitromethane, nitropropane, or lower-alkanol solvents (such as ethanol); or a mixture of said solvents, optionally in the presence of the catalytic amount of an alkali metal carbonate, e.g. $CaCO_3$, is treated with an excess of an appropriately substituted olefin (III), at a) a temperature in the range of about 50° C. up to the boiling point of the solvent or solvent mixture used, preferably at a temperature in the range of about 90° C. up to the boiling point of the solvent or solvent mixture used, or b) at about room temperature in a high pressure apparatus at about 10 Kbar, to afford the compounds of Formula I.

If desired, the compounds of Formula I can be converted into other compounds of Formula I which possess various different anion groups ($X^-$) by a) treating a compound of Formula I with an aqueous solution of the alkali metal salt of an inorganic acid anion or an organic acid anion, $M^+X^-$, wherein the acid of the salt used is a stronger acid than the corresponding acid of the initial acid anion ($X^-$) and wherein $M^+$ is an alkali metal, e.g. sodium, or potassium, to produce compounds of the Formula I wherein $X^-$ is various other anion groups ($X^-$); b) if compounds of the formula I wherein $X^-$ is chloride ($Cl^-$) are desired, by passing a compound of the Formula I wherein $X^-$ is other than $Cl^-$ through a Dowex® 1X2-200 ($Cl^-$) ion exchange resin (Dowex®-1-$Cl^-$) column to afford the compounds of Formula I wherein $X^-$ is $Cl^-$; or c) by passing a compound of the Formula I through a suitable ion-exchange resin column (prepared, for example, by treating Dowex® 1X2-200 ($Cl^-$) ion-exchange resin with a suitable organic acid or inorganic acid) to provide various compounds of Formula I wherein $X^-$ is other than $Cl^-$, $ClO_4^-$ or $PF_6^-$.

It will be appreciated that the compounds of the Formula I can possess one or more asymmetric carbon atoms and are thus capable of existing in a number of stereoisomeric forms, e.g. enantiomers, diastereomers, and geometric isomers. Unless otherwise specified herein, the invention is intended to extend to each of these steroisomeric forms, and to mixtures thereof, including the racemates. In some cases there may be advantages, e.g. greater potency to using a particular enantiomer when compared to the other enantiomer or the racemate in the treatment or prevention of neurodegenerative disorders or neurotoxic injuries, and such advantages can be readily determined by those skilled in the art. The different stereoisomeric forms may be separated one from the other by the methods described hereinbelow:

The diastereomers/geometric isomers can be separated by conventional procedures which are well known in the art of chemistry such as chromatography, fractional crystallization and the like. The separation of enantiomers can be accomplished by a) chiral chromatography, b) treating a racemic mixture of a compound of Formula I with the potassium salt of (+)-dibenzoyl-D-tartaric acid ($K^+$[(+)-DBT]) to afford a compound of Formula I as the $^-$[(+)-DBT] salt; fractional crystallization of the $^-$[(+)-DBT] salt to afford a single diastereomer of the $^-$[(+)-DBT] salt, and then conversion of the single diastereomer of the $^-$[(+)-DBT] salt into various other non-chiral anions ($X^-$) by following the procedures described hereinabove for the conversion of compounds of the Formula I into other compounds of the Formula I with various different anions ($X^-$), to produce the compounds of the Formula I as a single enantiomer; or c) treating a racemic mixture of a compound of Formula I with the potassium salt of (−)-dibenzoyl-L-tartaric acid ($K^+$[(−)-DBT]) to afford a compound of Formula I as the $^-$[(−)-DBT] salt and then proceeding as described hereinabove in part (b) to afford the compounds of Formula I as the other enantiomer.

Simple chemical tranformations which are conventional and well known to those skilled in the art of chemistry can be used for effecting changes in the functional groups of the compounds of the Formula I. For example, removal of N-(tri-lower-alkylsilyl), and N-lower-alkoxyphenyl-lower-alkyl protecting groups to afford the corresponding N-H derivatives, treatment of 2-lower-alkoxy pyridine derivatives with an acid to produce the corresponding 2-oxopyridine derivatives, conversion of furan derivatives into the corresponding 2-oxofuran derivatives, treatment of alcohols with acylating agents to afford the corresponding esters, hydrolysis of nitriles to afford the corresponding acids, treatment of acids with alcohols in the presence of a dehydrating agent to afford the corresponding ester, treatment of halides with dialkylphosphites in the presence of a catalyst to produce phosphonates which in turn can be hydrolyzed to afford to corresponding phosphonic acid derivatives, treatment of alcohols with alkyl halides to afford the corresponding alkoxy derivatives, reduction of nitro derivatives to afford the corresponding amino derivatives, treatment of amino derivatives with sulfonyl halides to afford the corresponding sulfonamide derivatives, and dealkylation of ethers to produce the corresponding alcohols.

The suitably substituted heterocyclylisoquinolinium salts of the Formula II, which are required for the synthesis of the compounds of Formula I, can be prepared by the procedures described herein below and illustrated in Schemes B and C.

Scheme B

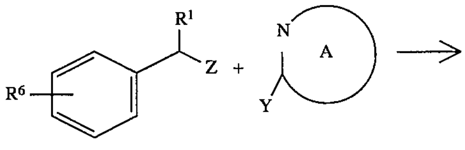

IV V

-continued

Scheme B

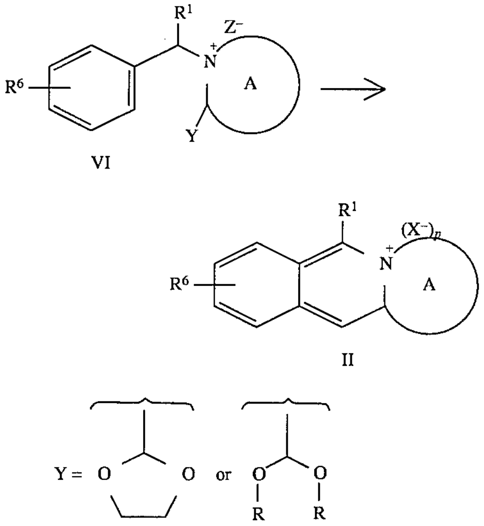

VI

II

Y = or

In Scheme B, at least one mole of a suitably substituted benzyl halide(IV), wherein Z is a halogen, preferably bromine, is treated with an appropriately substituted heterocyclic acetal of the Formula V, wherein Y is a 1,3-dioxolan-2-yl group or a dilower-alkyl acetal group (R=lower alkyl), in the absence of a solvent, at a temperature in the range of about room temperature up to about 100° C. to produce a quaternary ammonium salt of the Formula VI. The quaternary ammonium salt of the Formula VI can then be treated with an excess of an acid, e.g. 48% hydrobromic acid, or polyphosphoric acid, at a temperature in the range of about room temperature up to the boiling point of the reaction mixture, to produce the substituted heterocyclylisoquinolinium salts of the Formula II.

Alternatively, the compounds of the Formula II can be prepared as shown in Scheme C. A suitably substituted benzyl alcohol (VII), where Y' is hydrogen or halogen, preferably hydrogen, or bromine, in a suitable organic solvent, Scheme C

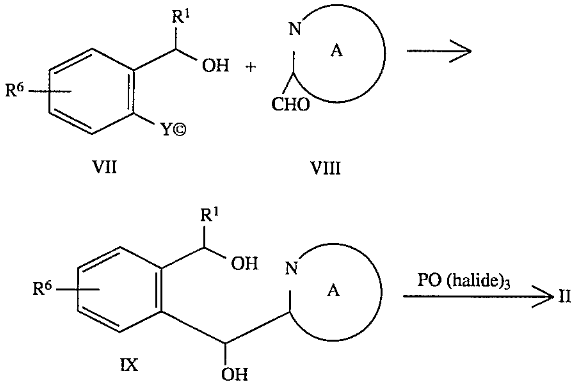

VII VIII

IX e.g. ether, is treated with at least two molar equivalents of a lower-alkyl alkali metal, preferably n-BuLi, optionally in the presence of at least one mole of a second base, e.g. N, N, N', N'-tetramethylethylenediamine, followed by the addition of at least one molar equivalent, preferably an excess of a suitably substituted 5- or 6-membered monocyclic aromatic heterocyclic carboxaldehyde of the Formula VIII, at a temperature in the range of room temperature or below, preferably at a temperature in the range of room temperature to about −30° C. to afford the diol (IX). The diol (IX) can then be treated with an excess of a phosphorous oxyhalide, preferably phosphorous oxychloride, at a temperature in the range of about room temperature up to the boiling point of the phosphorous oxyhalide, to afford compounds of the Formula II wherein $X^-$ is a halogen.

If desired, the compounds of the Formula II can be converted into other compounds of the Formula II which possess various different anion groups, $X^-$, by following procedures similar to those described hereinabove for the conversion of the compounds of the Formula I to various other anion groups, $X^-$.

Simple chemical transformations which are conventional and well known to those skilled in the art of chemistry can be used for effecting changes in the functional groups of the compounds of Formula II. For example, dealkylation of ethers to produce the corresponding alcohols, acetylation of alcohols to produce the corresponding acetates, and treatment of aromatic derivatives with sulfonic acid to afford the corresponding sulfo and $SO_3^-$ substituted derivatives.

The appropriately substituted olefin (III), alkali metal salts of an inorganic acid anion or an organic acid anion ($M^+X^-$), benzyl halide (IV), heterocyclic acetal (V), benzyl alcohol (VIII), and the 5- or 6-membered monocyclic aromatic heterocyclic carboxaldehyde (VIII) are commercially available, or they can be prepared by procedures well known in the art, or by the procedures described hereinbelow.

The compounds of Formula I, which contain basic substituents are useful both in the free base form and in the form of acid-addition salts, and, both forms are within the purview of the invention. The acid-addition salts are often a more convenient form for use; and in practice, use of the salt form inherently amounts to use of the base form. The acids which can be used to prepare the acid-addition salts include preferably those which produce, when combined with the free base, pharmaceutically-acceptable salts, that is, salts whose anions are relatively innocuous to the animal organism in pharmaceutical doses of the salts, so that the beneficial properties inherent in the free base are not vitiated by side effects ascribable to the anions. In practicing the present invention it is convenient to use the free base form or the hydrochloride, fumarate, toluenesulfonate, methanesulfonate or maleate salts. However, other appropriate pharmaceutically acceptable salts within the scope of the invention are those derived from other mineral acids and organic acids. The acid-addition salts of the basic compounds are prepared by standard procedures well known in the art which include, but are not limited thereto, dissolving the free base in an aqueous alcohol solution containing the appropriate acid and isolating the salt by evaporating the solution, or by reacting the free base and an acid in an organic solvent, in which case the salt separates directly, or is precipitated with a second organic solvent, or can be obtained by concentration of the solution. Although medicinally acceptable salts of the basic compounds are preferred, all acid-addition salts are within the scope of the present invention. All acid-addition salts are useful as sources of the free base form even if the particular salt per se is desired only as an intermediate product, as, for example, when the salt is formed for purposes of purification or identification, or when it is used as an intermediate in preparing a medicinally acceptable salt by, for example, ion exchange procedures.

The compounds of Formula I, are substituted heterocyclylisoquinolinium salts in which it is preferred that the salts are pharmaceutically acceptable salts, that is, salts whose anions ($X^-$) are relatively innocuous to the animal organism in pharmaceutical doses of the salts, so that the beneficial properties inherent in the compounds of the Formula I are not vitiated by side effects ascribable to the anions ($X^-$). In practicing the present invention it is convenient to use the anions ($X^-$) of organic acids such as methanesulfonic acid and toluenesulfonic acid, or the anions ($X^-$) of inorganic acids such as hydrobromic acid and hydrochloric acid. However, other appropriate pharmaceutically acceptable salts within the scope of the invention are those derived from the anions ($X^-$) of other organic acids, organic diacids, or inorganic acids.

The structures of the compounds of the invention were established by the mode of synthesis, and by one or more of elemental analysis, and infrared, nuclear magnetic resonance and mass spectroscopy. The course of the reactions and the identity and homogeneity of the products were assessed by one or more of thin layer chromatography (TLC), high pressure liquid chromatography (HPLC), or gas-liquid chromatography (GLC).

The following examples will further illustrate the invention without, however, limiting it thereto. All melting points (m.p.) are given in degrees centigrade (°C.) and are uncorrected. As used herein, the abbreviation PAW stands for pyridine/acetic acid/water (55/20/25); DME stands for dimethoxyethane; THF stands for tetrahydrofuran; DMPU stands for 1,3-dimethyl-3,4,5,6-tetrahydro-2(1H)pyrimidinone, and DMAP stands for 4-dimethylaminopyridine.

EXAMPLE 1

(a)

To a solution of n-butyllithium (3.14 g, 49 mmol, 2M in hexane) in 80 ml of ether under argon at −78° C. was added dropwise a solution of 2-bromothiazole (7.8 g, 47.55 mmol) in 1 h. The mixture was stirred at −78° C. for 1 h, and then a solution of DMF (3.48 g, 47.55 mmol) in ether was added. The mixture was stirred for 1 h at −78° C., then at −15° C. for 18 h. The reaction mixture was then extracted with 4N HCl (4×20 ml), the aqueous layers were combined, cooled in an ice-bath, and neutralized with sodium bicarbonate. The aqueous layer was extracted with ether (4×35 ml), the organic layer was dried over sodium sulfate and concentrated in vacuo to afford 4.95 g (93.9%) of 2-thiazolylcarboxaldehyde.

(b)

A mixture of 2-thiazolylcarboxaldehyde (5 g, 44.25 mmol), 4.9 ml (88.5 mmol) of ethylene glycol, 200 ml of toluene and 2.1 g (11.06 mmol) of p-toluenesulfonic acid monohydrate under argon in a 3 neck-flask equipped with a Dean-Stark trap was heated to reflux for 6 h separating the water formed. The mixture was cooled to room temperature, and poured into an ice-cold 10% sodium carbonate solution. The aqueous layer was extracted with ether, the combined organic layer was washed with brine and dried over sodium sulfate, and concentrated in vacuo to afford 3.1 g (44.6%) of 2-(1,3-dioxolan-2-yl)thiazole (Formula V: A=2-thiazolyl; Y=1,3-dioxolan-2-yl).

(c)

A reaction mixture of 3.1 g (19.74 mmol) of 2-(1,3-dioxolan-2-yl)thiazole and 3.38 g (19.74 mmol) of benzyl bromide was heated on a steam-bath with stirring for 6 h. The mixture was cooled to room temperature, triturated with ethyl acetate and decanted to afford 5.5 g (84.9%) of 3-benzyl-2-(1,3-dioxolan-2-yl)thiazolium bromide (Formula VI: A=2-thiazolyl; Y=1,3-dioxolan-2-yl; $R^1$=$R^6$=H; $Z^-$=$Br^-$).

(d)

A mixture of 3-benzyl-2-(1,3-dioxolan-2-yl)thiazolium bromide (3.1 g,19.74 mmol) and 30 ml of 48% HBr was heated on a steam-bath with stirring for 5 h. The mixture was cooled to room temperature, concentrated in vacuo, and the resulting brown residue was redissolved in water. The aqueous solution was filtered and the filtrate was treated with 10% sodium perchlorate solution. The precipitated product was filtered, washed with water, ether, and dried in vacuo to afford 2.4 g (50%) of thiazolo[3,2-b]isoquinolinium perchlorate (Formula II: A=thiazolo; $R^1$=$R^6$=H; $X^-$=$ClO_4^-$).

(e)

To a solution of isobutyronitrile (691.1 g) in ethanol (506.22 g) at 0° C. was bubbled HCl gas at the rate of 2.75 L/minute for 96 minutes. The reaction mixture was sealed, refrigerated for 6 days and then stirred at room temperature for one day. The mixture was filtered, the filtrate was poured into ether (9 L) with stirring at 0° C. and the precipitate which formed was collected by filtration and dried over KOH to afford 800 g of 1-imino-1-ethoxyisobutane hydrochloride.

(f)

To a suspension of 1-imino-1-ethoxyisobutane hydrochloride (610.0 g) in ether (12.5 L) was added ethanol (1940.0 g, 10 mol). The mixture was stirred at 35°–37° C. under $N_2$ for 72 hours. The reaction mixture was filtered, the filtrate was washed with a 10% sodium carbonate solution, followed by a saturated sodium carbonate solution and the organic layer was dried over $K_2CO_3$. The organic layer was concentrated in vacuo and the residue was dissolved in ether, filtered and the filtrate was washed successively with a 10% NaOH solution and water. The organic layer was dried over $K_2CO_3$, the solvent was removed in vacuo and the residue was diluted with hexane, cooled in an ice-bath and filtered. The filtrate was concentrated in vacuo and the residue was distilled at 70°–72° C. (27 mmHg) to afford 320 g (42%) of 1,1,1-triethoxyisobutane.

(g)

A mixture of 1,1,1-triethoxyisobutane (27.5 g, 0.14 mol) and aluminium t-butoxide (30 g, 0.12 mol) was heated at 170° C. for 1 hour during which time t-butanol distilled off. The residue was distilled at 100°–130° C. (atomosphere pressure) to afford 12.1 g (58%) of 1,1-diethoxy-2,2-dimethylethylene (Formula III: $R^2$=$R^3$=$CH_3$; $R^4$=$R^5$=$OC_2H_5$), as a clear oil.

(h)

A reaction mixture containing thiazolo[3,2-b]isoquinolinium perchlorate (0.57 g; 2 mmol) and 2,2-di(methyl)-1,1-di(ethoxy)ethylene (0.65 g; 4.5 mmol) in 10 ml of acetonitrile was heated to reflux under argon with stirring for 24 h. The reaction mixture was concentrated in vacuo, the residue was passed through a silica column (methylene chloride/methanol, 9:1) to afford 700 mg (81.5%) of 11,11-diethoxy-12,12-dimethyl-5,10-ethano-5,10-dihydrothiazolo

[3,2-b]isoquinolinium perchlorate (Formula I: A=thiazolo; $R^1$=$R^6$=H; $R^2$=$R^3$=$CH_3$; $R^4$=$R^5$=$OC_2H_5$; $X^-$=$ClO_4^-$).

(i)

11,11-Diethoxy-12,12-dimethyl-5,10-ethano-5,10-dihydrothiazolo[3,2-b]isoquinolinium perchlorate (700 mg, 1.63 mmol) was converted to the corresponding chloride by passing the salt through Dowex® 1x2-200($Cl^-$). The salt was recrystallized from methylene chloride/ether to afford 350 mg (54%) of 11,11-diethoxy-12,12-dimethyl-5,10-ethano-5,10-dihydrothiazolo[3,2-b]isoquinolinium chloride ⅗ hydrate (Formula I: A=thiazolo; $R^1$=$R^6$=H; $R^2$=$R^3$=$CH_3$; $R^4$=$R^5$=$OC_2H_5$; $X^-$=$Cl^-$), m.p. 122°–124° C.(d).

EXAMPLE 2

(a)

A reaction mixture containing thiazolo[3,2-b]isoquinolinium perchlorate (0.57 g; 2 mmol) and 1,1-di(phenyl)ethylene (0.72 g; 4 mmol) in 10 ml of nitromethane was heated to reflux under argon with stirring for 48 h. After adding an additional 1,1-di(phenyl)ethylene (0.7 ml) heating was continued for an additional 48 h. The reaction mixture was concentrated in vacuo, the residue was triturated with hexane and decanted to afford 950 mg of 11,11-diphenyl-5,10-ethano-5,10-dihydrothiazolo[3,2-b]isoquinolinium perchorate. The above salt was purified by column chromatography a silica gel (methylene chloride/methanol, 9:1) to afford 650 mg of 11,11-diphenyl-5,10-ethano-5,10-dihydrothiazolo[3, 2-b]isoquinolinium perchlorate (Formula I: A=thiazolo; $R^1$=$R^2$=$R^3$=$R^6$=H; $R^4$=$R^5$=phenyl; $X^-$=$ClO_4^-$).

(b)

11,11-Diphenyl-5,10-ethano-5,10-dihydrothiazolo[3,2-b] isoquinolinium perchlorate (650 mg) was convened to the corresponding chloride by passing the salt through Dowex® 1x2-200($Cl^-$). The salt was recrystallized from methylene chloride/ether to afford 410 mg (51%) of 11,11-diphenyl-5,10-ethano-5,10-dihydrothiazolo[1,2-b]isoquinolin-4-ium chloride (Formula I: A=thiazolo; $R^1$=$R^2$=$R^3$=$R^6$=H; $R^4$=$R^5$=phenyl; $X^-$=$Cl^-$), m.p. 155°–157° C.

EXAMPLE 3

(a)

A reaction mixture containing 1-methylimidazo[1,2-b] isoquinolin-4-ium perchlorate (3.0 g; 10.5 mmol) and 1,1-di(phenyl)ethylene (3.47 g; 19.3 mmol) in 25 ml of nitromethane was heated to reflux under argon with stirring for 3 days. The reaction mixture was concentrated in vacuo, the residue was passed through a silica column (methylene chloride/methanol, 9:1) to afford 3.1 g of 11,11-diphenyl-5,10-ethano-5,10-dihydro-1-methylimidazo-[1,2-b]isoquinolin-4-ium perchlorate (Formula I: A=1-methylimidazo; $R^1$=$R^2$=$R^3$=$R^6$=H; $R^4$=$R^5$=phenyl; $X^-$=$ClO_4^-$).

(b)

11,11-Diphenyl-5,10-ethano-5,10-dihydro-1-methylimidazo[1,2-b]isoquinolin-4-ium perchlorate (3.1 g) was converted to the corresponding chloride by passing the salt through Dowex® 1x2-200 ($Cl^-$). The salt was recrystallized from methylene chloride to afford 700 mg of 11,11-diphenyl-5,10-ethano-5,10-dihydro-1-methylimidazo[1,2-b]isoquinolin-4-ium chloride (Formula I: A=1-methylimidazo; $R^1$=$R^2$=$R^3$=$R^6$=H; $R^4$=$R^5$=phenyl; $X^-$=$Cl^-$), m.p. 186°–188° C.

EXAMPLE 4

(a)

To a suspension of furan-3-carboxylic acid (36 g, 0.32 mol) in 250 ml of toluene was added 49 g (0.385 mol) of oxalyl chloride and 1 drop of pyridine, and the mixture was heated at 80°–90° C. for 1.5 h. The mixture was cooled to room temperature, N,O-dimethylhydroxylamine hydrochloride (35 g, 0.36 mol), 4-dimethylaminopyridine (DMAP, 1.8 g, 0.0147 mol), and 600 ml of methylene chloride were added. The mixture was cooled to 0° C., 68.4 g of pyridine was added slowly, the mixture was allowed to warm to room temperature and stirred for 2 h. The mixture was filtered, and the filtrate was washed with water, 5% aqueous dimethylaminopropylamine, water, 6N HCl solution, water, and brine. The organic layer was dried and concentrated in vacuo, and the residue was distilled (b.p. 85°–87° C./0.2 mm) to afford 44 g (88.7%) of 3-(N-methyl-N-methoxycarbamoyl)furan.

(b)

To a solution of n-butyllithium (2.5M, 28 ml, 0.07 mol) in 150 ml of ether at −78° C. was added a solution of 3-bromofuran (10 g, 0.0628 mol) in 30 ml of ether over a 20 min period and the mixture was stirred at −78° C. for 20 min. To the above mixture was added 3-(N-methyl-N-methoxycarbamoyl)furan (9.16 g, 0.059 mol) in 30 ml of ether over a 15 min period and the mixture was stirred at room temperature for ½ h. The reaction mixture was quenched with 200 ml of ammonium chloride solution, 500 ml of methylene chloride was added and the mixture was stirred. The organic layer was dried over sodium sulfate, concentrated in vacuo, and the residue was triturated in 100 ml of hexane/t-butylmethylether (9:1). The solid product was filtered and washed with t-butylmethylether to afford 7.5 g (78.3%) of di-(3-furyl)ketone.

(c)

To a suspension of methyltriphenylphosphonium bromide (145 g; 0.405 mol, dried at 60° C.) in 1 L of ether was added at −20° C. n-butyllithium in hexane (2.5M, 162 ml; 0.405 mol) and the mixture was allowed to stir at room temperature for 1 h. To the above mixture was added 60 g (0.37 mol) of 1,1-di(3-furyl)ketone in 450 ml of DME/THF/DMPU (2:2:0.5) in 10 minutes and the mixture was stirred at room temperature for 1 h.. To the above reaction mixture was added saturated ammonium chloride solution (250 ml), and the mixture was diluted with 500 ml of water. The organic layer was separated, washed with water (2×500 ml), dried, and concentrated in vacuo. The residue was purified by chromatography on silica (hexane, then 10% ether/hexane) to afford 51 g (86%) of 1,1-di(3-furyl)ethylene (Formula III: $R^2$=$R^3$=H; $R^4$=$R^5$=3-furanyl). This product was further distilled (b.p. 60°–63° C./0.01 mm).

(d)

A mixture of 1.5 g (0.01 mol)) of thiazolo[3,2-b]isoquinolinium perchlorate and 1.3 g (8 mmol) of 1,1-di-(3-furyl) ethylene in 50 ml of nitromethane was heated to reflux under nitrogen for 3 h. The mixture was cooled and concentrated in vacuo. The residue was triturated with ether/ethyl acetate (75 ml), filtered to yield a crude product. This solid was triturated in 50 ml of methylene chloride and the solid was collected by filtration. The solid product was washed with ether, isopropanol, methylene chloride, and dried to afford 1.7 g of 11,11-di(3-furyl)-5,10-ethano-5,10-dihydrothiazolo [3,2-b]isoquinolinium perchlorate (Formula I: A=thiazolo; $R^1$=$R^2$=$R^3$=$R^6$=H; $R^4$=$R^5$=3-furanyl; $X^-$=$ClO_4^-$).

(e)

11,11-Di(3-furyl)-5,10-ethano-5,10-dihydrothiazolo[3,2-b]isoquinolinium perchlorate was converted to the corresponding chloride by passing the salt through Dowex® 1x2-200-$Cl^-$. The desired fractions were passed through a pad of Solka Floc® and the filtrate was concentrated in vacuo to afford 1.2 g (82.2%) of 11,11-di(3-furyl)-5,10-ethano-5,10-dihydrothiazolo[3,2-b]isoquinolinium chloride (Formula I: A=thiazolo; $R^1$=$R^2$=$R^3$=$R^6$=H; $R^4$=$R^5$=3-furanyl; $X^-$=$Cl^-$).

EXAMPLE 5

(a)

To a solution of 188.2 g (0.5 mol) of (–)-O,O'-dibenzoyl-L-tartaric acid in 1.3 L of methanol was added over a 10 min period a solution of 50.1 g (0.5 mol) of potassium hydrogen carbonate in 300 ml of water, and the mixture was stirred overnight at room temperature. The solid product was filtered, washed with methanol, and dried in vacuo to afford 170.9 g of the mono-potassium salt of (–)-O,O'-dibenzoyl-L-tartaric acid.

(b) and (c)

To 11,11-di(3-furyl)-5,10-ethano-5,10-dihydrothiazolo[3,2-b]isoquinolinium perchlorate (23 g, racemate) dissolved in a hot solution of 300 ml of acetonitrile and 150 ml of methanol was added 3 spoonsfuls of activated charcoal, and the mixture was refluxed for 3 min, filtered while hot, and the residue was washed with 100 ml of methanol. The filtrate was concentrated in vacuo, the residue dissolved in 20 ml of acetonitrile, and passed through Dowex® 1x2-200 ($Cl^-$) (250 g of resin). Concentration of the eluent afforded 18.38 g of 11,11-di(3-furyl)-5,10-ethano-5,10-dihydrothiazolo[3,2-b]isoquinolinium chloride (racemate), as a pale clear glass.

11,11-Di(3-furyl)-5,10-ethano-5,10-dihydrothiazolo[3,2-b]isoquinolinium chloride (racemate, 18.38 g. 38.9 mmol) was dissolved in a minimum of warm methanol (100 ml). In a separate flask, 16.998 g (0.0429 mol) of mono-potassium salt of (–)-O,O'-dibenzoyl-L-tartaric acid was dissolved in 700 ml of hot methanol, and 50 ml of water added to the above solution. The above two solutions were mixed together to form a clear solution. The solution was concentrated in vacuo, the residue was stirred with 200 ml of methylene chloride and concentrated in vacuo. The resulting residue was stirred with 600 ml of methylene chloride with warming, filtered to remove the insoluble solid. The insoluble solid was washed with 150 ml of hot methylene chloride, the combined methylene chloride filtrate was concentrated in vacuo. The above residue was dissolved in 250 ml of warm acetonitrile, seeded, cooled, and filtered to yield a white solid product. The white solid product was dissolved in 600 ml of hot acetonitrile, the solution was concentrated to 400 ml of its volume, cooled, and filtered to afford 13.5 g of 11,11-di(3-furyl)-5,10-ethano-5,10-dihydrothiazolo[3,2-b]isoquinolinium(–)-O,O'-dibenzoyl-L-tartrate (Formula I: A=thiazolo; $R^1$=$R^2$=$R^3$=$R^6$=H; $R^4$=$R^5$=3-furanyl; $X^-$=[(–)-DBT]$^-$; Example 5(b)). The tartrate was recrystallized from hot ethanol and converted to the corresponding chloride salt by stirring the solid in a mixture of 600 mL 1N HCl, and 300 mL ether, until a clear solution resulted. The layers were then separated, and the aqueous layer extracted 2×200 mL ether. The aqueous layer was then evaporated to afford a residue with an ee of 99.8% but still containing thiazolo [3,2-b]isoquinolinium chloride as an impurity. This residue was then further purified as follows: the chloride salt was dissoved in 100 ml of water, treated with 14 g of sodium perchlorate in 100 ml of water to yield the corresponding perchlorate salt. The perchlorate salt was purified by chromatography on silica (methylene chloride/ethyl acetate/methanol 7:2:1), and subsequently converted to the chloride salt (Dowex® 1x2-200 ($Cl^-$) to afford (–)-11,11-di(3-furyl)-5,10-ethano-5,10-dihydrothiazolo[3,2-b]isoquinolinium chloride (Example 5(c), enantiomeric purity 99.8% ee, first eluting peak) (Formula I: A=thiazolo; $R^1$=$R^2$=$R^3$=$R^6$=H; $R^4$=$R^5$=3-furyl; $X^-$=$Cl^-$,(–)-enantiomer), as a brown solid, $[\alpha]^{24}_{435}$=–84.6° in DMF m.p. 137° C. (softens) C=10 mg/ml.

(d) and (e)

All mother liquors were combined, concentrated in vacuo, and the resulting residue was partitioned between 500 ml of 0.5N HCl and 300 ml of ether with stirring. The aqueous layer was washed with ether (2×200 ml), concentrated in vacuo, and the residue was triturated with ether/acetonitrile and dried to afford 9.1 g of the chloride. The solid was mixed with the solution of 9.51 g (20 mmol) of mono-potassium salt of (+)-O,O'-dibenzoyl-D-tartaric acid in 500 ml of hot methanol. Upon concentration in vacuo, 15.9 g of yellow foam was obtained and this salt was recrystallized from acetonitrile (2×) and ethanol to afford 7.68 g of 11,11-di(3-furyl)-5,10-ethano-5,10-dihydrothiazolo[3,2-b]isoquinolinium(+)-O,O'-dibenzoyl-D-tartarate (Formula I: A=thiazolo; $R^1$=$R^2$=$R^3$=$R^6$=H; $R^4$=$R^5$=3-furanyl; $X^-$=[(+)-DBT]$^-$; Example 5(d)), as a single diasteriomer. The solid was converted to the coresponding chloride salt by partitioning between 300 ml of 0.5N HCl and 700 ml of ether with stirring. The aqueous layer was washed with ether (2×50 ml), treated with activated charcoal, filtered through Solka Floc®, the residue washed with 100 ml of water, and the aqueous layer was concenturated in vacuo to afford a residue which was purified as described hereinabove in Example 5(c) to afford (+)-11,11-di(3-furyl)-5,10-ethano-5,10-dihydrothiazolo[3,2-b]isoquinolinium chloride (enantimeric purity 97.7% ee, 2nd eluting peak, Example 5 (e)) (Formula I: A=thiazolo; $R^1$=$R^2$=$R^3$=$R^6$=H; $R^4$=$R^5$=3-furyl; $X^-$=$Cl^-$, as (+)-enantiomer) as a brown solid, $[\alpha]^{24}_{435}$=+78.6° in DMF m.p. 130° C. (softens).

EXAMPLE 6

(a)

To a solution of 5.25 g (0.04 mol) of m-methoxybenzyl alcohol in 100 ml of ether cooled to –40° C. was added dropwise 5.05 g (0.08 mol) of 2.5M n-butyllithium in hexane followed by 4.65 g (0.04 mol) of TMEDA, and the reaction mixture was slowly warmed to room temperature and stirred. The above reaction mixture was cooled to –20° C., 5 g (0.04 mol) of 2-thiazolylcarboxaldehyde in 10 ml of ether was added, and the resulting reaction mixture was allowed to warm to room temperature. After 1 hour, ammonium chloride solution was added to the mixture. The diol was extracted with ethyl acetate, dried over sodium sulfate, and the solvent was removed in vacuo. The residue was purified by chromatography on silica (methylene chloride/methanol, 9:1) to afford 4.2 g (41.8%) of 2-[1-hydroxy-(2'-methoxy-6'-hydroxymethyl)-benzyl]thiazole (Formula IX: A=thiazolo; $R^1$=H; $R^6$=2'-methoxy).

(b)

A mixture of 4 g (15.9 mmol) of 2-[1-hydroxy-(2'-methoxy-6'-hydroxymethyl)-benzyl]thiazole and 25 ml of $POCl_3$ was refluxed with stirring for 4 h. The mixture was cooled, poured into ice, and the mixture was stirred overnight. The resulting dark solution was filtered through a filter pad, treated with sodium perchlorate solution, the resulting solid was filtered, washed, and dried to afford 1.3 g (26%) of 9-methoxy-thiazolo[3,2-b]isoquinolinium perchlorate (Formula II: A=thiazolo; $R^1$=H; $R^6$=9-$OCH_3$; $X^-$=$ClO_4^-$).

(c)

A reaction mixture containing 9-methoxy-thiazolo[3,2-b]isoquinolinium perchlorate (1 g; 3.17 mmol) and 1,1-di(methyl)-2,2-di(ethoxy)ethylene (1.5 g; 10.4 mmol) in 20 ml of acetonitrile was heated to reflux under argon with stirring for 24 h. The reaction mixture was concentrated in vacuo, the residue was passed through a silica gel column (methylene chloride/methanol, 9:1) to afford 800 mg (57%) of 11,11-diethoxy-12,12-dimethyl-9-methoxy-5,10-ethano-5,10-dihydrothiazolo[3,2-b]isoquinolinium perchlorate (Formula I: A=thiazolo; $R^1$=H; $R^2$=$R^3$=$CH_3$; $R^4$=$R^5$=$OC_2H_5$; $R^6$=9-$OCH_3$; $X^-$=$ClO_4^-$).

(d)

11,11-Diethoxy-12,12-dimethyl-9-methoxy-5,10-ethano-5,10-dihydrothiazolo[3,2-b]isoquinolinium perchlorate (700 mg, 1.63 mmol) was converted to the corresponding chloride salt by passing the salt through Dowex® 1x2-200-($Cl^-$). The salt was recrystallized from methylene chloride/ether to afford 280 mg (54%) of 11,11-diethoxy-12,12-dimethyl-9-methoxy-5,10-ethano-5,10-dihydrothiazolo[3,2-b]isoquinolinium chloride (Formula I: A=thiazolo; $R^1$=H; $R^2$=$R^3$=$CH_3$; $R^4$=$R^5$=$OC_2H_5$; $R^6$=9-$OCH_3$; $X^-$=$Cl^-$), m.p. >130° C.(d).

EXAMPLE 7

(a)

To a solution of n-butyllithium (6.28 g, 98 mmol, 2M in hexane) in 160 ml of ether under argon at −78° C. was added dropwise in 1 h a solution of 1-methylimidazole (7.8 g, 0.095 mol). The mixture was stirred at −78° C. for 1 h to which was added a solution of DMF (6.9 g, 95 mmol) in 40 ml of ether. The mixture was stirred for 1 h at −78° C., then at −15° C. for 18 h. The reaction mixture was then extracted with 4N HCl (4×20 ml), the aqueous layers were combined, cooled in an ice-bath, and neutralized with sodium bicarbonate solution. The aqueous layer was extracted with ether (4×35 ml), the organic layer was dried over sodium sulfate and concentrated in vacuo to afford 11.1 g of 1-methylimidazolyl-2-carboxaldehyde.

(b)

A mixture of 1-methyl-thiazolyl-2-carboxaldehyde (1.5 g, 13.6 mmol), 60.46 g(0.41 mol) of triethyl orthoformate, 100 ml of ethanol and 25.8 g (0.136 mol) of p-toluenesulfonic acid monohydrate under argon in a 3 neck-flask equipped with a Dean-Stark trap was refluxed for 6 h separating the water/ethanol formed. The mixture was cooled to room temperature, neutralized with an ice-cold 10% sodium carbonate solution, filtered, and the filtrate was concentrated in vacuo. The residue was concentrated to remove triethyl orthoformate, the resulting residue was dissolved in ether, filtered, and washed with water. The ether solution was dried over sodium sulfate and concentrated in vacuo to afford 8 g (31.9%) of 2-(diethoxymethyl-1-methylimidazole (Formula V: A=1-methylimidazole; Y=$CH(OC_2H_5)_2$.

(c)

A reaction mixture of 8 g (43 mmol) of 2-(diethoxymethyl-1-methyl-imidazole and 7.44 g (43 mmol) of benzyl bromide was stirred at room temperature overnight. The mixture was triturated with ethyl acetate and decanted to afford 15.1 g (98.3%) of 3-benzyl-2-(diethoxymethyl)-1-methylimidazolium bromide (Formula VI: A=1-methylimidazole; Y=$CH(OC_2H_5)_2$; $R^1$=$R^6$=H; $Z^-$=$Br^-$).

(d)

A mixture of 3-benzyl-2-(diethoxymethyl)-1-methylimidazolium bromide (15 g, 42.25 mmol) and 100 ml of 48% HBr was heated on a steam-bath with stirring for 6 h. The mixture was cooled to room temperature, concentrated in vacuo, and the resulting residue was redissolved in water. The aqueous solution was filtered and the filtrate was treated with sodium perchlorate. The precipitated product was filtered, washed with water, ether and dried in vacuo to afford 4.1 g (34%) of 1-methylimidazo[1,2-b]isoquinolin-4-ium perchlorate (Formula II: A=1-methylimidazo; $R^1$=$R^6$=H; $X^-$=$ClO_4^-$)

(e)

A reaction mixture containing 1-methylimidazo[1,2-b]isoquinolin-4-ium perchlorate (1 g; 3.54 mmol) and 1,1-di(methyl)-2,2-di(ethoxy)ethylene (1 g; 6.94 mmol), and 100 mg of calcium carbonate in 15 ml of acetonitrile was heated to reflux under argon with stirring for 3 days then was placed in a high pressure apparatus at 10 Kbar for 24 hours. The reaction mixture was concentrated in vacuo, the residue was passed through a silica gel column (methylene chloride/methanol, 9:1) to afford 800 mg (53%) of 11,11-diethoxy-12,12-dimethyl-5,10-ethano-5,10-dihydro-1-methylimidazo[1,2-b]isoquinolin-4-ium perchlorate (Formula I: A=1-methylimidazo; $R^1$=$R^6$=H; $R^2$=$R^3$=$CH_3$; $R^4$=$R^5$=$OC_2H_5$; $X^-$=$ClO_4^-$).

(f)

11,11-Diethoxy-12,12-dimethyl-5,10-ethano-5,10-dihydro-1-methylimidazo[1,2-b]isoquinolin-4-ium perchlorate (800 mg, 1.87 mmol) was converted to the corresponding chloride salt by passing the salt through Dowex® 1x2-200-($Cl^-$). The salt was recrystallized from methylene chloride/ether to afford 370 mg (44.2%) of 11,11-diethoxy-12,12-dimethyl-5,10-ethano-5,10-dihydro-1-methylimidazo[1,2-b]isoquinolin-4-ium chloride (Formula I: A=1-methylimidazo; $R^1$=$R^6$=H; $R^2$=$R^3$=$CH_3$; $R^4$=$R^5$=$OC_2H_5$; $X^-$=$Cl^-$), m.p. 122° C.

EXAMPLE 8

(a)

A reaction mixture containing 1-benzylimidazo[1,2-b]isoquinolin-4-ium perchlorate (2.4 g; 6.7 mmol) and 1,1-di(methyl)-2,2-di(ethoxy)ethylene (1.92 g; 13.33 mmol) in 50 ml of acetonitrile was heated to reflux under argon with stirring for 24 h. After adding 1,1-di(methyl)-2,2-di(ethoxy) ethylene (1 g), the mixture was heated to reflux for an additional 24 h. The reaction mixture was cooled, concentrated in vacuo, and the residue (3.1 g) was passed through a silica gel column (methylene chloride/methanol, 20:1) to afford 1.2 g (35%) of 11,11-diethoxy-12,12-dimethyl-5,10-ethano-5,10-dihydro-1-benzylimidazo[1,2-b]isoquinolin-4-ium perchlorate (Formula I: A=1-benzylimidazo; $R^1$=$R^6$=H; $R^2$=$R^3$=$CH_3$; $R^4$=$R^5$=$OC_2H_5$; $X^-$=$ClO_4^-$).

(b)

11,11-Diethoxy-12,12-dimethyl-5,10-ethano-5,10-dihydro-1-benzylimidazo[1,2-b]isoquinolin-4-ium perchlorate (1.1 g, 2.19 mmol) was converted to the corresponding chloride salt by passing the salt through Dowex® 1x2-200 ($Cl^-$). The salt (1 g) was recrystallized from methylene chloride/acetonitrile/ethyl acetate to afford 670 mg (70%) of 11,11-diethoxy-12,12-dimethyl-5,10-ethano-5,10-dihydro-1-benzylimidazo[1,2-b]isoquinolin-4-ium chloride (Formula I: A=1-benzylimidazo; $R^1$=$R^6$=H; $R^2$=$R^3$=$CH_3$; $R^4$=$R^5$=$OC_2H_5$; $X^-$=$Cl^-$), m.p. 215°–217° C.

EXAMPLE 9

(a)

A reaction mixture containing 1-benzylimidazo[1,2-b]isoquinolin-4-ium perchlorate (2 g; 5.58 mmol) and 1,1-di(phenyl)-ethylene (2.01 g; 11.16 mmol) in 35 ml of nitromethane was heated to reflux under argon with stirring for 2 days. After adding 1,1-di(methyl)-2,2-di(ethoxy)ethylene (2 ml), the mixture was heated to reflux for an additional 2 days. The reaction mixture was cooled, concentrated in vacuo, the residue was triturated with ether, and the resulting solid was washed with ether to yield 3.8 g of a solid. The product was purified by a silica gel column (methylene chloride/methanol, 20:1) to afford 2.7 g (89.8%) of 11,11-diphenyl-5,10-ethano-5,10-dihydro-1-benzylimidazo[1,2-b]isoquinolin-4-ium perchlorate (Formula I: A=1-benzylimidazo; $R^1$=$R^2$=$R^3$=$R^6$=H; $R^4$=$R^5$=phenyl; $X^-$=$ClO_4^-$), as a yellow foam..

(b)

11,11-Diphenyl-5,10-ethano-5,10-dihydro-1-benzylimidazo[1,2-b]isoquinolin-4-ium perchlorate (2.7 g, 5.01 mmol) was converted to the corresponding chloride salt by passing the salt through Dowex® 1x2-200-($Cl^-$). The salt (1.9 g) was recrystallized from isopropanol/methylene chloride/ether to afford 1.6 g (67.2%) of 11,11-diphenyl-5,10-ethano-5,10-dihydro-1-benzylimidazo[1,2.-b]isoquinolin-4-ium chloride (Formula I: A=1-benzylimidazo; $R^1$=$R^2$=$R^3$=$R^6$=H; $R^4$=$R^5$=phenyl; $X^-$=$Cl^-$), m.p. 175°–177° C.

EXAMPLE 10

(a)

A reaction mixture containing 1-methyl-1,2,4-triazolo[1,2-b]isoquinolin-4-ium perchlorate (2 g; 7.05 mmol) and 1,1-di(methyl)-2,2-di(ethoxy)ethylene (3 g; 21.16 mmol) in 50 ml of acetonitrile was heated to reflux under argon with stirring for 6 h. The reaction mixture was concentrated in vacuo, the residue was triturated with ether, and decanted. The resulting dark residue was dried in vacuo to afford 3.1 g of 11,11-diethoxy-12,12-dimethyl-5,10-ethano-5,10-dihydro-1-methyl-1,2,4-triazolo[1,2-b]isoquinolin-4-ium perchlorate (Formula I: A=1-methyl-1,2,4-triazolo; $R^1$=$R^6$=H; $R^2$=$R^3$=$CH_3$; $R^4$=$R^5$=$OC_2H_5$; $X^-$=$ClO_4^-$).

(b)

11,11-Diethoxy-12,12-dimethyl-5,10-ethano-5,10-dihydro-1-methyl-1.2,4-triazolo[1,2-b]isoquinolin-4-ium perchlorate (3.1 g, 7.25 mmol) was converted to the corresponding chloride salt by passing the salt through Dowex® 1x2-200-($Cl^-$). The salt (2.2 g, 88%) was recrystallized from methylene chloride/ether to afford 2 g (73.4%) of 11,11-diethoxy-12,12-dimethyl-5,10-ethano-5,10-dihydro-1-methyl-1,2,4-triazolo[1,2-b]isoquinolin-4-ium chloride (Formula I: A=1-methyl-1,2,4-triazolo; $R^1$=$R^6$=H; $R^2$=$R^3$=$CH_3$; $R^4$=$R^5$=$OC_2H_5$; $X^-$=$Cl^-$), m.p. 188°–190° C.

EXAMPLE 11

(a)

To a stirred solution of sodium methoxide (from 5 g of sodium, 0.218 mol) in 120 ml of methanol under argon was added 1,2,4-triazole (15 g, 0.217 mol) at 0° C. and then 30.9 g (0.217 mol) of methyl iodide, and the mixture was stirred at room temperature for 24 h. The solvent was concencentrated in vacuo, the residue was extracted with 80 ml of hot benzene and then with chloroform (3×80 ml). Upon removal of the solvent in vacuo, 25.4 g of a white gum was isolated and the gum was dissolved in methylene chloride, filtered, and the filtrate was concentrated to yield an oil. The oil was distilled (80°–90° C./10–15 mm) to afford 10.5 g (58%) of 1-methyl-1,2,4-triazole.

(b)

To a solution of 11 g (0.13) of 1-methyl-1,2,4-triazole in 200 ml of ether at −78° C. under argon was added n-butyllithium (8.5 g, 0.13 mol, 2.5M in hexane) in a 30 min period and the mixture was stirred at −78° C. for 2 h, and then 9.5 g (0.13 mol) of DMF in 25 ml of ether was added. The mixture was slowly warmed to 0° C. with stirring overnight. The mixture was quenched with Dowex® 50x2-200 ($H^+$) in methanol, stirred at 0° C. for 30 min, and then 100 g of silica gel was added to the mixture. The whole suspension was packed on a silica gel column with methylene chloride and the eluent was concentrated to afford 15.1 g of 1-methyl-1,2,4-triazolyl-5-carboxaldehyde. Additional chromatographic purification on silica gel (methylene chloride/ether, 9:1) yielded 6.8 g of the desired aldehyde.

(c)

A mixture of 1-methyl-1,2,4-triazolyl-5-carboxaldehyde (3.1 g, 28 mmol), 3.1 ml (56 mmol) of ethylene glycol, 250 ml of toluene and 1.4 g (14 mmol) of p-toluenesulfonic acid monohydrate under argon in a 3 neck-flask equipped with a Dean-Stark trap was refluxed for 24 h, separating the water formed. The mixture was cooled to room temperature, and poured into an ice-cold 10% sodium carbonate solution. The aqueous layer was extracted with ether, the combined organic layer was washed with brine and dried over sodium sulfate, and concentrated in vacuo to afford 2.3 g (53%) of 5-(1,3-dioxolan-2-yl)-1-methyl-1,2,4-triazole (Formula V: A=1-methyl-1,2,4-triazole; Y=5-(1,3-dioxolan-2-yl).

(d)

A reaction mixture of 2.3 g (14.83 mmol) of 5-(1,3-dioxolan-2-yl)-1-methyl-1,2,4-triazole and 2.53 g (14.83 mmol) of benzyl bromide was heated on a steam-bath with stirring for 48 h. The mixture was cooled to room temperature, triturated with ethyl acetate and decanted to afford 3.1 g (64.1%) of 4-benzyl-5-(1,3-dioxolan-2-yl)-1-methyl-1,2,4-triazolium bromide (Formula VI: A=1-methyl-1,2,4-triazolo; Y=5-(1,3-dioxolan-2-yl); $R^1=R^6=H$; $Z^-=Br^-$).

(e)

A mixture of 4-benzyl-5-(1,3-dioxolan-2-yl)-1-methyl-1,2,4-triazolium bromide (6.5 g, 20 mmol) and 70 g of polyphosphoric acid was heated in an oil bath at 100°–110° C. with stirring for 5 h. The mixture was cooled to room temperature, poured into ice-water, stirred for 1 h, and filtered through a pad of solka floc®. The residue was washed with water and the combined filtrate was treated with an excess sodium perchlorate solution. The precipitated product was filtered, washed with water, and dried in vacuo to afford 4 g (70%) of 1-methyl-1,2,4-triazolo[1,2-b]isoquinolin-4-ium perchlorate (Formula II: A=1-methyl-1,2,4-triazolo; $R^1=R^6=H$; $X^-=ClO_4^-$).

(f)

A reaction mixture containing 1-methyl-1,2,4-triazolo[1,2-b]isoquinolin-4-ium perchlorate (1.5 g; 5.3 mmol) and 1,1-di(phenyl)ethylene (1.9 g; 10.6 mmol) in 25 ml of nitromethane was heated to reflux under argon with stirring for 24 h. The reaction mixture was concentrated in vacuo, the solid residue was triturated with ether and decanted to afford 2.6 g of 11,11-diphenyl-5,10-ethano-5,10-dihydro-1-methyl-1,2,4-triazolo[1,2-b]isoquinolin-4-ium perchlorate (Formula I: A=1-methyl-1,2,4-triazolo; $R^1=R^2=R^3=R^6=H$; $R^4=R^5$=phenyl; $X^-=ClO_4^-$).

(g)

11,11-Diphenyl-5,10-ethano-5,10-dihydrol-methyl-1,2,4-triazolo[1,2-b]isoquinolin-4-ium perchlorate (2.5 g, 5.34 mmol) was converted to the corresponding chloride salt by passing the salt through Dowex® 1x2-200-$Cl^-$. The salt was recrystallized from methylene chloride/ether to afford 1.5 g (69%) of 11,11-diphenyl-5,10-ethano-5,10-dihydro-1-methyl-1,2,4-triazolo[1,2-b]isoquinolin-4-ium chloride (Formula I: A=1-methyl-1,2,4-triazolo; $R^1=R^2=R^3=R^6=H$; $R^4=R^5$=phenyl; $X^-=Cl^-$), m.p. 178°–180° C.(d).

EXAMPLE 12

(a)

To a solution of n-butyllithium (7.04 g, 0.1 mol, 2M in hexane) in 200 ml of ether under argon at −78° C. was added dropwise in 1 h a solution of 1-benzylimidazole (15.82 g, 0.1 mol) in 100 ml of ether. The mixture was stirred at −78° C. for 1 h, followed by addition of a solution of DMF (10.96 g, 0.15 mol) in 15 ml of ether. The mixture was stirred for 1 h at −78° C., then at −15° C. for 18 h. The reaction mixture was then extracted with 4N HCl (4×20 ml), the aqueous layers were combined, cooled in an ice-bath, and neutralizrd with sodium bicarbonate solution. The aqueous layer was extracted with chloroform (4×100 ml), the organic layer was dried over sodium sulfate and concentrated in vacuo, and the residue was chromatographed on silica gel (methylene chloride) to afford 10.1 g (52%) of 1-benzyl-2-imidazolylcarboxaldehyde.

(b)

A mixture of 1-benzyl-2-imidazolylcarboxaldehyde (10.1 g, 54.3 mmol), 6 ml (108.6 mmol) of ethylene glycol, 400 ml of toluene and 1.4 g (13.57 mmol) of p-toluenesulfonic acid monohydrate under argon in a 3 neck-flask equipped with a Dean-Stark trap was refluxed for 24 h separating the water formed. The mixture was cooled to room temperature, was poured into an ice-cold 10% sodium carbonate solution. The aqueous layer was extracted wiith ether (3×150 ml), the combined organic layer was washed with brine and dried over sodium sulfate, and concentrated in vacuo to afford 12.5 g of 2-(1.3-dioxolan-2-yl)-1-benzylimidazole (Formula V: A=1-benzylimidazole; Y=2-(1,3-dioxolan-2-yl); $R^1=R^6=H$).

(c)

A reaction mixture of 12.5 g (54 mmol) of 2-(1,3-dioxolan-2-yl)-1-benzylimidazole and 9.3 g (54 mmol) of benzyl bromide was heated on a steam-bath with stirring for ¼ h and the resulting mixture was stirred at room temperature overnight. The mixture was triturated with ether/ethyl acetate and filtered to afford 17.3 g (79.8%) of 3-benzyl-2-(1,3-dioxolan-2-yl)-1-benzylimidazolium bromide (Formula VI: A=1-benzylimidazole; Y=2-(1,3,-dioxolan-2-yl); $R^1=R^6=H$; $Z^-=Br^-$).

(d)

A mixture of 3-benzyl-2-(1,3-dioxolan-2-yl)-1-benzylimidazolium bromide (14 g,35 mmol) and 140 g of polyphosphoric acid was heated in an oil bath at 100°–110° C. with stirring for 5 h. The mixture was cooled to room temperature, poured into ice-water and stirred for 1 h, and then filtered through a filter pad of Solka Floc®. The residue was washed with water and the combined filtrate was treated with an excess sodium perchlorate solution. The precipitated product was filtered, washed with water, and dried in vacuo to afford 9.95 g of a gum. The above gum was dissolved in acetonitrile, filtered, the filtrate was concentrated in vacuo, and the resulting residue was triturated with ethyl acetate/ether (1:1) to yield a yellow solid. The yellow solid was filtered, washed with ether, and dried in vacuo to afford 7.3 g (58.1%) of 1-benzylimidazo[1,2-b]isoquinolin-4-ium perchlorate (Formula II: A=1-benzylimidazo; $R^1=R^6=H$; $X^-=ClO_4^-$).

(e)

A reaction mixture containing 1-benzylimidazo[1,2-b]isoquinolin-4-ium perchlorate (2 g; 5.58 mmol) and 1,1-di(3-furyl)ethylene (1.1 g; 6.87 mmol) in 25 ml of acetonitrile was heated to reflux under argon with stirring for 24 h. The reaction mixture was concentrated in vacuo, the residue was passed through a silica gel column (methylene chloride/methanol, 9:1) to afford 2.1 g (55.8%) of 11,11-di(3-furyl)-5,10-ethano-5,10-dihydro-1-benzylimidazo[1,2-b]isoquinolin-4-ium perchlorate (Formula I: A=1-benzylimidazo; $R^1=R^2=R^3=R^6=H$; $R^4=R^5$=3-furyl; $X^-=ClO_4^-$).

(f)

11,11-Di(3-furyl )-5,10-ethano-5,10-dihydro-1-benzylimidazo[1,2-b]isoquinolin-4-ium perchlorate (2 g, 3.86 mmol) was converted to the corresponding chloride salt by passing the salt through Dowex® 1x2-200-($Cl^-$). The solvent was concentrated to afford 1.65 g (94%) of 11,11-di(3-furyl)-5,10-ethano-5,10-dihydro-1-benzylimidazo[1,2-b]isoquinolin-4-ium chloride (Formula I: A=1-benzylimidazo; $R^1$=$R^2$=$R^3$=$R^6$=H; $R^4$=$R^5$=3-furyl; $X^-$=$Cl^-$).

EXAMPLE 13

(a)

A reaction mixture containing 1-methylimidazo[1,2-b]isoquinolin-4-ium perchlorate (4 g; 14.16 mmol) in 50 ml of acetonitrile and 1,1-di(3-furyl)ethylene (3.4 g; 21.24 mmol) in 10 ml of ethanol was heated to reflux under argon with stirring for 24 h. The reaction mixture was concentrated in vacuo, the residue was passed through a silica gel column (methylene chloride/ethyl acetate/methanol, 7:2:1) to afford 5.3 g (84%) of 11,11-di(3-furyl )-5,10-ethano-5,10-dihydro-1-methylimidazo[1,2-b]isoquinolin-4-ium perchlorate (Formula I: A=1-methylimidazo; $R^1$=$R^2$=$R^3$=$R^6$=H; $R^4$=$R^5$=3-furyl; $X^-$=$ClO_4^-$).

(b)

11,11-di(3-furyl)-5,10-ethano-5,10-dihydro-1-methylimidazo[1,2b]isoquinolin-4-ium perchlorate (5.3 g, 11.97 mmol) was converted to the corresponding chloride salt by passing the salt through Dowex® 1x2-200-($Cl^-$). The solvent was concentrated in vacuo and the salt was dried in vacuo to afford 3.4 g (75.1%) of 11,11-di(3-furyl)-5,10-ethano-5,10-dihydro-1-methylimidazo[1,2-b]isoquinolin-4-ium chloride (Formula I: A=1-methylimidazo; $R^1$=$R^2$=$R^3$=$R^6$=H; $R^4$=$R^5$=3-furyl; $X^-$=$Cl^-$).

EXAMPLE 14

(a)

To a solution of 19.6 g (0.236 mol) of 1-methyl-1,2,4-triazole in 350 ml of ether at −78° C. under argon was added n-butyllithium (91 ml, 0.236 mol, 2.5M in hexane) within a 30 min period and the mixture was stirred at −78° C. for 2 h, and followed with the addition of 17.3 g (0.236 mol) of DMF in 45 ml of ether. The mixture was slowly warmed to 0° C., and was stirred at 0° C. for 2 hours, then 25 g of silica gel was added to the mixture. The whole suspension was packed on a silica column with methylene chloride and the eluent (methylene chloride/ether, 4:1) was concentrated to afford 17.75 g (67.7%) of 1-methyl-1,2,4-triazolyl-5-carboxaldehyde, as a yellow oil.

(b)

A reaction mixture of 6.27 g (40.4 mmol) of 5-(1,3-dioxolan-2-yl)-1-methyl-1,2,4-triazole and 6.91 g (40.4 mmol) of benzyl bromide was heated on a steam-bath with stirring for 4 h. The mixture was cooled to room temperature, triturated with ether and decanted to afford 11.3 g (85.7%) of 4-benzyl-5-(1,3-dioxolan-2-yl)-1-methyl-1,2,4-triazolium bromide (Formula VI: A=1-methyl-1,2,4-triazole; Y=5-(1,3-dioxolan-2-yl); $R^1$=$R^6$=H; $Z^-$=$Br^-$).

(c)

A mixture of 4-benzyl-5-(1,3-dioxolan-2-yl)-1-methyl-1,2,4-triazolium bromide (11.3 g, 30 mmol) and 110 g of polyphosphoric acid was heated at 100°–110° C. with stirring for 3 h. The mixture was cooled to room temperature, poured into ice-water, stirred for 1 h, and filtered. The residue was washed with water and the combined filtrate was treated with an excess sodium perchlorate (15 g). The precipitated product was filtered, washed with water, and dried in vacuo to afford 1.715 g (17.46%) of 1-methyl-1,2,4-triazolo[1,2-b]isoquinolin-4-ium perchlorate (Formula II: A=1-methyl-1,2,4-triazolo; $R^1$=$R^6$=H; $X^-$=$ClO_4^-$).

(d) and (e)

A reaction mixture containing 1-methyl-1,2,4-triazolo[1,2-b]isoquinolin-4-ium perchlorate (1.715 g; 7.28 mmol) and 1,1-di(3-furyl)ethylene (1.3 g; 8 mmol) in 20 ml of nitromethane was heated to reflux under argon with stirring for 6 h. The reaction mixture was concentrated in vacuo, the solid residue was triturated with ether and methylene chloride/ether, and decanted to afford 11,11-di(3-furyl)-5,10-ethano-5,10-dihydro-1-methyl-1,2,4-triazolo[1,2-b]isoquinolin-4-ium perchlorate (Formula I: A=1-methyl-1,2,4-triazolo; $R^1$=$R^2$=$R^3$=$R^6$=H; $R^4$=$R^5$=3-furyl; $X^-$=$ClO_4^-$; Example 14 (d)). The perchlorate salt was converted to the corresponding chloride by passing the salt through Dowex® 1x2-200-$Cl^-$. The salt was recrystallized from isopropanol/acetonitrile to afford 1.022 g (37%) of 11,11-di(3-furyl)-5,10-ethano-5,10-dihydro-1-methyl-1,2,4-triazolo[1,2-b]isoquinolin-4-ium chloride (Formula I: A=1-methyl-1,2,4-triazolo; $R^1$=$R^2$=$R^3$=$R^6$=H; $R^4$=$R^5$=3-furyl; $X^-$=$Cl^-$; Example 14 (e)), m.p. 222°–224° C.(d).

EXAMPLE 15

(a)

To a solution of n-butyllithium (96 ml, 0.24 mol, 2.5M in hexane) in 200 ml of ether under argon at −78° C. was added dropwise in 1 h a solution of 4-methylthiazole (20 g, 0.0202 mol) in 100 ml of ether. The mixture was stirred at −78° C. for 1 h, and then a solution of N-formyl-morpholine (22 ml, 0.22 mol) in 120 ml of ether was added within 15 min. The mixture was stirred for 1 h at −78° C., then at 0°—5° C. overnight. The reaction mixture was then extracted with 4N HCl (4×40 ml), the aqueous layers were combined, cooled in an ice-bath, and neutralized with sodium bicarbonate solution (pH 9). The aqueous layer was extracted with ether (4×80 ml), the organic layer was dried over magnesium sulfate and concentrated in vacuo. The residue was distilled (80°–85° C./25 mm) to afford 8.6 g (33.5%) of 4-methyl-2-thiazolylcarboxaldehyde.

(b)

A mixture of 4-methyl-2-thiazolylcarboxaldehyde (8.6 g, 67.7 mmol), 8.4 g (135 mmol) of ethylene glycol, 150 ml of toluene and 3.2 g (11.06 mmol) of p-toluenesulfonic acid under argon in a 3 neck-flask equipped with a Dean-Stark trap was refluxed for 6 h separating the water formed. The mixture was cooled to room temperature, and poured into an ice-cold saturated sodium carbonate solution (100 ml). The aqueous layer was extracted wiith ether, the combined organic layer was washed with brine and dried over magnesium sulfate, and concentrated in vacuo to afford 15 g (crude) of 2-(1,3-dioxolan-2-yl)-4-methylthiazole (Formula V: A=4-methylthiazole; Y=2-(1,3-dioxolan-2-yl).

(c)

A reaction mixture of 2-(1,3-dioxolan-2-yl)-4-methylthiazole and benzyl bromide was heated on a steam-bath at 60° C. with stirring for 4 h. The mixture was cooled to room temperature, triturated with ether and filtered to afford 3-benzyl-2-(1,3-dioxalan-2-yl)-4-methylthiazolium bromide (Formula VI: A=4-methylthiazole; Y=2-(1,3-dioxolan-2-yl; $R^1$=$R^6$=H; $Z^-$=$Br^-$).

(d)

To 25 g of polyphosphoric acid heated at 110° C. was added with stirring 3-benzyl-2-(1,3-dioxolan-2-yl)-4-methylthiazolium bromide (2.31 7 g, 7.9 mmol) and the mixture was stirred for 3 h. The mixture was cooled to room temperature, poured into 200 ml of water, and treated with 3 g of sodium perchlorate. The precipitated product was filtered, washed with water, ether and dried in vacuo to afford 1.5 g (64%) of 3-methylthiazolo[3,2-b]isoquinolinium perchlorate (Formula II: A=3-methylthiazolo; $R^1$=$R^6$=H; $X^-$=$ClO_4^-$).

(e) and (f)

A reaction mixture containing 3-methylthiazolo[3,2-b] isoquinolinium perchlorate (1.5 g; 5 mmol) and 1,1-di(3-furyl)ethylene (1.6 g; 10 mmol) in 25 ml of ethanol was heated to reflux under argon with stirring overnight. The reaction mixture was cooled, and filtered to yield a brown solid (1.91 g) which was passed through a silica column (methylene chloride/acetonitrile, 7:3) to afford 1.8 g (78.4%) of 11,11-di(3-furyl)-5,10-ethano-5,10-dihydro-3-methylthiazolo[3,2-b]isoquinolinium perchlorate (Formula I: A=3-methylthiazole; $R^1$=$R^2$=$R^3$=$R^6$=H; $R^4$=$R^5$=3-furyl; $X^-$=$ClO_4^-$; Example 15 (e)), as a solid. The perchlorate salt was converted to the corresponding chloride by passing the salt through Dowex® 1x2-200-$Cl^-$ (38 g). The salt was dissolved in acetonitrile, washed with water, the organic layer was concentrated in vacuo and the residue was dried to afford 1.19 g (54%) of 11,11-di(3-furyl)-5,10-ethano-5,10-dihydro-3-methylthiazolo[3,2-b]isoquinolinium chloride (Formula I: A=3-methylthiazole; $R^1$=$R^2$=$R^3$=$R^6$=H; $R^4$=$R^5$=3-furyl; $X^-$=$Cl^-$; Example 15 (f)).

EXAMPLE 16

(a)

To a solution of n-butyllithium (24 ml, 0.06 mol, 2.5M in hexane) in 50 ml of ether under argon at −78° C. was added dropwise a solution of 5-methylthiazole (5 g, 0.05 mol) in 25 ml of ether. The mixture was stirred at −78° C. for 1 h, and then a solution of N-formyl-morpholine (5.5 ml 0.055 mol) in 30 ml of ether was added within 15 min. The mixture was stirred for 1 h at −78° C., then at 0°—5° C. overnight. The reaction mixture was then extracted with 4N HCl (4×10 ml), the aqueous layers were combined, cooled in an ice-bath, and neutralized with sodium bicarbonate solution (pH 9). The aqueous layer was extracted with ether (4×20 ml), the organic layer was dried over magnesium sulfate and concentrated in vacuo. The residue was dried in vacuo to afford 4.5 g (70.8%%) of 5-methyl-2-thiazolylcarboxaldehyde.

(b)

A mixture of 5-methyl-2-thiazolylcarboxaldehyde (4.5 g, 34.5 mmol), 3.9 ml (70 mmol) of ethylene glycol, 100 ml of toluene and 1.6 g (8.75 mmol) of p-toluenesulfonic acid monohydrate under argon in a 3 neck-flask equipped with a Dean-Stark trap was refluxed overnight separating the water formed. The mixture was cooled to room temperature, and poured into an ice-cold saturated sodium carbonate solution (100 ml). The aqueous layer was extracted with ether, the combined organic layer was washed with brine and dried over magnesium sulfate, and concentrated in vacuo to afford 5.4 g (crude) of 2-(1,3-dioxolan-2-yl)-5-methylthiazole (Formula V: A=5-methylthiazole; Y=2-(1,3-dioxolan-2-yl).

(c)

A reaction mixture of the above 2-(1,3-dioxolan-2-yl)-5-methylthiazole (5.4 g) and benzyl bromide (15 ml) was stirred for 3 days at room temperature. The solid mixture was triturated in 100 ml of ether and decanted. After adding 20 ml of 48% HBr solution, the mixture was heated at 120° C. for four hours, cooled to room temperature, and the resulting solution was diluted with water, and treated with sodium perchlorate. The precipitated brown solid was filtered and dried in vacuo to afford 4.25 g (28.3%) of 2-methylthiazolo[3,2-b]isoquinolinium perchlorate (Formula II: A=2-methylthiazolo; $R^1$=$R^6$=H; $X^-$=$ClO_4^-$).

(d) and (e)

A reaction mixture containing 2-methylthiazolo[3,2-b] isoquinolinium perchlorate (1.25 g; 4.35 mmol) and 1,1-di(3-furyl)ethylene (0.72 g; 4.5 mmol) in 40 ml of ethanol and 5 ml of acetonitrile was heated to reflux under argon with stirring overnight. The reaction mixture was cooled, and concentrated in vacuo to yield a solid which was passed through a flash chromatography on silica column (methylene chloride/ethyl acetate/methanol, 7:2:1) to afford 11,11-di(3-furyl)-5,10-ethano-5,10-dihydro-2-methylthiazolo[3,2-b] isoquinolinium perchlorate (Formula I: A=2-methylthiazolo; $R^1$=$R^2$=$R^3$=$R^6$=H; $R^4$=$R^5$=3-furyl; $X^-$=$ClO_4^-$; Example 16 (d)). The perchlorate salt was converted to the corresponding chloride by passing the salt through Dowex® 1x2-200-$Cl^-$. The eluent was filtered, extracted with ether (½ volume), and the aqueous layer was concentrated in vacuo (40° C.) to afford 0.4 g (24%) of 11,11-di(3-furyl)-5,10-ethano-5,10-dihydro-2-methylthiazolo[3,2-b]isoquinolinium chloride (Formula I: A=2-methylthiazolo; $R^1$=$R^2$=$R^3$=$R^6$=H; $R^4$=$R^5$=3-furyl; $X^-$=$Cl^-$; Example 16 (e)).

EXAMPLE 17

11,11-Di(3-furyl)-5,10-ethano-5,10-dihydrothiazolo[3,2-b]isoquinolinium perchlorate (0.5 g) was dissolved 10 ml of acetic acid and 90 ml of water with stirring, and then bromine was added dropwise until a yellow-brown color persisted. The mixture was cooled, filtered, the filtrate was concentrated in vacuo. The resulting residue was dissolved in water, treated with sodium perchlorate, and the solid was filtered and dried to yield 60 mg of 11,11-di-(5-oxo-4,5-dihydro-3-furyl)-5,10-ethano-5,10-dihydrothiazolo[3,2-b] isoquinolinium perchlorate (Formula I: A=thiazolo; $R^1$=$R^2$=$R^3$=$R^6$=H; $R^4$=$R^5$=(5-oxo-4,5-dihydro-3-furyl); $X^-$=$ClO_4^-$). The filtrate was extracted with methylene chloride (4×50 ml) and chloroform (1×100 ml), and the combined organic layer was dried over sodium sulfate and concentrated in vacuo, and the resulting residue was passed through a flash chromatography silica gel column (methylene chloride/ethyl acetate/methanol, 7:2:1) to afford an additional 50 mg of 11,11-di-[(5-oxo)-4,5-dihydro-3-furyl]-5,10-ethano-5,10-dihydrothiazolo[3,2-b]isoquinolinium perchlorate.

EXAMPLE 18

(a)

To a mixture of pyrazole (88.3 g, 1.297 mol) and formalin (116 ml, 33%, 1.4 mol) in 450 ml of ethanol at 0° C. was added pyrrolidine (101.2 g, 1.425 mol) dropwise, and the mixture was heated to reflux under nitrogen for 5 h. The reaction mixture was cooled, and concentrated in vacuo. The residue was distilled (57°–58° C./0.05 mm) to afford 140 g (55.12%) of 1-(1-pyrrolidinomethyl)-pyrazole.

(b)

To a solution of 1-(1-pyrrolidinomethyl)-pyrazole (91.5 g, 0.606 mol) in 1.7 L of THF at −78° C. under argon was added 24.5 ml (0.612 mol) of 2.5M n-butyllithium over a 30 min period The mixture was stirred at −78° C. for 1.5 h, DMPU (155 g, 1.21 mol) was added and stirred for 30 min, and then 38.4 g (0.288 mol) of N-methyl,N-methoxy-urethane in 100 ml of THF was added. The resulting reaction mixture was slowly warmed to room temperature and stirred overnight. The mixture was quenched with 500 ml of water, stirred, and the aqueous layer was extracted with ethyl acetate (2×500 ml). The combined organic layer was dried over sodium sulfate and concentrated in vacuo. The residue was dissolved in dioxane/ether (1 L, 2:1), and 500 ml of 6N HCl was added and stirred under nitrogen for 20 h. The aqueous layer was saturated with NaCl, filtered, and extracted with THF/ether (2:1; 6×300 ml). The combined organic layer was concentrated in vacuo, the residue (53 g) was triturated in 500 ml of chloroform/hexane (1:1), filtered, washed with ether and dried to afford 22 g (47.2%) of 1,1-di(5-pyrazolyl)ketone.

(c)

To a suspension of 2.9 g (0.12 mol) of NaH in 100 ml of DMF at 0° C. was added 8 g (0.05 mol) of 1,1-di-(5-pyrazolyl)-ketone in 100 ml of DMF, and the mixture was stirred at room temperature for ½ h and then at 50° C. for 30 min. To the above mixture was added p-methoxybenzyl chloride (25 g, 0.16 mol) and the mixture was stirred at 50° C. under nitrogen for 3 h. The mixture was stirred at room temperature overnight, concentrated in vacuo, the residue was dissoved in 500 ml of ethyl acetate, and washed with water (3×100 ml) and brine. The organic layer was dried over sodium sulfate, concentrated in vacuo, and the residue was purified by chromatography on silica (ethyl acetate/hexane/M.D.C, 5:3:2) to afford 13 g (43.2%) of 1,1-di-[(1-p-methoxybenzyl-pyrazol-3-yl)-ketone.

(d)

To a solution of potassium t-butoxide (5.8 g, 0.051 mol) in 500 ml of THF at 0° C. was added methyltriphenylphosphonium bromide (17.5 g; 0.048 mol) under nitrogen and the mixture was stirred at room temperature for 2 h. To the above mixture was added 1,1-di-[(1-p-methoxybenzyl)-pyrazol-3-yl)-ketone (13 g, 0.032 mol) in 250 ml of THF and the mixture was stirred at room temperature under nitrogen for 1 h. The above mixture was quenched with acetone, filtered through a filter pad, and the residue was washed with ether. The combined organic filtrate was concentrated in vacuo and the residue was purified by chromatography on silica (ether/hexane 1:1) to afford 4 g (30.7%) of 1,1-di-[(1-p-methoxybenzyl)-pyrazol-3-yl)ethylene (Formula III: $R^2$=$R^3$=H; $R^4$=$R^5$=1-p-methoxybenzyl-3-pyrazolyl).

(e)

A reaction mixture containing thiazolo[3,2-b]isoquinolinium perchlorate (2.4 g; 8.4 mmol) and 1,1-di-[(1-p-methoxybenzyl)-pyrazol-3-yl)ethylene (4 g; 0.01 mol) in 125 ml of ethanol and 25 ml of acetonitrile was refluxed for 12 h under nitrogen. The reaction mixture was cooled to room temperature, the solid product was filtered, washed with ether, and dried in vacuo to afford 4.65 g (81.6%) of 11,11-di-[(1-p-methoxybenzyl)-pyrazol-3-yl)]-5,10-ethano-5,10-dihydrothiazolo[3,2-b]isoquinolinium perchlorate (Formula I: A=thiazolo; $R^1$=$R^2$=$R^3$=$R^6$=H; $R^4$=$R^5$=1-p-methoxybenzyl-3-pyrazolyl; $X^-$=$ClO_4^-$).

(f)

A solution of 4.4 g (6.4 mmol) of 11,11-1,1-di-[(1-p-methoxybenzyl)-pyrazol-3-yl)]-5,10-ethano-5,10-dihydrothiazolo[3,2-b]isoquinolinium perchlorate in 100 ml of trifluoroacetic acid was refluxed under nitrogen for 30 h. The reaction mixture was concentrated in vacuo, the residue was triturated in 600 ml of 50% methanol in water, the solid product was filtered, washed with 250 ml of methanol/water (1:1). The resulting solid was purified by chromatography on silica (ethyl acetate/PAW 1:1) to afford 2.4 g (87.27%) of 11,11-di-(pyrazol-5-yl)-5,10-ethano-5,10-dihydrothiazolo[3,2-b]isoquinolinium acetate (Formula I: A=thiazolo; $R^1$=$R^2$=$R^3$=$R^6$=H; $R^4$=$R^5$=5-pyrazolyl; $X^-$=$OAc^-$).

(g)

11,11-Di-(pyrazol-5-yl)-5,10-ethano-5,10-dihydrothiazolo[3,2-b]isoquinolinium acetate (2.4 g, 5.6 mmol) was converted to the corresponding chloride salt by passing the acetate salt through Dowex® 1x2-200-$Cl^-$ (200 g) to afford 1.5 g of 11,11-di-(pyrazol-5-yl)-5,10-ethano-5,10-dihydrothiazolo[3,2-b]isoquinolinium chloride. The above solid was redissolved in 25 ml of water, treated with 10% sodium perchlorate solution, the resulting solid was triturated in warm methanol and filtered to afford 1.5 g (60%) of 11,11-di-(pyrazol-5-yl)-5,10-ethano-5,10-dihydrothiazolo[3,2-b]isoquinolinium perchlorate (Formula I: A=thiazolo; $R^1$=$R^2$=$R^3$=$R^6$=H; $R^4$=$R^5$=5-pyrazolyl; $X^-$=$ClO_4^-$).

(h)

11,11-1,1-Di-(pyrazol-5-yl)-5,10-ethano-5,10-dihydrothiazolo[3,2-b]isoquinolinium perchlorate (1.5 g) was converted to the corresponding chloride salt by passing the perchlorate salt through Dowex® 1x2-200-$Cl^-$ (200 g) to afford 0.9 g (70.3%) of 11,11-di-(pyrazol-5-yl)-5,10-ethano-5,10-dihydrothiazolo[3,2-b]isoquinolinium chloride (Formula I: A=thiazolo; $R^1$=$R^2$=$R^3$=$R^6$=H; $R^4$=$R^5$=5-pyrazolyl; $X^-$=$Cl^-$), as a solid.

EXAMPLE 19

(a)

To a solution of 10.88 g (0.16 mol) of imidazole in 150 ml of dry DMF at 0° C. under argon was added 6.4 g (0.16 mol) of 60% NaH, and the mixture was stirred at 0° C. for 30 min and then at room temperature for 1 h. The mixture was cooled to 0° C., and 25 g (0.16 mol) of p-methoxybenzyl chloride was added, and the mixture was stirred at room temperature for 24 h. The reaction mixture was concentrated in vacuo and the residue was partitioned between methylene chloride and water. The organic layer was dried over sodium sulfate, concentrated in vacuo to yield 35.6 g of a crude product which was purified by chromatography on silica (methylene chloride/methanol 9:1) to afford 25.3 g (84.2%) of 1-(p-methoxybenzyl)-imidazole.

(b)

To a solution of 18.8 g (0.1 mol) of 1-(p-methoxybenzyl)-imidazole in 200 ml of dry THF/ether (1:1) at −78° C. under argon was added n-butyllithium (7.04 g, 44 ml, 0.11 mol, 2.5M in hexane) in 100 ml of ether and the mixture was stirred at −78° C. for 2 h, and then 10.96 g (0.15 mol) of DMF in 20 ml of ether was added. The mixture was slowly warmed to 0° C. with stirring. The mixture was quenched with Dowex® 50x2-200 ($H^+$) in methanol, stirred at 0° C. for 30 min, and then 100 g of silica gel was added to the mixture. The whole suspension was packed on a silica gel column with methylene chloride and the eluent was concentrated to afford 16.3 g of 1-(p-methoxybenzyl)imidazolyl-2-carboxaldehyde.

(c)

To a mixture of 11.2 g (0.06 mol) of o-bromobenzyl alcohol in 200 ml of ether cooled to −40° C. was added in portions 48 ml (0.12 mol) of 2.5M n-butyllithium in hexane followed by 6.97 g (0.061 mol) of TMEDA and the reaction mixture was slowly warmed to room temperature and stirred for 2 hours. The above reaction mixture was cooled to −20° C., 16.7 g (0.075 mol) of 1-(p-methoxy-benzyl)imidazolyl-2-carboxaldehyde in 25 ml of ether was added, and the resulting reaction mixture was allowed to warm to room temperature. After 1 hour, ammonium chloride solution was added to the mixture. The diol was extracted with ethyl acetate, dried over sodium sulfate, and the solvent was removed in vacuo. The residue was purified by chromatography on silica gel column (methylene chloride/methanol, 9:1) to afford 9 g of 2-[1-hydroxy-(2'-hydroxymethyl)-benzyl]-1-(p-methoxybenzyl)imidazole (Formula IX: A=1-(p-methoxybenzyl)imidazole; $R^1$=$R^6$=H).

(d)

A mixture of 3.24 g (10 mmol) of 2-[1-hydroxy-(2'-hydroxymethyl)-benzyl]-1-(p-methoxybenzyl)imidazole and 25 ml of $POCl_3$ was refluxed with stirring for 48 h. The resulting solution was cooled, poured into ice, and the resulting solution was treated with a warm potassium hexafluorophosphate solution, the resulting solid was filtered, washed with ether, and dried to afford 2.9 g (66%) of 1-(p-methoxybenzyl)-imidazo[1,2-b]isoquinolin-4-ium hexafluorophosphate (Formula II: A=1-(p-methoxybenzyl) imidazo; $R^1$=$R^6$=H; $X^-$=$PF_6^-$).

(e)

A reaction mixture containing 1-(p-methoxybenzyl)-imidazo[1,2-b]isoquinolin-4-ium hexafluorophosphate (2.8 g; 6.54 mmol) and 1,1-di(3-furyl)ethylene (1.55 g; 9.675 mmol) in 70 ml of acetonitrile was heated to reflux under argon with stirring for 48 h. The reaction mixture was concentrated in vacuo, the residue was triturated with ether and decanted. Crude residue was passed through a silica gel column (methylene chloride/ethyl acetate/methanol, 7:2:1) to afford 2.16 g (67%) of 11,11,-di(3-furyl)-5,10-ethano-5,10-dihydro-1-(p-methoxybenzyl)-imidazo[1,2-b]isoquinolin-4-ium hexafluorophosphate (Formula I: A=1-(p-methoxybenzyl)imidazo; $R^1$=$R^2$=$R^3$=$R^6$=H; $R^4$=$R^5$=3-furyl; $X^-$=$PF_6^-$)

(f)

11,11-Di(3-furyl)-5,10-ethano-5,10-dihydro-1-(p-methoxybenzyl)imidazo[1,2-b]isoquinolin-4-ium hexafluorophosphate(2.6 g, 4.4 mmol) was converted to the corresponding chloride salt by passing the salt through Dowex® 1x2-200-($Cl^-$). The solvent was concentrated, the residue was redissolved in warm water, filtered, and the filtrate was concentrated in vacuo to afford 1.5 g of 11,11-di(3-furyl)-5,10-ethano-5,10-dihydro-1-(p-methoxybenzyl)imidazo[1,2-b]isoquinolin-4-ium chloride (Formula I: A=1-(p-methoxybenzyl)imidazo; $R^1$=$R^2$=$R^3$=$R^6$=H; $R^4$=$R^5$=3-furyl; $X^-$=$Cl^-$).

EXAMPLE 20

To a solution of 1-indanone (23.78 g, 0.18 mol) in 250 ml of ether at 0° C. was added dropwise over 30 min., 100 ml of phenyllithium in ether (1.8M in ether) and the mixture was allowed to warm to room temperature and stirred 1 h. The reaction mixture was poured into a cold saturated ammonium chloride solution, extracted with ether (2×200 ml), and the combined organic layer was washed with brine and dried over sodium sulfate. The organic solvent was removed under reduced pressure, 70 ml of 20% sulfuric acid in acetic acid was added to the residue and stirred 2 min. To the above solution water (100 ml) and ether (3×200 ml) were added, The organic layer was washed with sodium bicarbonate solution, dried over sodium sulfate, filtered, and concentrated. Toluene (300 ml) was added to the residue and the mixture was distilled (azeotropic removal of acetic acid) to afford a brown oil. The brown oil was purified by chromatography (silica; (2:1 hexane/methylene chloride)) to afford 15.58 g (45.82%) of 1-phenyl-indene as a colorless oil. In addition 11 g of 1-phenyl-1-acetoxy-indane was isolated as a by-product.

EXAMPLE 21

(a)

To a solution of 3-(4-methoxyphenyl)propionic acid (50.34 g, 0.279 mol) in 500 ml of methylene chloride cooled to 0° C. was added slowly at 0° C. 30.5 ml (0.418 mol) of thionyl chloride, the mixture was stirred 10 h, at room temperature and the solvent was removed in vacuo. The residue was dissolved in 1000 ml of methylene chloride, cooled to 0° C., and 40.92 g (0.306 mol) of aluminum chloride was added in small portions and the resulting mixture was sitrred at room temperature for 1 h. The above mixture was poured onto ice, the resulting mixture was filtered through celite, and the aqueous layer was extracted with methylene chloride (2×200 ml). The combined organic layer was dried over sodium sulfate, concentrated in vacuo, and the residue was extracted with hexane to afford 40 g (88%) of 6-methoxy-1-indanone.

(b)

To a solution of 20 g (0.123 mol) of 6-methoxy-1-indanone in 500 ml of ether cooled to −20° C. was added 72 ml (0.129 mol) of 1.8M phenyllithium in cyclohexane/ether and the mixture was stirred at room temperature for 1 h. An additional (10 ml) phenyllithium solution was added and stirred at room temperature for 1 h. To the reaction mixture was added saturated ammonium chloride solution and the resulting mixture was extracted with ethyl acetate (3×250 ml), and the organic layer was dried over sodium sulfate and concentrated in vacuo to afford 32.3 g crude (contains solvent) of 6-methoxyl-1-phenyl-indan-1ol.

(c)

To 1.5 L of toluene was added 32 g (0.133 mol) of 6-methoxy-1-phenyl-indan-1-ol and 100 mg of p-toluenesulfonic acid and the mixture was placed on a Rotovap® and the solvent was distilled in vacuo (40 mm) until a brown oil residue was obtained. The brown oil was chromatographed (silica, 1:1 hexane/methylene chloride) to afford 17.47 g (60.2%) of 1-phenyl-6-methoxy-indene as a pale yellow oil.

EXAMPLE 22

(a)

Dihydrocoumarin (35 g, 0.236 mol) was added to 62.9 g (0.472 mol) of aluminum chloride and the mixture was heated in an oil-bath at 200° C. for 2.5 h with stirring The reaction mixture was cooled, poured into ice (300 g), 300 ml of methylene chloride added to the mixture, cooled, and 400 ml of methylene chloride was added. The mixture was filtered and the solid residue was dissolved in hot methanol, filtered, and the filtrate was cooled to afford 14.5 g (41%) of 4-hydroxy-indan-1-one.

(b)

To a mixture of 4-hydroxy-indan-1-one (14.5 g, 0.0979 mol) and 27.08 g (0.195 mol) of potassium carbonate was added 500 ml of acetone and 48.7 ml (0.78 mol) of methanol with stirring and the resulting mixture was heated to reflux for 4 h, cooled, and allowed to stand at room temperature for 10 h. The above mixture was filtered concentrated under vacuo, the solid residue was dissolved in methanol, heated and filtered. The filtrate was concentrated to a volume of 100 ml, cooled and filtered to afford 12.6 g (79%) of 4-methoxy-indan-1-one.

(c)

To a solution of 9.38 g (0.057 mol) of 4-methoxy-1-indanone in 250 ml of ether cooled to 0° C. was added dropwise over 5 min 33.72 ml (0.0607 mol) of 1.8M phenyllithium in cyclohexane/ether and the mixture was stirred at room temperature for 1 h. An additional (10 ml) phenyllithium solution was added and stirred at room temperature for 1 h. To the reaction mixture was added saturated ammonium chloride solution and the resulting mixture was extracted with ethyl acetate (3×100 ml), and the organic layer was washed with brine, dried over sodium sulfate and concentrated in vacuo to afford 14.3 g of crude 4-methoxy-1-phenyl-indan-1-ol which was used directly in the next step without further purification.

(d)

To 1 L of toluene was added 14 g (0.058 mol) of 4-methoxy-1-phenyl-indan-1-ol and100 mg of p-toluenesulfonic acid and the mixture was placed on a Rotovap® and the solvent was distilled in vacuo (40 mm) until an oil residue was obtained. The oil was chromatographed (silica, 1:1 hexane/methylene chloride followed by ether) to afford 8.6 g (60.2%) of 1-phenyl-4-methoxy-indene as a pale red oil.

EXAMPLE 23

(a)

To a solution of 13.17 ml (0.104 mol) of 3-bromoanisole in 150 ml of ether cooled to −78° C. was added 10.4 ml (0.104 mol) of 10M n-butyllithium in hexane and the mixture was allowed to warm to room temperature (10 min). The above mixture was cooled to −20° C. and 12.5 g (0.094 mol) of indanone in 20 ml of THF was added and the mixture was allowed to warm to room temperature, and then stirred for 1 h. To the mixture was added saturated ammonium chloride solution and the resulting mixture was extracted with ethyl acetate (3×50 ml), and the organic layer was washed with brine, dried over sodium sulfate and concentrated in vacuo to afford 23.3 g of crude 1(3-methoxy)-phenyl-indan-1ol, as a brown oil, which was used directly in the next step without further purification.

(b)

To a mixture of 23 g (0.095 mol) of 1-(3-methoxyphenyl)-indan-1-ol and 100 mg of p-toluene sulfonicacid was added 1 L of toluene and the mixture was placed on a Rotovap® and the solvent was distilled in vacuo (40 mm) until an oil residue was obtained. The oil was chromatographed (silica, 1:1 hexane/methylene chloride) to afford 17.0 g (80.1%) of 1-(3-methoxyphenyl)-indene as a pale yellow oil.

EXAMPLE 24

(a)

To a solution of 2.7 ml (0.027 mol) of 10M n-butyllithium in hexane in 70 ml of ether cooled to −78° C. was added 4 g (0.027 mol) of 3-bromofuran and the mixture was stirred for 15 min. To the above cooled mixture was added 3.17 g (0.024 mol) of indanone in 10 ml of THF and the mixture was allowed to warm to room temperature, and then stirred for 20 min. To the mixture was added saturated ammonium chloride solution and the resulting mixture was extracted with ethyl acetate (3×100 ml), and the organic layer was washed with brine, dried over sodium sulfate and concentrated in vacuo to afford 5 g of crude 1-(3-furyl)-indan-1ol, as an orange oil, which was used directly in the next step.

(b)

To a mixture of 5 g (0.024 mol) of 1-(3-furyl)-indan-1-ol in 500 ml of toluene was added 50 mg of p-toluenesulfonic acid and the mixture was placed on a Rotovap® and the solvent was distilled in vacuo (40 mm) until a residue was obtained. The residue was chromatographed (silica, 1:1 hexane/methylene chloride) to afford 2.7 g (61.3%) of 1-(3-furyl)-indene as a clear oil.

EXAMPLE 25

To a solution of 10.2 ml (0.102 mol) of 10M n-butyllithium in hexane in 200 ml of ether cooled to −78° C. was added dropwise 15 g (0.102 mol) of 3-bromofuran and the mixture was stirred for 15 min. To the above cooled mixture was added 12.61 g (0.092 mol) of 4,5,6,7-tetrahydrobenzofuran-7-one in 50 ml of THF and the mixture was allowed to warm to room temperature, and then stirred for 15 min. To the mixture was added saturated ammonium chloride solution and the resulting mixture was extracted with ethyl acetate (3×100 ml), and the organic layer was washed with brine, dried over sodium sulfate and concentrated in vacuo to afford 16.3 g (86%) of 4,5,6,7-tetrahydro-7-(3-furyl)-benzofuran-7-ol, a red oil.

To a mixture of 16.3 g of the above alcohol in 400 ml of toluene was added 100 mg of p-toluenesulfonic acid and the mixture was placed on a Rotovap® and the solvent was distilled in vacuo (40 mm/50° C.) until a brown-red residue was obtained yielding 14.3 g (96%) of 4,5-dihydro-7-(3-furyl)-benzofuran as a red oil.

EXAMPLE 26

(a)

To a solution of 4 ml (0.04 mol) of 10M n-butyllithium in hexane cooled to −78° C. was added 3.59 ml (0.04 mol) of 3-bromofuran in 100 ml of ether and the mixture was stirred for 10 min. To the above cooled solution was added 5.49 g (0.036 mol) 4,5,6,7-tetrahydro-3-methyl-benzisoxazol-7-one and the mixture was allowed to warm to room temperature, and then stirred for 1 h. To the mixture was added saturated ammonium chloride solution and the resulting mixture was extracted with ethyl acetate (3×100 ml), and the organic layer was washed with brine, dried over sodium sulfate and concentrated in vacuo to afford 7.6 g (96%) of 7-(3-furyl)-3-methyl-4,5,6,7-tetrahydrobenzisoxazol-7-ol, as a brown oil.

(b)

To a mixture of 7.6 g (0.034 mol) of 7-(3-furyl)-3-methyl-4,5,6,7-tetrahydro-benzisoxazol-7-ol in 300 ml of toluene was added 100 mg of p-toluenesulfonic acid and the mixture was placed on a Rotovap, and the solvent was distilled in vacuo (80° C.) until an oil residue was obtained. Toluene (200 ml) was added to the above residue, the mixture was placed on Rotovap, and the solvent was distilled in vacuo to complete the reaction. The oil was chromatographed (silica, 1:1 hexane/methylene chloride) to afford 3.36 g (95%) of 7-(3-furyl)-3-methyl-4,5-dihydrobenzisoxazole, (Formula III: $R^2$=H;

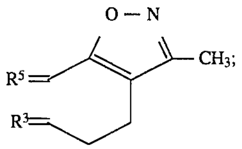

$R^4$=3-furanyl) as a clear oil.

EXAMPLE 27

To a solution of 20 g (0.147 mol) of 4,5,6,7-tetrahydrobenzofuryl-4-one was added 31.8 ml of triethylorthoformate, 34.5 ml of ethanol, and 100 mg of p-toluenesulfonic acid and the mixture was stirred for 16 h. To the above mixture was added 2 g. of potassium carbonate, and the mixture was stirred for 5 min, filtered and concentrated in vacuo to afford 24.1 g of a 2:1 mixture of 4-ethoxy-6,7-dihydrobenzofuran and starting 4,5,6,7-tetrahydro-benzofuryl-4-one.

EXAMPLE 28

(a)

To a solution of 11.1 g (0.0939 mol) of benzofuran in 150 ml of ether cooled to −20° C. was added a solution of 9.39 ml (0.0939 mol) 10M n-butyllithium in hexane, and the mixture was allowed to warm to 0° C. and stirred for 30 min. The mixture was cooled to −78° C. and 10.6 g (0.078 mol) of 4,5,6,7-tetrahydrobenzofuran-4-one in 20 ml of ether was added dropwise and the mixture was allowed to warm to room temperature, and then stirred for 1 h. To the mixture was added saturated ammonium chloride solution and the resulting mixture was extracted with ethyl acetate (3×100 ml). The organic layer was washed with brine, dried over sodium sulfate and concentrated in vacuo to afford 19.3 g (97%) of 4,5,6,7-tetrahydro-4-(2-benzofuryl)-benzofuran-7-ol, an oil which crystallized on standing as a yellow solid.

(b)

To a mixture of 19.3 g of 4,5,6,7-tetrahydro-4-(2-benzofuryl)-benzofuran-7-ol in 400 ml of toluene was added 100 mg of p-toluene sulfonic acid, and the mixture was placed on a Rotovap®, and the solvent was distilled in vacuo (60° C.) until a residue was obtained. The residue was chromatographed on silica (hexane/methylene chloride 1.5:1) to afford 15.3 g (86%) of 6,7-dihydro-4-(2-benzofuryl)-benzofuran, (Formula III: $R^2$=H;

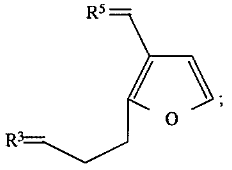

$R^4$=2-benzofuryl) as an orange oil.

EXAMPLE 29

(a)

To a solution of furan-3-carboxylic acid (26 g, 0.23 mol) in 250 ml of toluene was added 24.15 ml (0.276 mol) of oxalyl chloride and 1 drop of pyridine and the mixture was heated on a steam-bath for 2 h. The mixture was cooled to room temperature, N,O-dimethylhydroxamine hydrochloride (24.66 g, 0.253 mol), 4-dimethylaminopyridine (DMAP, 1.2 g, 0.01 mol), and 600 ml of methylene chloride were added. The mixture was cooled to 0° C., 50.1 ml of pyridine in 50 ml of methylene chloride was added slowly, the mixture was allowed to warm to room temperature (3 h), and 2 g of N,O-dimethylhydroxamine hydrochloride and 1 g of 4-dimethylaminopyridine (DMAP) were added. The resulting mixture was stirred for 12 h. The above mixture was cooled to 0° C., filtered, and the filtrate was washed with 3N HCl, brine, dried over sodium sulfate, and concentrated in vacuo to yield 14 g (39%) of 3-(N-methyl-N-methoxycarbamoyl)furan.

(b)

To a solution of 3-(N-methyl-N-methoxycarbamoyl)furan (14 g, 0.09 mol) in 150 ml of THF cooled to −78° C. was added in portions 36.1 ml (0.108 mol) of 3M methylmagnesium bromide in ether and the mixture was allowed to warm to room temperature, and then stirred for 30 min. To the above mixture was added a cold 2N HCl (100 ml) and the aqueous layer was extracted with ether (3×100 ml), the combined organic layer was washed with brine, dried over sodium sulfate, and concentrated in vacuo to yield a pale-yellow oil. The above oil was chromatographed on silica (methylene chloride/hexane 2:1) to afford 6.95 g (70.2%) of 1-(3-furyl)-1-propanone as a colorless oil which crystallized as a white solid.

(c)

To a stirring mixture of 1-(3-furyl)-1-propanone (6.75 g, 0.0612 mol) in 150 ml of methylene chloride was added TEOF (13.2 ml, 0.079 mol) with stirring followed by 100 mg of p-toluenesulfonic acid and the resulting mixture was stirred for 126 h. Potassium carbonate (2 g) was added to the above reaction mixture, stirred for 10 min, filtered, and concentrated in vacuo. The residue was distilled (35 mm, 82°–85° C.) to afford 2.5 g of (29%) 1-(3-furyl)-1-ethoxyethylene (Formula III: $R^2$=$R^3$=H; $R^4$=$CH_3CH_2O$; $R^5$=3-furanyl), as a clear oil.

EXAMPLE 30

(a)

A mixture of (2,5-dimethyl-3-acetyl)-furan (12.5 g, 0.09 mol), 300 mg of p-toluenesulfonic acid, 21.2 ml (0.35 mol) of ethanol, and 29.9 ml (0.18 mol) of triethylorthoformate in 250 ml of methylene chloride was stirred at room temperature 72 h, then 1 g of potassium carbonate, was added. The mixture was stirred for 5 min, filtered, and concentrated in vacuo. The residue was distilled (40–45 mm/115°–125° C.) to afford 7.94 g (53.2%) of 1-[(2,5-dimethyl)-3-furyl]-1-ethoxy-ethylene, (Formula III: $R^2$=$R^3$=H; $R^4$=$CH_3CH_2O$; $R^5$=2,5-dimethyl-3-furanyl); as a clear oil.

EXAMPLE 31

(a)

To a solution of 3,3-difurylmethanone (3 g, 0.0185 mol) in 50 ml of THF cooled to 0° C. was added 7.4 ml (0.022 mol) of 3M ethylmagnesium bromide in ether and the mixture was allowed to warm to room temperature, and then stirred for 30 min. To the above mixture was added ammonium chloride solution, the mixture was extracted with ethyl acetate, and the organic layer was dried over sodium sulfate and concentrated in vacuo to yield 2.5 g (70.4%) of 1,1-(di-3-furyl)-propanol, a brown oil.

(b)

A mixture of 1,1-(di-3-furyl)-propanol (2.95 g. 0.0153 mol) and 150 ml of p-toluenesulfonic acid in toluene was heated to 70° C. and the mixture was distilled to remove toluene in vacuo to yield a pale-yellow oil. The above oil was chromatographed on silica (hexane/methylene chloride 3:1) to afford 500 mg (18.7%) of 1,1-(di-3-furyl)-2-methylethylene, (Formula III: $R^2$=$CH_3$; $R^3$=H; $R^4$=$R^5$=3-furyl), as a clear oil.

EXAMPLE 32

(a)

To a solution of 7.22 ml (0.0722 mol) of 10M n-butyllithium in hexane in 150 ml of ether cooled to −78° C. was added 10.62 g (0.0722 mol) of 3-bromofuran and the mixture was stirred for 15 min. To the above cooled mixture was added 10 g (0.0656 mol) of 4,5,6,7-tetrahydro-thianaphthen-4-one in 25 ml of THF and the mixture was allowed to warm to room temperature, and then stirred. To the mixture was added saturated ammonium chloride solution and the resulting mixture was extracted with ethyl acetate (3×100 ml), and the organic layer was washed with brine, dried over sodium sulfate and concentrated in vacuo to afford 13.6 g (94.2%) of 4-(3-furyl)-4,5,6,7-tetrahydro-thianaphthen-4-ol, as a brown oil.

(b)

To a mixture of 13.6 g (0.0618 mol) of 4-(3-furyl)-4,5,6,7-tetrahydrothianaphthen-4-ol in 250 ml of toluene was added 600 mg of p-toluenesulfonic acid. The mixture was placed on a Rotovap® and toluene was distilled in vacuo (60° C.) until a residue was obtained. The residue was chromatographed (silica, 3:1 hexane/methylene chloride) to afford 11.6 g (92.9%) of 4-(3-furyl)-6,7-dihydrothianaphthene as a pale-yellow oil.

EXAMPLE 33

To a solution of bromobenzene (100 g, 0.63 mol) in 300 ml of dichloroethane cooled to 0° C. was added 169.6 g (1.27 mol) of aluminum chloride. The mixture was stirred (1 min), and 37.6 g (0.378 mol) of 1,1,1-trichloroethane in 50 ml of dichloroethene was added and stirred at 0° C. for 1 h. The above mixture was diluted with 500 g of ice, basified with 30% sodium hydroxide solution, filtered, the aqueous layer was extracted with methylene chloride (2×500 ml), and the combined organic layer was dried over sodium sulfate and concentrated in vacuo to yield a brown oil. The brown oil was crystallized from hexane (2×150 ml) to afford 10.5 g of 1,1-di(4-bromo)phenyl-ethylene (Formula III: $R^2$=$R^3$=H; $R^4$=$R^5$=4-bromophenyl) as a white solid. The mother liquor was concentrated in vacuo and chromatographed on silica (hexane) to yield 18.5 g (total 29 g, 27%) of an additional white solid.

EXAMPLE 34

To a suspension of methyltriphenylphosphonium bromide (17.83 g; 49.9 mmol) in 150 ml of ether was added at −10° 10M n-butyllithium in hexane (4.99 ml; 49.4 mmol) and the mixture was allowed to stir at room temperature for 1 hour. To the above mixture was added 10 g (47 mmol) of 1,1-di(p-tolyl)ketone in 50 ml of ether/tetrahydrofuran (3:2), and the mixture was heated to reflux for 2 h, cooled, 20 ml of THF added, and filtered. To the filtrate was added ammonium chloride solution and the resulting mixture was extracted with ethyl acetate (2×), dried over sodium sulfate and concentrated in vacuo to yield a yellow oil. The oil was purified through flash chromatography on silica (hexane/methylene chloride 3:1) to afford 9.3 g (95.1%) of 1,1-di(p-tolyl)ethylene (Formula III: $R^2$=$R^3$=H; $R^4$=$R^5$=4-$CH_3$phenyl).

EXAMPLE 35

To a suspension of methyltriphenylphosphonium bromide (42.94; 120 mmol) in 500 ml of ether was added at −30° C. 10M n-butyllithium in hexane (12.02 ml; 120 mmol) and the mixture was allowed to stir at room temperature for 1 h. To the above mixture was added 25 g (114.5 mmol) of 1,1-di(p-fluorophenyl)-ketone in 100 ml of THF during a 5 min period, and the mixture was allowed to reflux for 2 h, cooled, and filtered. To the filtrate was added ammonium chloride solution and the resulting mixture was extracted with ethyl acetate (2×), dried over sodium sulfate and concentrated in vacuo to yield red oil which was purified through flash chromatography on silica (hexane/methylene chloride 5:1) to afford 21.2 g (85.7%) of 1,1-di(p-fluorophenyl)ethylene (Formula III: $R^2$=$R^3$-H; $R^4$=$R^5$=4-F-phenyl).

EXAMPLE 36

(a)

To a suspension of methyltriphenylphosphonium bromide (7.14 g; 20 mmol) in ether was added at 0° C. n-butyllithium in hexane (8 ml; 20 mmol) and the mixture was allowed to stir at room temperature for 1 h.. To the above mixture was added 2.8 g (8.2 mmol) of 1,1-di(m-methoxyphenyl)ketone in ether and the mixture was stirred for 10 minutes. The above reaction mixture was quenched with acetone (5 ml), stirred for 5 minutes, filtered, and the filtrate was concentrated in vacuo. The residue was purified by chromatography on silica eluting with hexane/ether (9:1) to afford 3.6 g (90%) of 1,1-di(m-methoxy-phenyl)ethylene (Formula III: $R^2=R^3=H$; $R^4=R^5=3-CH_3O$-phenyl).

EXAMPLE 37

A suspension of methyltriphenylphosphonium bromide (3.25 g; 9.05 mmol) in 100 ml of ether was added at 0° C. n-butyllithium in hexane (3.7 ml; 9.05 mmol) and the mixture was allowed to stir at room temperature for 1 h. To the above mixture was added 2.8 g (8.2 mmol) of 1,1-di(m-bromophenyl)ketone in 30 ml of tetrahydrofuran and the mixture was stirred for 10 min. The above reaction mixture was quenched with acetone (5 ml), stirred for 5 minutes, filtered, and the filtrate was concentrated in vacuo. The residue in hexane/methylene chloride (3:1) was purified by chromatography on silica eluting with hexane to afford 2.2 g (78.6%) of 1,1-di(m-bromophenyl)ethylene (Formula III: $R^2=R^3=H$; $R^4=R^5=3$-Br-phenyl).

EXAMPLE 38

(a)

To a solution of 3-bromopyridine (9.84 g,0.062 mol) in 300 ml of ether cooled to −78° C. was added n-butyllithium (1.6M, 41 ml, 0.066 mol) and stirred for 30 min. N-Methyl, N-methoxy-urethane (3.76 g, 0.028 mol) in 20 ml of ether was added in 10 min, the mixture was stirred (−78° C.) for 1 h, allowed to warm to room temperature and stirred for 2 h. The reaction mixture was quenched with 6N HCl (100 ml) and stirred. The aqueous layer was basified with 10% NaOH solution, extracted with ethyl acetate (2×) and methylene dichloride. The organic layer was dried over sodium sulfate, concentrated in vacuo, and the residue was purified by chromatography on silica (ethyl acetate, 10% methanol/ethyl acetate) to afford 1,7 g (33%) of di-(3-pyridyl)ketone.

(b)

To a suspension of methyl-triphenylphosphonium bromide (3.6 g; 10.1 mmol) in 50 ml of ether was added at −20° C. 2.5M n-butyllithium in hexane (4 ml; 10.1 mmol) and the mixture was allowed to stir at room temperature for 1 hour. To the above mixture was added 1.7 g (9.3 mmol) of 1,1-di(3-pyridyl)ketone in 50 ml of tetrahydrofuran and the mixture was stirred at room temperature for 2 h. Ammonium chloride solution and ethyl acetate (250 ml) were added to the above mixture, the organic phase was washed with water, brine, dried, and concentrated in vacuo. The residue was purified by chromatography on silica (ether/hexane/methanol, 5:4,5:0.5) to afford 0.9 g (52.9%) of 1,1-di(3-pyridyl)-ethylene (Formula III: $R^2=R^3=H$; $R^4=R^5=3$-pyridyl).

EXAMPLE 39

To a suspension of methyl-triphenylphosphonium bromide (31.36 g; 0.0878 mol) in 500 ml of ether was added at −30° C. 10M n-butyllithium in hexane (8.78 ml; 0.078 mol), the mixture was allowed to warm and then stirred at room temperature for 1 hour. To the above mixture was added 21 g (0.0836 mol) of 1,1-di(p-chlorophenyl)ketone in 50 ml of tetrahydrofuran and the mixture was refluxed for 1 h, cooled, and filtered. The above filtrate was added to ammonium chloride solution, the resulting mixture was extracted with ethyl acetate (3×150 ml), the organic layer was dried over sodium sulfate, and concentrated in vacuo to afford 22 g of crude 1,1-di-(p-chlorophenyl)ethylene, (Formula III: $R^2=R^3=H$; $R^4=R^5=4$-Cl-phenyl), as an off-white solid.

EXAMPLE 40

To a suspension of methyltriphenylphosphonium bromide (30.96 g; 0.0825 mol) in ether (500 ml) was added at −30° C. 10M n-butyllithium in hexane (8.66 ml; 0.0866 mol) and the mixture was allowed to stir at room temperature for 1 hour. To the above mixture was added 20 g (0.0825 mol) of 1,1-di(p-methoxyphenyl)-ketone in 50 ml of THF over a 4 min period and the mixture was refluxed for 1 h and cooled. The above reaction mixture was filtered and ammonium chloride solution was added to the filtrate. The above mixture was extracted with ethyl acetate (3×150 ml), the organic layer was dried over sodium sulfate and concentrated in vacuo to afford 20.2 g of crude 1,1di-(p-methoxyphenyl)ethylene (Formula III: $R^2=R^3=H$; $R^4=R^5=4-OCH_3$-phenyl).

EXAMPLE 41

To a suspension of methyltriphenylphosphonium bromide (29.44 g; 0.0785 mol) in 500 ml of ether was added at −30° C. 10M n-butyllithium in hexane (8.24 ml; 0.0824 mol) and the mixture was allowed to warm and stir at room temperature for 1 hour. To the above mixture was added 25 g (0.0785 mol) of 3,3'-bis(trifluoromethyl)benzophenone in 50 ml of tetrahydrofuran and the mixture was refluxed for 1 h, cooled, filtered, and concentrated in vacuo. The above residue was chromatographed on silica (hexane:$CH_2Cl_2$, 2:1) to afford 22.3 g (89.9%) of 1,1-di-(m-trifluoromethylphenyl)ethylene (Formula III: $R^2=R^3=H$; $R^4=R^5=3-CF_3$-phenyl), as a yellow liquid.

EXAMPLE 42

(a)

To a mixture of 12.7 g (0.099 mol) of 2-thienylcarboxylic acid, 8.33 g (0.099 mol) of thiophene, and 34.9 ml of Amberlyst-15 in 250 ml of nitromethane was added 34.9 ml (0.247 mol) of trifluoroacetic acid at room temperature and stirred for 14 h. The reaction mixture was filtered, the filtrate was concentrated in vacuo, and a green oil residue was chromatographed on silica (hexane/methylene chloride 1:1) to afford 8 g (41.6%) of di-(2-thienyl)ketone, as white needles.

(b)

To a suspension of methyltriphenylphosphonium bromide (15.46 g; 16.8 mmol) in 250 ml of ether was added at −30° C. 10M n-butyllithium in hexane (4.3 ml; 43 mmol) and the mixture was stirred at room temperature for 1 h. To the above mixture was added 8 g (41 mmol) of 1,1-di(2- thienyl)ketone in 30 ml of tetrahydrofuran over a 3 min period, the mixture was stirred at room temperature for 1 h and then filtered. To the above reaction mixture was added saturated ammonium chloride solution, and the mixture was extracted with ethyl acetate (3×100 ml). The organic layer was separated, washed with water, dried, and concentrated in vacuo to afford 1,1-di(2-thienyl)ethylene (Formula III: $R^2$=$R^3$=H; $R^4$=$R^5$=2-thienyl), as a brown oil.

EXAMPLE 43

(a)

To a suspension of 4-bromopyridine hydrochloride (21 g,0.1 mol) in 300 ml of ether was added 200 ml of saturated sodium bicarbonate and the mixture was stirred for 5 min. The organic layer was dried over sodium sulfate and concentrated in vacuo to afford 15.1 g (89.3%) of 4-bromopyridine.

(b)

To a solution of n-butyllithium (2.5M, 39 ml, 0.096 mol) in 300 ml of ether cooled to −75° C. was added 4-bromopyridine (15.1 g,0.095 mol) in 100 ml of ether at such a rate to maintain the internal temperature below −50° C. The resulting mixture was stirred at −75° C. for 15 min., and N-methyl,N-methoxy-urethane (5.8 g, 0.043 mol) in 25 ml of ether was added over a 20 min period, and the mixtue was warmed to room temperature and then stirred for 2 h. The mixture was quenched with 300 ml of water and the layers were separated. The organic layer was extracted with 6N HCl solution, and the aqueous layer was basified with 10% NaOH solution. The basic solution was extracted with chloroform, organic layer dried over sodium sulfate, concentrated in vacuo, and purified by chromatography on silica (ethyl acetate) to afford 3.9 g (48.7%) of di-(4-pyridyl)ketone.

(c)

A suspension of methyltriphenylphosphonium bromide (6.4 g; 18 mmol) in 75 ml of ether was added at 0° C. n-butyllithium in hexane (7.2 ml; 18 mmol) and the mixture was stirred at room temperature under nitrogen for 1 hour. To the above mixture was added 3 g (16 mmol) of 1,1-di(4-pyridyl)ketone in 20 ml of tetrahydrofuran over a 10 min period and the mixture was stirred at room temperature for 30 minutes. The above reaction mixture was quenched with water and stirring. The organic layer was separated, dried over sodium sulfate, and concentrated in vacuo. The residue was purified by chromatography on silica eluting with ethyl acetate/methylene chloride/methanol (7:2:1) to afford 2.2 g (73.3%) of 1,1-di(4-pyridyl)ethylene (Formula III: $R^2$=$R^3$=H; $R^4$=$R^5$=4-pyridyl).

EXAMPLE 44

(a)

To cooled (−78° C.) THF (100 ml) was added under nitrogen, n-butyllithium (2.5M, 40 ml) to the above mixture was added N-methyl-N-methoxy-urethane (6.28 g, 0.047 mol) in 5 ml of THF over a 0.5 h period and the mixture was allowed to warm to room temperature. The mixture was quenched with saturated ammonium chloride solution and the aqueous layer was extracted with ether. The combined organic layer was dried over magnesium sulfate, concentrated in vacuo, and the oil residue was crystallized from methanol to afford 1.465 g (16%) of 1,1-di-(3-thienyl)-ketone, m.p. 78°–80° C. Alternatively, 1,1-di-(3-thienyl) ketene was prepared as follows: To 100 ml of THF cooled −78° C. under nitrogen was added 2.5M n-butyllithium (36 ml ), and 14.67 g (0.09 mol) of 3-bromthiophene was added and the resulting mixture was stirred for 30 min. To the above mixture was added 3-thiophenecarboxaldehyde (10 g, 0.089 mol) in 10 ml of THF and the mixture was stirred allowing it to reach room temperature. Saturated ammonium chloride solution was added to the reaction mixture, the aqueous layer was extracted with ether, and the combined organic layer was concentrated in vacuo to yield 17.26 g (98.9%) of 1,1-di(3-thienyl)-methanol, as an oil.

Chromium trioxide (1.4 g) was dissolved in 12 ml of water and 24 ml of acetic acid, and the resulting mixture was added dropwise to 1,1-di(3-thienyl)-methanol in 30 ml of acetic acid over 1 h period. The above mixture was stirred for 1 h with cooling (20° C.) in an ice-water bath. The mixture was diluted with 150 ml of water, extracted with methylene chloride, and the organic layer was washed with saturated sodium bicarbonate solution, dried over sodium sulfate, and concentrated in vacuo to yield an oil, which was crystallized in methanol to afford 1.85 g (47.7%) of 1,1-di(3-thienyl)ketone, as a solid, m.p. 79°–81° C.

(b)

To a suspension of methyltriphenylphosphonium bromide (15.7 g; 44 mmol) in 75 ml of ether was added under nitrogen at 0° C. 2.5M n-butyllithium in hexane (17.6 ml; 43 mmol) dropwise (<5° C.) and the mixture was allowed to warm and stir at room temperature for ½ h. To the above mixture was added 7.85 g (44 mmol) of di(3-thienyl)ketone in 50 ml of tetrahydrofuran dropwise and the mixture was stirred at room temperature for ½ h. To the above reaction mixture was added 20 ml of acetone, concentrated in vacuo, and the residue was partitioned in water/methylene chloride and methylene chloride was distilled in vacuo. The oil residue was distilled (0.02 mm/95°–100° C.) to afford 5.944 g (77.3%) of 1,1-di(3-thienyl)ethylene (Formula III: $R^2$=$R^3$=H; $R^4$=$R^5$=3-thienyl), as a colorless oil.

EXAMPLE 45

(a)

To a suspension of 1,1-carbonyldimidazole (90 g, 0.555 mol) in 400 ml of THF at 0° C. was added dropwise formic acid 25.5 g (0.555 mol) in 100 ml of THF over a 15 min period. The mixture was warmed to room temperature and stirred for 1.5 h. The resulting solution was added via canula to the anion of methyl isocyanoacetate (generated by addition of the methyl isocyanoacetate in 75 ml of THF to a suspension of potassium t-butoxide at 0° C. and stirring for 15 min) at 0° C. During the addition (exothermic), the reaction mixture reached to 20° C. and the ice-bath was removed, stirring the mixture at room temperature for 1 h. The above mixture was quenched with 100 ml of acetic acid followed by 200 ml of water, THF was removed in vacuo, and 1000 ml of chloroform was added to the residual mixture. The organic layer was washed with water (2×200 ml), saturated sodium bicarbonate solution (1×100 ml), water, brine, and dried over sodium sulfate and concentrated in vacuo. The resulting residue was chromatographed on silica (methylene chloride/hexane/ether 7:2:1) to afford 23.5 g (37%) of methyl 4-oxazolecarboxylate.

(b)

To a suspension of methoxy-methylamine hydrochloride (2.3 g, 23.6 mmol) in 30 ml of dichloroethane at 0° C. was added dropwise 11.8 ml (23.6 mmol) of trimethylaluminum. The mixture was stirred at 0° C. for 20 min, methyl 4-oxazolecarboxylate (1 g, 7.9 mmol) in 20 ml of dichloroethane was added in one portion. The mixture was poured into an ice-cold solution of 0.5N HCl/methylene chloride (2:1) and stirred for 10 min. The aqueous layer was extracted with methylene chloride (2×50 ml), and the combined organic layer was washed with saturated ammonium chloride solution, dried over sodium sulfate, and concentrated in vacuo. The resulting residue was purified by chromatography on silica (methylene chloride/ethyl acetate/methanol 6:3:1) to afford 1.0 g (81.9%) of 4-oxazolyl-N-methyl-N-methoxy-carboxamide.

(c)

To a solution of 4-oxazolyl-N-methyl-N-methoxy-carboxamide (2.76 g, 17.6 mmol) in 250 ml of DME/THF (2:1) and 100 ml of DME cooled to −78° C., was added 1M solution of LAH (35.3 ml, 35.3 mmol) in THF over a 15 min period and the mixture was stirred at −78° C. for 1 h. After an additional addition of 35 ml of LAH solution, the mixture was stirred for 15 min, quenched with 2.6 ml of water, followed by 2 ml of 10% NaOH solution and 2.6 ml of water. The above mixture was stirred at room temperature for 15 min, filtered, and the residue was washed with 600 ml of MDC/acetone (2:1). The combined filtrate was concentrated in vacuo, and the residue was purified by chromatography on silica (MDC/ethyl acetate 6:1) to afford 0.62 g (36%) of 4-oxazolylcarboxaldehyde.

(d)

To a solution of oxazole (0.4 ml (6.2 mmol) in 20 ml of THF cooled −78° C. under nitrogen was added 2.5M n-butyllithium (2.5 ml, 6.2 mmol). The mixture was stirred at −78° C. for 30 min and a solution of 4-oxazolylcarboxaldehyde (0.6 g, 6.2 mmol) in 25 ml of THF was added dropwise. The resulting mixture was warmed to room temperature and stirred overnight. The reaction mixture was quenched with a suspension of Dowex® 50x2-200 ($H^+$) in methanol (20 ml) and stirred for 30 min, filtered, and the filtrate was concentrated in vacuo. The residue was dissolved in methylene chloride, dried over magnesium sulfate, and concentrated in vacuo. The resulting residue was purified by chromatography on silica (5% methanol in MDC) to afford 0.35 g (33.9%) of 1,1-di(4-oxazolyl)-methanol.

(e)

To a suspension of chromium trioxide (1.35 g, 13.5 mmol)) in 75 ml of methylene chloride at 0° C. was added 2.1 g (12.6 mmol) of pyridine and the mixture was allowed to warm to room temperature and stirred for 30 min. To the mixture was added 1,1-di(4-oxazolyl)-methanol (0.35 g, 2.1 mmol) in 10 ml of MDC, and mixture was stirred at room temperature under nitrogen for 15 min. The mixture was diluted with 100 ml of ethyl acetate, stirred, filtered through a pad of florisil (4 inches) eluting with 300 ml of ethyl acetate to afford 0.15 g (43.4%) of 1,1-di(4-oxazolyl)ketone, as a white solid.

(f)

To a suspension of methyltriphenyl-phosphonium bromide (0.36 g; 1.01 mmol) in 10 ml of THF was added under nitrogen at 0° C. 2.5M n-butyllithium (0.4 ml,1.01 mmol), and the mixture was stirred for 30 min. To the above mixture was added di(4-oxazolyl)ketone (0.15 g, 0.92 mmol) in 10 ml of THF and the mixture was stirred for 1 h. The mixture was quenched with 25 ml of saturated ammonium chloride solution and 50 ml of MDC was added and stirred. The organic layer was dried over sodium sulfate, concentrated in vacuo, and the residue was purified by chromatography on silica (hexane/ethyl acetate 2:1) to afford 0.05 g (33.3%) of 1,1-di(4-oxazolyl)ethylene (Formula III: $R^2$=$R^3$=H; $R^4$=$R^5$= 4-oxazolyl).

EXAMPLE 46

To a suspension of methyltriphenylphosphonium bromide (15.6 g; 44 mmol) in 200 ml of ether cooled to −10° C. was added dropwise 2.2M n-butyllithium in hexane (20 ml; 44 mmol) at −10° C. and the mixture was allowed to warm to room temperature. To the above mixture cooled to −10° C. was added 10 g (44 mmol) of 1,1-di(m-chlorophenyl)ketone in one portion, the mixture was stirred overnight at room temperature. The mixture was quenched with water, extracted with ethyl acetate, and the organic layer was washed with water, dried over sodium sulfate, and concentrated in vacuo to afford 11.55 g of an oil. The oil was purified by chromatography on silica eluting with hexane to afford 6.5 g (65.3%) of 1,1-di(m-chlorophenyl)ethylene (Formula III: $R^2$=$R^3$=H; $R^4$=$R^5$=3-$Cl^-$phenyl), as a colorless oil.

EXAMPLE 47

(a)

To a solution of 45.04 g (0.66 mol) of furan in 300 ml of ether was added 36.3 ml (0.363 mol) of 10M n-butyllithium at −20° C. and the mixture was warmed to 0° C. and stirred for 1 h. The above mixture was cooled to −78° C. and N-methyl-N-methoxy-urethane (22 g, 0.165 mol) in 20 ml of ether was added dropwise over a 20 min period and the resulting mixture was allowed to warm to room temperature for 1 h. The reaction mixture was quenched with 100 ml of ammonium chloride solution, extracted with ether (2×100 ml), and the organic layer was dried over sodium sulfate and concentrated in vacuo to yield an oil. The above oil was purified by chromatography on silica (methylene chloride) to afford 26.5 g (95%) of 1,1-di(2-furyl)ketone, as an oil.

(b)

A suspension of methyltriphenylphosphonium bromide (11.56 g; 32.3 mmol) in 100 ml of ether was added at −30° C. 10M n-butyllithium in hexane (3.23 ml; 32.3 mmol) and the mixture was allowed to stir at room temperature for 1 hour. To the above mixture was added 5 g (30.8 mmol) of 1,1-di(2-furyl)ketone in 15 ml of tetrahydrofuran in 1 min and the mixture was heated to refluxed. The above mixture was cooled, filtered, and concentrated to yield 4.92 g (100%) of 1,1-di(2-furyl)ethylene (Formula III: $R^2$=$R^3$=H; $R^4$=$R^5$= 2-Furyl).

EXAMPLE 48

(a)

To a cooled (−78° C.) ether solution containing n-butyllithium (2.5M, 13 ml, 32.5 mmol) was added 5.2 g (31 mmol) of 2-bromothiazole in 50 ml of ether over 30 min period, and the mixture was stirred (−78° C.) for 1 h. N-Methyl-N-methoxy-urethane (2.1 g, 15 mol) in 25 ml of ether was added to the above mixture over a 15 min period, the resulting reaction mixture was stirred at −78° C. for 1 h, warmed to room temperature, and stirred for 2 h. The above mixture was quenched with 3N HCl (200 ml) and stirred for 15 min. The aqueous layer was treated with solid sodium bicarbonate (to pH 9), the precipitated solid was filtered, and washed with water, and dried to yield a solid product.. The solid product was purified by chromatography on silica (hexane/ether/methylene dichloride 4:2:1) to afford 1.7 g (54.8%) of 1.1-di(2-thiazolyl)ketone.

(b)

To a solution of 1,1-di(2-thiazolyl)ketone (1.96 g, 10 mmol) in 75 ml of THF cooled to 0° C. under nitrogen was added 15 ml (15 mmol) of 1M trimethylsilyl-methylmagnesium chloride over a 10 min period, and the resulting mixture was warmed to room temperature and stirred for 1 h. The reaction mixture was quenched with 3 ml of ammonium chloride solution, diluted with 100 ml of methylene chloride, and filtered. The filtrate was washed with saturated ammonium chloride solution, and the organic layer was dried over sodium sulfate and concentrated in vacuo. The residue was purified by passing through a pad of silica, eluting with hexane/ether/methylene chloride 4:2:1) to afford 1.1 g (38.5%) of 1,1-di(2-thiazolyl),2-trimethylsilylethanol.

EXAMPLE 49

(a)

To a cooled (−78° C.) ether (200 ml) solution containing n-butyllithium (2.5M, 13.5 ml, 33 mmol) was added 6.43 g (40.9 mmol) of 2-trimethylsilyl-thiazole in 50 ml of ether over 1 h period and the mixture was stirred (−78° C.) for 1 h. N-Methyl-N-methoxy-urethane (2.32 g, 17.5 mol) in 50 ml of ether was added to the above mixture over 15 min period, the resulting reaction mixture was stirred at −78° C. for 1 h, and then warmed to room temperature with stirring. The above mixture was quenched with 3N HCl and stirred for 2 h. The aqueous layer was treated with solid sodium bicarbonate (to pH 8), diluted with saturated ammonium chloride solution, and extracted with chloroform (3×150 ml). The combined organic layer (including original ether layer) was dried over sodium sulfate, and concenetrated in vacuo. The residue was triturated with ether (50 ml), filtered, and dried to afford 160 mg (4.6%) of 1,1-di(5-thiazolyl)ketone.

(b)

To a suspension of methyltriphenylphosphonium bromide (0.35 g; 1 mmol) in 15 ml of THF was added under nitrogen at 0° C. 2.5M n-butyllithium (0.4 ml,1 mmol) and the mixture was stirred for 1 h. To the above mixture was added 1,1-di(5-thiazolyl)ketone (0.16 g, 0.82 mmol) in 5 ml of THF and the mixture was stirred under nitrogen at room temperature for 2 h. The mixture was quenched with 2 ml of acetone, diluted with 50 ml of ether, and filtered. The filtrate was concentrated in vacuo and the residue was purified by chromatography on silica (ether) to afford 0.035 g (21.8%) of 1,1-di(5-thiazolyl)ethylene (Formula III: $R^2$=$R^3$=H; $R^4$=$R^5$=5-thiazolyl).

EXAMPLE 50

To 300 ml of THF was added with cooling (ice-bath) 300 ml (0.3 mol) of 1M $TiCl_4$ in methylene chloride and the mixture was stirred for 10 min. To the above mixture was added at room temperature 90.5 ml (0.6 mol) of TMEDA, the mixture was stirred for 10 min, and then, 44.12 g (0.675 mol) of Zn dust was added with cooling to maintain the mixture at room temperature and stirred for 40 min. To the resulting reaction mixture was added dropwise a mixture of ethyl 3-furoate (10.5 g, 0.075 mol), 31 g (0.165 mol) of dibromoethane in 200 ml of THF, and the mixture was stirred at room temperature for 2.5 h. After adding 90 ml of aqueous potassium carbonate solution, the mixture was concentrated in vacuo, the residue was diluted with 20 g of basic alumina, passed through basic alumina column (ether/TEA 200:1), and the eluent was concentrated. The residue was triturated in ether (200 ml), filtered, and the filtrate was distilled (80°–95° C./25 mm) to afford 6.2 g of (54.3%) of 1-(3-furyl)-1-ethoxy-2-methylethylene (Formula III: $R^2$=$CH_3$; $R^3$=H; $R^4$=$CH_3CH_2O$; $R^5$32 3-Furyl; and Formula III: $R^2$=H; $R^3$=$CH_3$; $R^4$=3-Furyl; $R^5$=$CH_3CH_2O$).

EXAMPLE 51

(a)

To a cooled (−78° C.) 1 L ether solution containing 25 g (0.105 mol) of 2,6-dibromopyridine was added n-butyllithium (2.5M, 42 ml, 0.105 mol) over a 20 min period, and the mixture was stirred at −78° C. for ½ h. To the above mixture was added at −78° C. N-methyl-N-methoxy-urethane (6.6 g, 0.049 mol) in 50 ml of ether and the mixture was stirred at −78° C. for 1 h, and was allowed to warm to room temperature and stirred for 3 h. The above mixture was quenched with 100 ml of saturated ammonium chloride solution and stirred overnight. The organic layer was dried over sodium sulfate, concentrated in vacuo, and the residue was triturated with ether, filtered, and the solid residue was dried to afford 11 g (65.47%) of 1,1-di[(6-bromo)-2-pyridyl] ketone. This solid product was recrystallized from ethyl acetate to yield 8.2 g of the ketone.

(b)

To 200 ml of methanol was added in portions 2.3 g (0.1 mol) of sodium and the mixture was stirred under nitrogen for 2 h. 1,1-di[(6-bromo)-2-pyridyl]-ketone (8 g, 0.024 mol) was added to the above mixture, and the reaction mixture was refluxed under nitrogen for 24 h. An additional 2 g of sodium methoxide was added to the mixture and refluxed for 48 h, and cooled. The mixture was diluted with ether, washed with saturated ammonium chloride solution, and the organic layer was dried over sodium sulfate, and concentrated in vacuods. The residue was purified by chromatography on silica (ether/hexane, 2:8) to afford 2.5 g (42.7%) of 1,1-di(6-methoxypyridin-2-yl)methanol. In addition, 100 mg of 1,1-di(6-methoxypyridin-2-yl)ketone was also isolated from the chromatographic fractions.

(c)

To a solution of 10.2 g (0.13 mol) of pyridine in 500 ml of methylene chloride at 0° C. was added $CrO_3$ (6.5 g, 0.011 mol) in portions, and the mixture was stirred at 0° C. for 1 h. To the above mixture was added 1,1-di(6-methoxypyridin-2-yl)methanol (2.5 g, 0.011 mol) in 50 ml of methylene chloride and the mixture was stirred for 2 h at room temperatute. The reaction mixture was diluted with ethyl acetate, filtered through celite, and the filtrate was concentrated in vacuo to afford 1.65 g (66%) of 1,1-di(6-methoxypyridin-2-yl)ketone.

(d)

To a suspension of 1.25 g (0.011 mol) of potassium t-butoxide in 30 ml of THF at 0° C. was added methyltriphenylphosphonium bromide (3.57 g; 0.01 mol) and the mixture was stirred at room temperature for 1 h. To the above mixture was added 1,1-di(6-methoxypyridin-2-yl)ketone (1.6 g, 0.0657 mol) in 30 ml of THF and the mixture was stirred for 30 min at room temperature under nitrogen. The above mixture was quenched with saturated ammonium chloride solution, diluted with ether, filtered, the aqueous layer was extracted with ether, and the combined organic layer was filtered. The above filtrate was concentrated in vacuo, and the residue was chromatographed on silica (hexane/ether, 8:2) to afford 0.94 g (59.4%) of 1,1-di(6-methoxypyridin-2-yl)ethylene (Formula III: $R^2=R^3=H$; $R^4=R^5=6\text{-}OCH_3$-2-Pyridyl).

EXAMPLE 52

(a)

To a suspension of 3.5 g (0.139 mol) of sodium hydride in 120 ml of DMF at 0° C. was added 8 g (0.115 mol) of 1,2,3-triazole in 50 ml of DMF dropwise, and the mixture was allowed to warm to room temperature and stirred for 1 h. The above mixture was cooled to 0° C., and 21.8 g (0.139 mol) of p-methoxybenzyl chloride was added, and the mixture was allowed to warm to room temperature and stirred for 20 h. The reaction mixture was concentrated in vacuo and the residue was purified by chromatography on silica (hexane/ethyl acetate) to afford 14 g (64.5%) of 1-(p-methoxybenzyl)-1,2,3-triazole.

(b)

To a cooled (−78° C.) 600 ml of THF solution containing 14 g (0.074 mol) of 1-(p-methoxybenzyl)-1,2,3-triazole was added n-butyllithium (2.5M, 30 ml, 0.07 mol) dropwise over a 15 min period, and the mixture was stirred at −78° C. for 2 h. The mixture was stirred at −78° C. for 1.5 h, and N-methyl-N-methoxy-urethane (4.5 g, 0.033 mol) in 25 ml of THF was added. The mixture was stirred at −78° C. for 1 h, and then warmed to room temperature and stirred for 2 h under nitrogen. The above mixture was quenched with saturated ammonium chloride solution and the layers were separated. The organic layer was dried over sodium sulfate, concentrated in vacuo, and the residue was triturated with ether and filtered to afford 10.4 g of 1,1-di[5-(1-p-methoxybenzyl)-1,2,3-triazolyl]ketone.

(c)

To a suspension of methyltriphenylphosphonium bromide (14.5 g; 0.04 mol) in 300 ml of THF was added under nitrogen at −5° C. 2.5M n-butyllithium (16.2 ml0.04 mol) and the mixture was stirred for 1 h. To the above mixture was added 1,1-di[5-(1-p-methoxybenzyl)-1,2,3-triazolyl]ketone (10.9 g, 0.027 mol) in 100 ml of THF and the mixture was stirred for 2 h at room temperature under nitrogen. The above mixture was quenched with 10 ml of acetone, and 200 ml of ether was added and the mixture was stirred overnight. The mixture was concentrated in vacuo, the residue was partitioned between water and methylene chloride with stirring. The mixture was filtered, the organic filtrate was concentrated in vacuo, and the residue was purified by chromatography on silica to afford 1.2 g (11%) of 1,1-di[5-(1-p-methoxybenzyl)-1,2,3-triazolyl]-ethylene (Formula III: $R^2=R^3=H$; $R^4=R^5=1$-p-methoxybenzyl-5-(1,2,3-triazolyl).

EXAMPLE 53

(a)

To a solution of 1-triisoproylsilyl-pyrrole (13.2 g,0.059 mol) in 250 ml of THF at −78° C. was added 10.45 g (0.0587 mol) of N-bromosuccinamide (NBS), the mixture was stirred at −78° C. for 3 h. The reaction mixture was warmed to room temperature and concentrated in vacuo, and the resulting residue in hexane was stirred overnight. The hexane solution was filtered through alumina eluting with hexane, the eluent was concentrated in vacuo, and the residue was distilled (b.p. 107°–108° C./0.2 mm) to afford 10.4 g (58.4%) of 3-bromo-1-triisopropylsilyl-pyrrole.

(b)

To a solution of 3-bromo-1-triisopropylsilyl-pyrrole (10.4 g,0.0292 mol) in 150 ml of THF at −78° C. was added n-butyllithium (2.5M, 12.3 ml, 0.031 mol) and the mixture was stirred at −78° C. for ½ h. To the above mixture was added N-methyl,N-methoxy-urethane (1.9 g, 0.014 mol) in 25 ml of THF, the mixture was allowed to warm to room temperataure and stirred under nitrogen for 20 h. The mixture was quenched with saturated sodium bicarbonate solution and the layers were separted. The organic layer was dried over sodium sufate, concentrated in vacuo, and the residue was chromatographed on silica (hexane/ether, 2:1) to afford 4.25 g (64.3%) of 1,1-di[3-(1-triisopropylsilyl)-pyrrolyl]-ketone, as an oil.

(c)

To a solution of 1,1-di[3-(1-triisopropylsilyl)-pyrrolyl]-ketone (1 g 2.1 mmol) in 30 ml of THF at room temperature was added methylmagnesium bromide in ether (3.0M, 9 mmol) and the mixture was stirred for ½ h. The above reaction mixture was quenched with 2 ml of saturated sodium bicarbonate solution. The reaction mixture was diluted with methylene chloride, stirred, passed through a florisil column, and the filtrate was concentrated in vacuo to afford 1.1 g (100 %) of 1,1-di[3-(1-triisopropylsilyl)-pyrrolyl]-ethylene (Formula III: $R^2=R^3=H$; $R^4=R^5=1$-triisopropylsilyl-3-pyrrolyl).

EXAMPLE 54

(a)

To 3-furaldehyde (25.0 g, 0.26 mol) in THF (250 mL) at 78° C. was added ethynylmagnesium bromide (572 mL, 0.286, 0.5M THF) at the rate of 10 mL per minute. The mixture was slowly warmed to room temperature, stirred for 1 hour and then poured into a cooled ammonium chloride solution. The mixture was extracted with ethyl acetate, and the organic layer was dried over $Na_2SO_4$ and concentrated in vacuo. The residue was distilled at 50°–55° C. and 0.24 mmHg to afford 1-(3-furyl)-1-hydroxy-2-propyne.

(b)

To a mixture of 1-(3-furyl)-1-hydroxy-2-propyne (20.0 g, 0.163 mol), hexane (200 mL) and THF (25 mL) was added tetrabutylammonium bromide (1.05 g, 0.0032 mol), 50% NaOH (150 mL) and then diethylsulfate (30.0 g, 0.195 mol) at 0° C. The mixture was stirred for 3 hours at room temperature, poured into ice, and extracted with ethyl acetate. The combined organic layers were wasted with brine, dried over $Na_2SO_4$ and concentrated in vacuo. The residue was distilled at 70°–84° C. and (10 mmHg) to afford 1-(3-furyl)-1-ethoxy-2-propyne.

Following procedures similar to those described in Example 38, parts a–b, but substituting an appropriately substituted 5- or 6-membered monocyclic aromatic heterocyclic halide, a 9-or 10-membered bicyclic aromatic heterocyclic halide or a 5- or 6-membered monocyclic nonaromatic heterocyclic halide for 3-bromopyridine in part a, it is contemplated that the following olefins of the Formula III illustrated in the Table 1 can be prepared.

TABLE 1

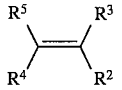

III

| Example Number | $R^2$ | $R^3$ | $R^4$ | $R^5$ |
|---|---|---|---|---|
| 55 | H | H | 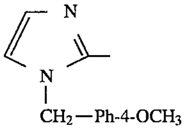 | 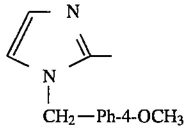 |
| 56 | H | H | 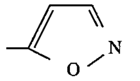 | 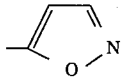 |
| 57 | H | H | 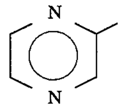 | 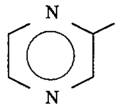 |
| 58 | H | H | 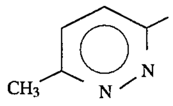 | 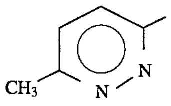 |
| 59 | H | H | 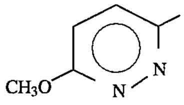 | 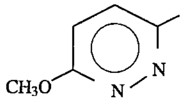 |
| 60 | H | H | 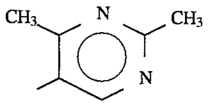 | 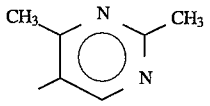 |
| 61 | H | H | 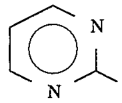 | 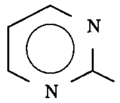 |
| 62 | H | H | 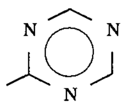 | 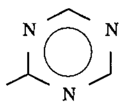 |
| 63 | H | H | 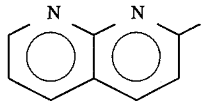 | 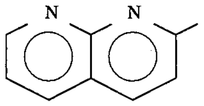 |
| 64 | H | H | 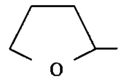 | 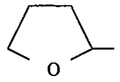 |

TABLE 1-continued
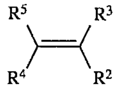
III
| Example Number | $R^2$ | $R^3$ | $R^4$ | $R^5$ |
|---|---|---|---|---|
| 65 | H | H | 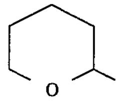 | 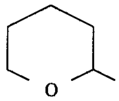 |
| 66 | H | H | Ph | 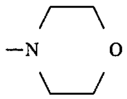 |
| 67 | H | H | 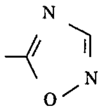 | 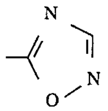 |
| 68 | H | H | 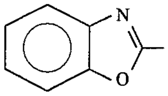 | 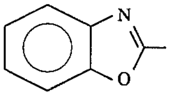 |
| 69 | H | H | 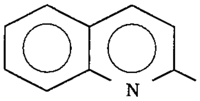 | 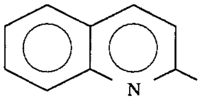 |
| 70 | H | H | 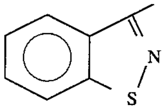 | 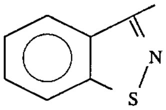 |
| 71 | H | H | 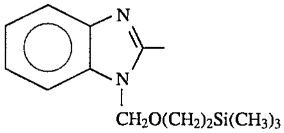 | 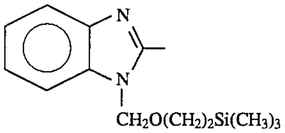 |
| 72 | H | H | 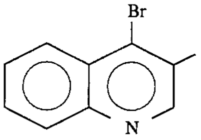 | 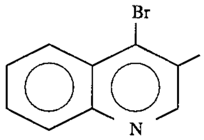 |
| 73 | H | H | 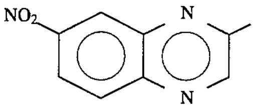 | 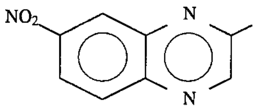 |
| 74 | H | H | 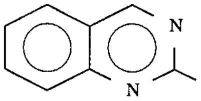 | 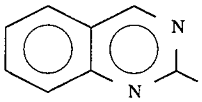 |
| 75 | H | H | 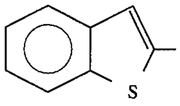 | 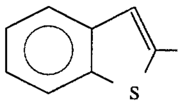 |
| 76 | H | H | 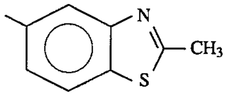 | 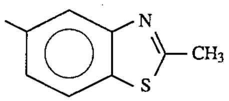 |

TABLE 1-continued

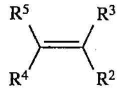

III

| Example Number | $R^2$ | $R^3$ | $R^4$ | $R^5$ |
|---|---|---|---|---|
| 77 | H | H | 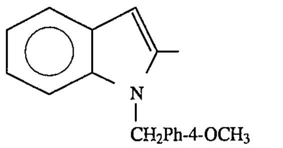 | 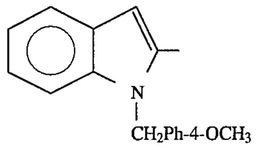 |
| 77a | H | H | 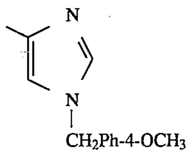 | 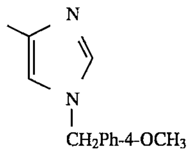 |
| 77b | H | H | 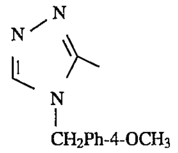 | 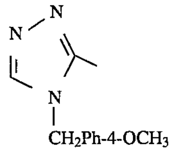 |
| 77c | H | H | 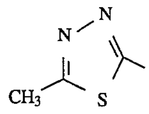 | 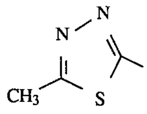 |
| 77d | H | H | 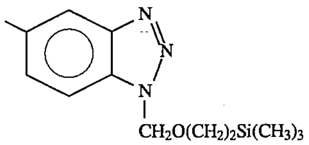 | 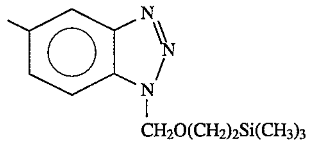 |
| 77e | H | H | 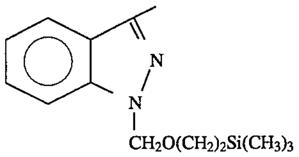 | 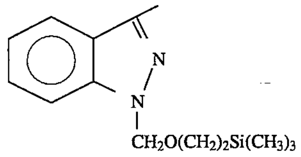 |

EXAMPLES 78 a–b

Following procedures similar to those described in Example 18, parts c and d, but substituting an appropriate halide for p-methoxybenzylchloride in part c, it is contemplated that there can be prepared the following olefins of the Formula III.

(a)

1,1-Di[1-(methyl)-3-pyrazolyl]ethylene (Formula III: $R^2$=$R^3$=H; $R^4$=$R^5$=1-methyl-3-pyrazolyl)

(b)

1,1-Di[1-(benzyl)-3-pyrazolyl]ethylene (Formula III: $R^2$=$R^3$=H; $R^4$=$R^5$=1-benzyl-3-pyrazolyl)

EXAMPLES 79 a–b

Following procedures similar to those described in Example 52, parts a, b and c, but substituting an appropriate halide for p-methoxybenzylchloride in part a, it is contemplated that there can be prepared the following olefins of the Formula III.

(a)

1,1-Di[1(4-methylbenzyl)-5-(1,2,3-triazolyl)]ethylene (Formula III: $R^2$=$R^3$=H; $R^4$=$R^5$=1-(4-methylbenzyl)-5-(1,2,3-triazolyl))

(b)

1,1-Di[1(4-chlorobenzyl)-5-(1,2,3-triazolyl)]ethylene (Formula III: $R^2$=$R^3$=H; $R^4$=$R^5$=1-(4-chlorobenzyl)-5-(1,2,3-triazolyl))

EXAMPLES 80 a–b

Following procedures similar to those described in Example 41, but substituting an appropriately substituted benzophenone derivative for 3,3'-bis (trifluoromethyl) benzophenone, it is contemplated that the following olefins of the Formula III can be prepared.

(a)

1,1-Di(3-trichlormethylphenyl)ethylene (Formula III: $R^2$=$R^3$=H; $R^4$=$R^5$=3-trichloromethylphenyl)

(b)

1,1-Di(3-hydroxyphenyl)ethylene (Formula III: $R^2$=$R^3$=H; $R^4$=$R^5$=3-hydroxyphenyl)

Following procedures similar to those described in a) Example 1, parts a–d, but substituting an appropriately substituted 5- or 6-membered monocyclic aromatic heterocyclic halide for 2-bromothiazole in part a, and an appropriately substituted benzyl halide of the formula IV for benzyl bromide in part c; or b) Example 6, parts a–b, but substituting an appropriately substituted benzyl alcohol of formula VII for 3-methoxybenzylalcohol and an appropriately substituted 5- or 6-membered monocyclic aromatic heterocyclic carboxaldehyde of formula VIII for thiazole-2-carboxaldehyde in part a; or c) Example 12, parts a–d, but substituting an appropriately substituted 5-or 6-membered monocyclic aromatic heterocycle for n-benzylimidazole in part a, and an appropriately substituted benzyl halide formula IV for benzyl bromide in part c; or d) Example 19, parts b–d, but substituting an appropriately substituted 5- or 6-membered monocyclic aromatic heterocycle for 1-(4-methoxybenzyl)imidazole in part b, and an appropriately substituted 2-halobenzyl alcohol of formula VII for 2-bromobenzyl alcohol in part c; it is contemplated that the following compounds of the formula II which are illustrated in Table 2 can be prepared.

TABLE 2

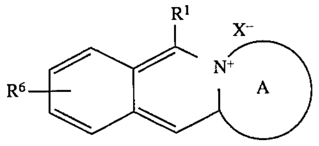

| Example Number | A | $R^1$ | $R^6$ | $X^-$ |
|---|---|---|---|---|
| 81 | 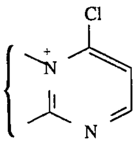 | H | H | $ClO_4^-$ |
| 82 | 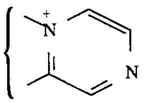 | $CH_3$ | H | $ClO_4^-$ |
| 83 | 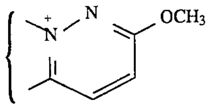 | H | H | $ClO_4^-$ |
| 84 | 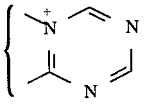 | H | H | $ClO_4^-$ |
| 85 | 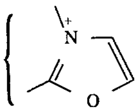 | H | H | $ClO_4^-$ |
| 86 | 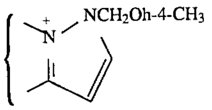 | H | H | $PF_6^-$ |
| 87 | 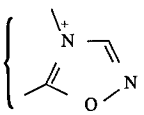 | H | H | $ClO_4^-$ |
| 88 | 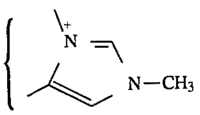 | H | H | $PF_6^-$ |

TABLE 2-continued
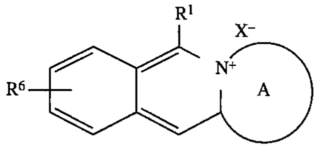
| Example Number | A | $R^1$ | $R^6$ | $X^-$ |
|---|---|---|---|---|
| 89 | 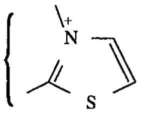 | $CH_3$ | H | $ClO_4^-$ |
| 90 | 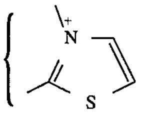 | $CH_3CH_2CH_2$ | H | $ClO_4^-$ |
| 91 | 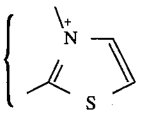 | H | 8-$OCH_3$ | $ClO_4^-$ |
| 92 | 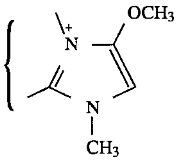 | H | H | $ClO_4^-$ |
| 93 | 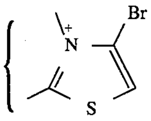 | H | 9-$OCH(CH_3)_2$ | $ClO_4^-$ |
| 94 | 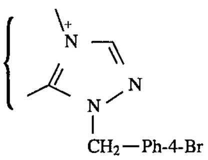 | H | 7,9-$F_2$ | $ClO_4^-$ |
| 95 | 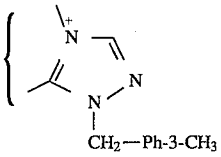 | H | 8-$CF_3$ | $PF_6^-$ |
| 96 | 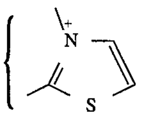 | H | 6,9-$Br_2$ | $ClO_4^-$ |
| 97 | 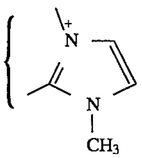 | H | 8-$CCl_3$ | $ClO_4^-$ |
| 98 | 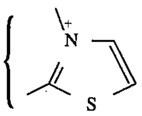 | H | 8,9-$OCH_2O^-$ | $ClO_4^-$ |

TABLE 2-continued

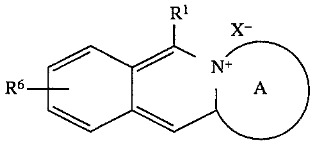

| Example Number | A | $R^1$ | $R^6$ | $X^-$ |
|---|---|---|---|---|
| 99 | 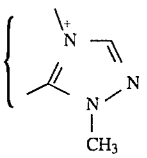 | H | 8-$NO_2$ | $ClO_4^-$ |
| 100 | 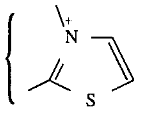 | H | 9-$CH_3$ | $ClO_4^-$ |
| 101 | 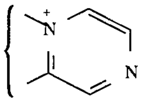 | H | 9-$OCH_3$ | $ClO_4^-$ |
| 102 | 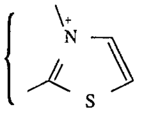 | H | 6,7,8,9-$F_4$ | $ClO_4^-$ |
| 103 | 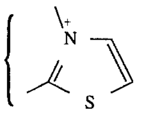 | H | 6,7,8-$(OCH_3)_3$ | $ClO_4^-$ |
| 104 | 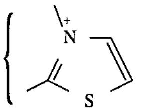 | H | 7-Br,8-$CH_3$ | $ClO_4^-$ |
| 104a | 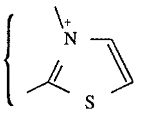 | H | 8-CN | $ClO_4^-$ |

EXAMPLE 105

It is contemplated that treatment of 9-methoxy-thiazolo [1,2-b]isoquinolin-4-ium perchlorate of Example 6(b) with 48% HBr at reflux will produce 9-hydroxy-thiazolo[3,2-b] isoquinolinium bromide.

EXAMPLE 106

It is contemplated that treatment of 9-hydroxy thiazolo [1,2-b]isoquinolin-4-ium bromide in $CH_2Cl_2$ with pyridine, dimethylaminopyridine and acetic anhydride will produce 9-acetoxythiazolo[3,2-b]isoquinolinium bromide.

Following procedures similar to those described in Example 1, part h, but substituting an appropriately substituted olefin of the Formula III for 2,2-dimethyl-1,1-diethoxyethylene and an appropriately substituted heterocyclyl[1,2-b]isoquinolinium salt of the Formula II for thiazolo [3,2-b]isoquinolinium perchlorate, it is contemplated that the following compounds of the Formula I illustrated in Table 3 can be prepared.

TABLE 3
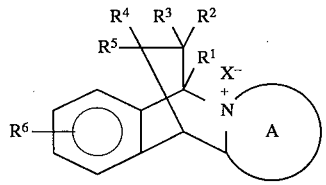
| Example Number | A | $R^1$ | $R^2$ | $R^4$ | $R^3$ | $R^5$ | $R^6$ | X− |
|---|---|---|---|---|---|---|---|---|
| 107 | 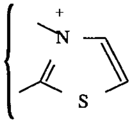 | H | H | Ph | | 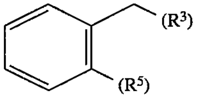 | H | $ClO_4$− |
| 108 | 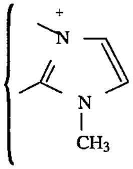 | H | | 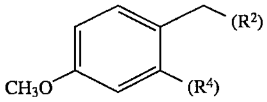 | H | Ph | H | $ClO_4$− |
| 109 | 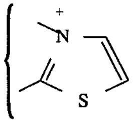 | H | H | Ph | | 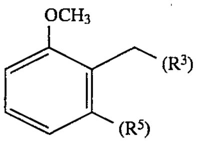 | 9-$OCH_3$ | $ClO_4$− |
| 110 | 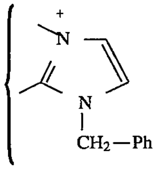 | H | | 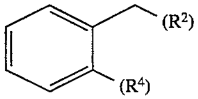 | H | 3-$CH_3O$−Ph | H | $ClO_4$− |
| 111 | 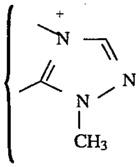 | H | H | 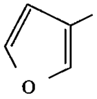 | | 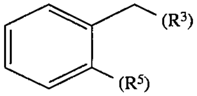 | H | $ClO_4$− |

TABLE 3-continued
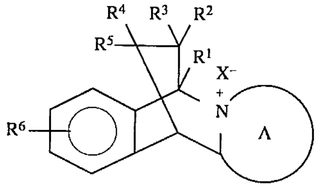
| Example Number | A | $R^1$ | $R^2$ | $R^4$ | $R^3$ | $R^5$ | $R^6$ | X− |
|---|---|---|---|---|---|---|---|---|
| 112 | 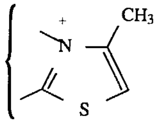 | H | | 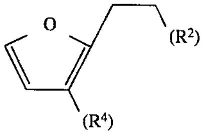 | H | 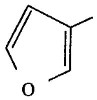 | H | $ClO_4^-$ |
| 113 | 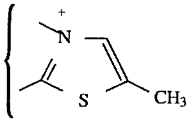 | H | H | 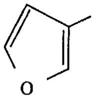 | | 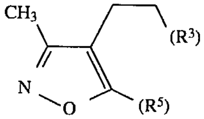 | H | $ClO_4^-$ |
| 114 | 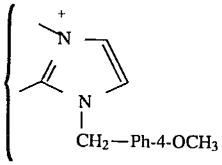 | H | | 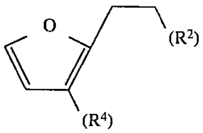 | H | $OCH_2CH_3$ | H | $PF_6^-$ |
| 115 | 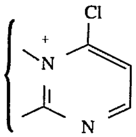 | H | H | 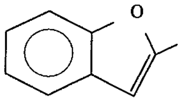 | | 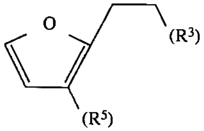 | H | $ClO_4^-$ |
| 116 | 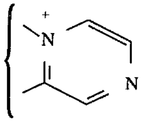 | $CH_3$ | H | 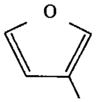 | H | $OCH_2CH_3$ | H | $ClO_4^-$ |

TABLE 3-continued
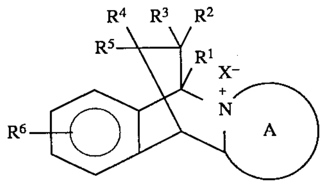
| Example Number | A | $R^1$ | $R^2$ | $R^4$ | $R^3$ | $R^5$ | $R^6$ | X− |
|---|---|---|---|---|---|---|---|---|
| 117 | 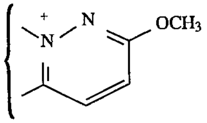 | H | H | $OCH_2CH_3$ | H | 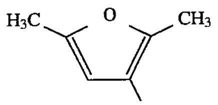 | H | $ClO_4$− |
| 118 | 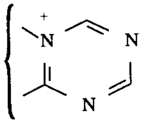 | H | H | 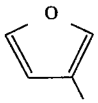 | $CH_3$ | 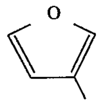 | H | $ClO_4$− |
| 119 | 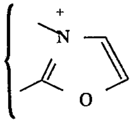 | H | H | 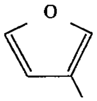 | H | 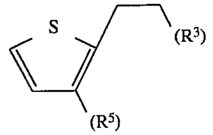 | H | $ClO_4$− |
| 120 | 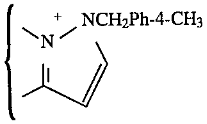 | H | $CH_3$ | Ph | H | Ph | H | $PF_6$− |
| 121 | 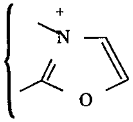 | H | $R^2-(CH_2)_2-R^3$ | Ph | — | Ph | H | $ClO_4$− |
| 122 | 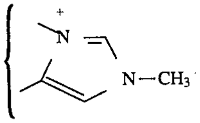 | H | H | 4-Br−Ph | H | 4-Br−Ph | H | $PF_6$− |

TABLE 3-continued
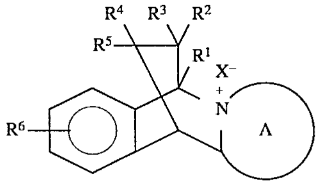
| Example Number | A | $R^1$ | $R^2$ | $R^4$ | $R^3$ | $R^5$ | $R^6$ | X− |
|---|---|---|---|---|---|---|---|---|
| 123 | 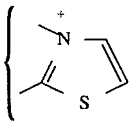 | $CH_3$ | H | 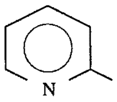 | H | 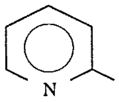 | H | $ClO_4$− |
| 124 | 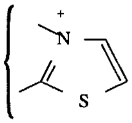 | n-Propyl | H | 4-$CH_3$−Ph | H | 4-$CH_3$−Ph | H | $ClO_4$− |
| 125 | 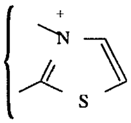 | H | H | 4-F−Ph | H | 4-F−Ph | 8-$OCH_3$ | $ClO_4$− |
| 126 | 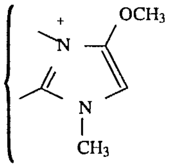 | H | H | 3-$CH_3O$−Ph | H | 3-$CH_3O$−Ph | H | $ClO_4$− |
| 127 | 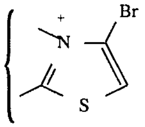 | H | H | 3-Br−Ph | H | 3-Br−Ph | 9-$OCH(CH_3)_2$ | $ClO_4$− |

TABLE 3-continued
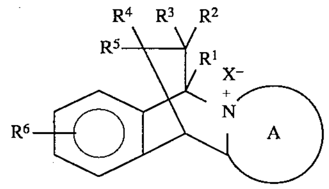
| Example Number | A | $R^1$ | $R^2$ | $R^4$ | $R^3$ | $R^5$ | $R^6$ | X− |
|---|---|---|---|---|---|---|---|---|
| 128 | 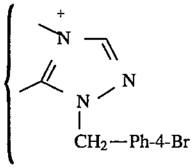 | H | H | 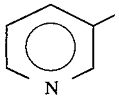 | H | 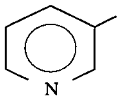 | 7,9-$F_2$ | $ClO_4$− |
| 129 | 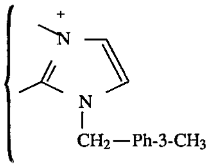 | H | H | 4-Cl−Ph | H | 4-Cl−Ph | 8-$CF_3$ | $PF_6$− |
| 130 | 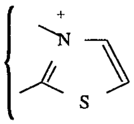 | H | H | 4-$CH_3O$−Ph | H | 4-$CH_3O$−Ph | 6,9-$Br_2$ | $ClO_4$− |
| 131 | 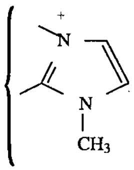 | H | H | 3-$CF_3$−Ph | H | 3-$CF_3$−Ph | 8-$CCl_3$ | $ClO_4$− |
| 132 | 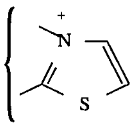 | H | H | 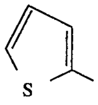 | H | 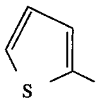 | 8,9-$OCH_2O$− | $ClO_4$− |

TABLE 3-continued
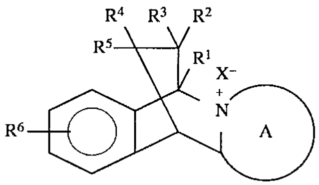
| Example Number | A | $R^1$ | $R^2$ | $R^4$ | $R^3$ | $R^5$ | $R^6$ | X− |
|---|---|---|---|---|---|---|---|---|
| 133 | 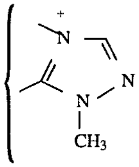 | H | H | 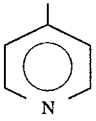 | H | 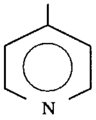 | 8-$NO_2$ | $ClO_4$− |
| 134 | 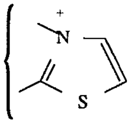 | H | H | 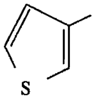 | H | 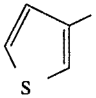 | 9-$CH_3$ | $ClO_4$− |
| 135 | 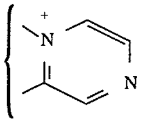 | H | H | 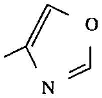 | H | 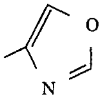 | 9-$OCH_3$ | $ClO_4$− |
| 136 | 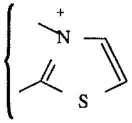 | H | H | 3-Cl−Ph | H | 3-Cl−Ph | 6,7,8,9-$F_4$ | $ClO_4$− |
| 137[(a)] | 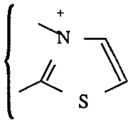 | H | H | C≡CH | H | Ph | 6,7,8-$(OCH_3)_3$ | Br− |
| 138 | 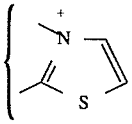 | H | H | 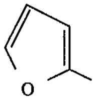 | H | 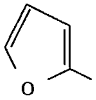 | 7-Br,8-$CH_3$ | $ClO_4$− |

TABLE 3-continued
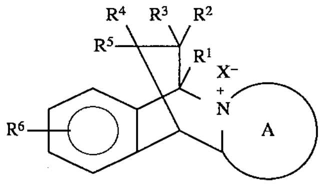
| Example Number | A | $R^1$ | $R^2$ | $R^4$ | $R^3$ | $R^5$ | $R^6$ | X− |
|---|---|---|---|---|---|---|---|---|
| 139[b] | 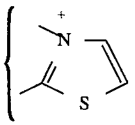 | H | H | 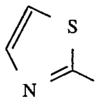 | H | 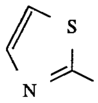 | 9-OH | Br− |
| 140 | 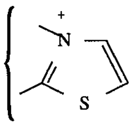 | H | H | 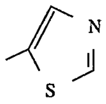 | H | 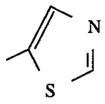 | 9-OC(O)$CH_3$ | Br− |
| 141 | 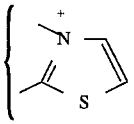 | H | H | $OCH_2CH_3$ | $CH_3$ | 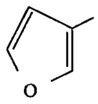 | H | $ClO_4$− |
| 142 | 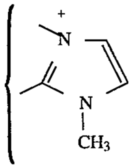 | H | H | 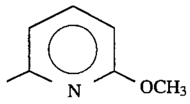 | H | 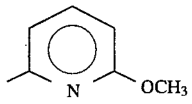 | H | $ClO_4$− |
| 143[c] | 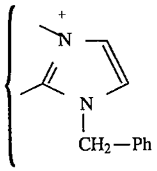 | H | H | 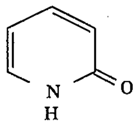 | H | 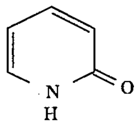 | H | $ClO_4$− |

TABLE 3-continued
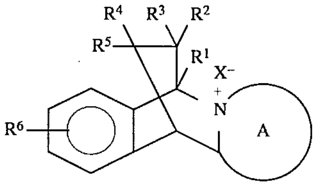
| Example Number | A | $R^1$ | $R^2$ | $R^4$ | $R^3$ | $R^5$ | $R^6$ | X− |
| --- | --- | --- | --- | --- | --- | --- | --- | --- |
| 144 | 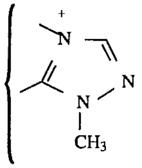 | H | H | 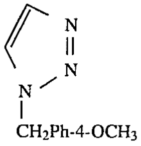 | H | 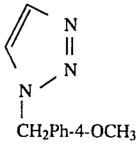 | H | $ClO_4^-$ |
| 145(d) | 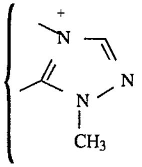 | H | H | 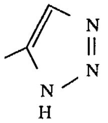 | H | 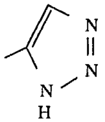 | H | $ClO_4^-$ |
| 146 | 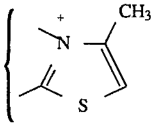 | H | H | 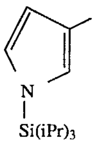 | H | 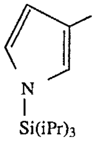 | H | $ClO_4^-$ |
| 147(e) | 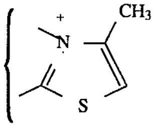 | H | H | 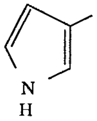 | H | 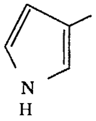 | H | $ClO_4^-$ |
| 148(f) | 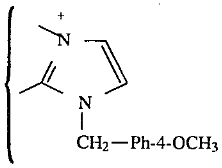 | H | $=CH_2$ | $OCH_2CH_3$ | — | 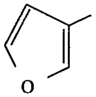 | H | $PF_6^-$ |

TABLE 3-continued
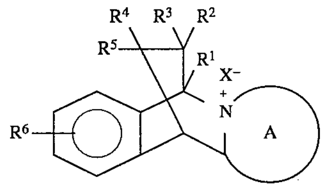
| Example Number | A | R¹ | R² | R⁴ | R³ | R⁵ | R⁶ | X− |
|---|---|---|---|---|---|---|---|---|
| 149 | 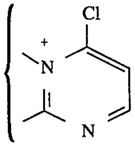 | H | H | 3-HO−Ph | H | 3-HO−Ph | H | $ClO_4$− |
| 150 | 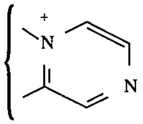 | $CH_3$ | H | 3-$CCl_3$−Ph | H | 3-$CCl_3$−Ph | H | $ClO_4$− |
| 151 | 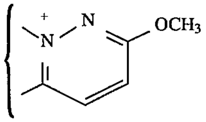 | H | H | 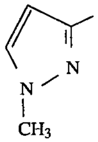 | H | 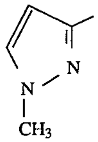 | H | $ClO_4$− |
| 152 | 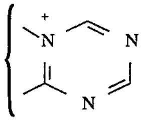 | H | H | 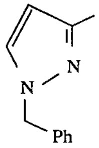 | H | 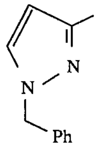 | H | $ClO_4$− |
| 153 | 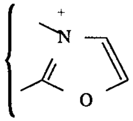 | H | H | 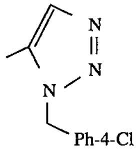 | H | 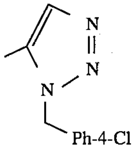 | H | $ClO_4$− |

TABLE 3-continued
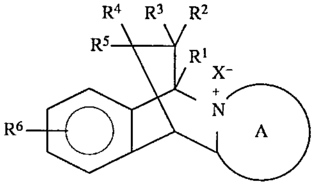
| Example Number | A | R¹ | R² | R⁴ | R³ | R⁵ | R⁶ | X− |
|---|---|---|---|---|---|---|---|---|
| 154 | 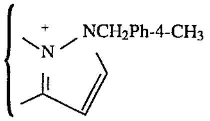 | H | H | 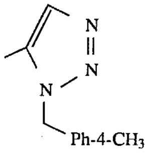 | H | 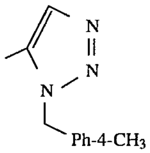 | H | $PF_6^-$ |
| 155 | 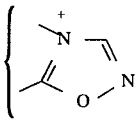 | H | H | 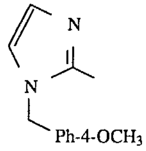 | H | 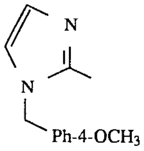 | H | $ClO_4^-$ |
| 156 | 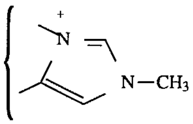 | H | H | 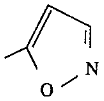 | H | 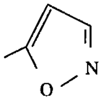 | H | $PF_6^-$ |
| 157 | 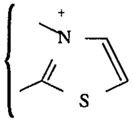 | $CH_3$ | H | 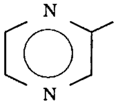 | H | 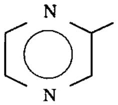 | H | $ClO_4^-$ |
| 158 | 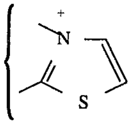 | n-propyl | H | 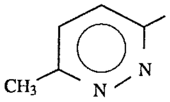 | H | 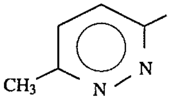 | H | $ClO_4^-$ |

TABLE 3-continued
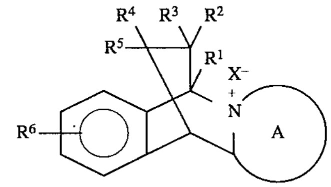
| Example Number | A | $R^1$ | $R^2$ | $R^4$ | $R^3$ | $R^5$ | $R^6$ | X− |
|---|---|---|---|---|---|---|---|---|
| 159 | 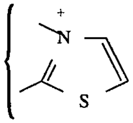 | H | H | 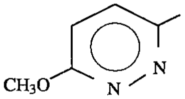 | H | 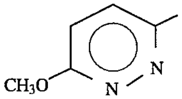 | 8-$OCH_3$ | $ClO_4$− |
| 160 | 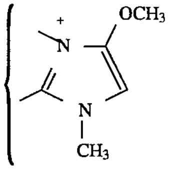 | H | H | 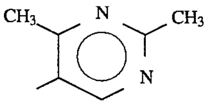 | H | 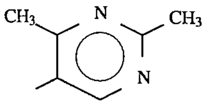 | H | $ClO_4$− |
| 161 | 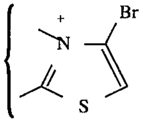 | H | H | 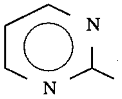 | H | 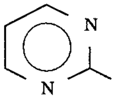 | 9-$OCH(CH_3)_2$ | $ClO_4$− |
| 162 | 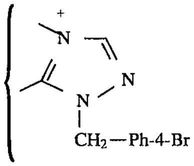 | H | H | 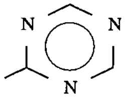 | H | 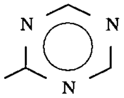 | 7,9-$F_2$ | $ClO_4$− |
| 163 | 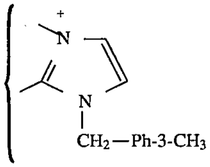 | H | H | 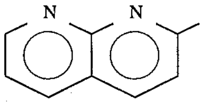 | H | 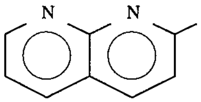 | 8-$CF_3$ | $PF_6$− |

TABLE 3-continued
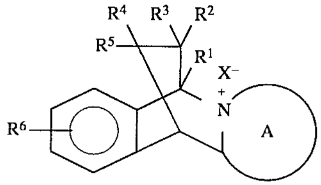
| Example Number | A | R¹ | R² | R⁴ | R³ | R⁵ | R⁶ | X− |
|---|---|---|---|---|---|---|---|---|
| 164 | 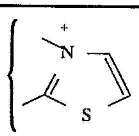 | H | H | 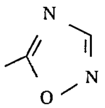 | H | 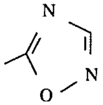 | 6,9-$Br_2$ | $ClO_4$− |
| 165 | 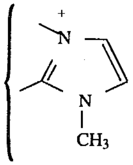 | H | H | 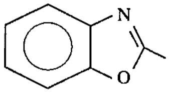 | H | 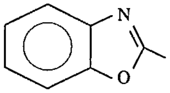 | 8-$CCl_3$ | $ClO_4$− |
| 166 | 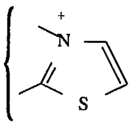 | H | H | 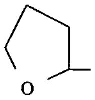 | H | 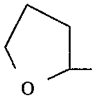 | H | $ClO_4$− |
| 167 | 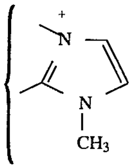 | H | H | 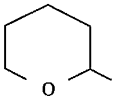 | H | 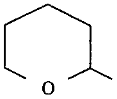 | H | $ClO_4$− |
| 168 | 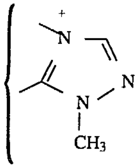 | H | H | Ph | H | 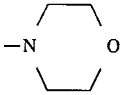 | H | $ClO_4$− |

TABLE 3-continued
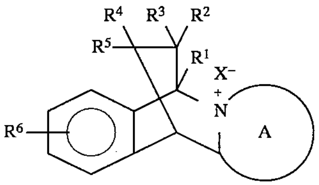
| Example Number | A | R¹ | R² | R⁴ | R³ | R⁵ | R⁶ | X− |
|---|---|---|---|---|---|---|---|---|
| 169 | 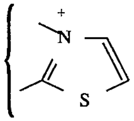 | H | H | 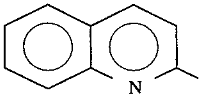 | H | 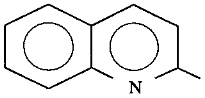 | 8,9-$OCH_2O$− | $ClO_4$− |
| 170 | 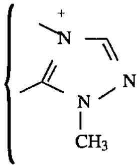 | H | H | 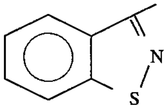 | H | 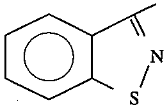 | 8-$NO_2$ | $ClO_4$− |
| 171 | 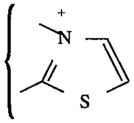 | H | H | 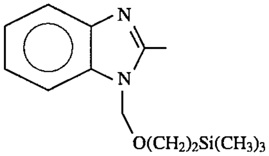 | H | 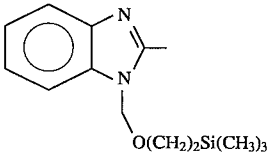 | 9-$CH_3$ | $ClO_4$− |
| 172 | 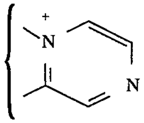 | H | H | 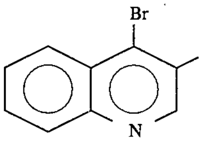 | H | 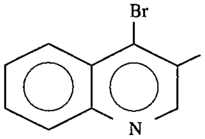 | 9-$OCH_3$ | $ClO_4$− |
| 173 | 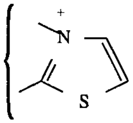 | H | H | 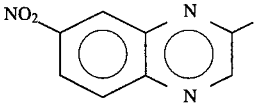 | H | 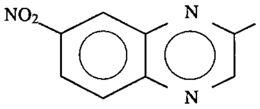 | 6,7,8,9-$F_4$ | $ClO_4$− |

TABLE 3-continued
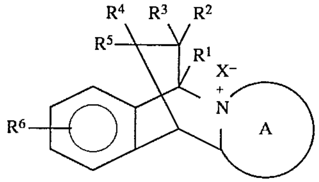
| Example Number | A | $R^1$ | $R^2$ | $R^4$ | $R^3$ | $R^5$ | $R^6$ | X− |
|---|---|---|---|---|---|---|---|---|
| 174 | 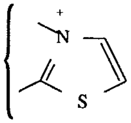 | H | H | 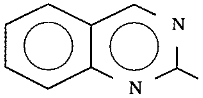 | H | 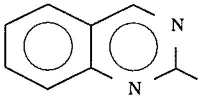 | 6,7,8-$(OCH_3)_3$ | $ClO_4$− |
| 175 | 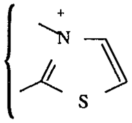 | H | H | 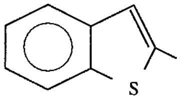 | H | 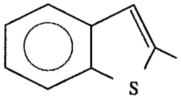 | 7-Br,8-$CH_3$ | $ClO_4$− |
| 176 | 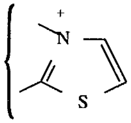 | H | H | 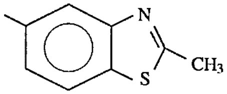 | H | 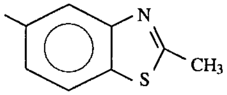 | H | $ClO_4$− |
| 177 | 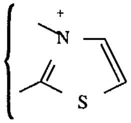 | H | H | 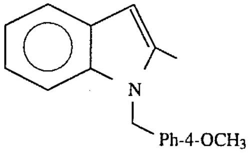 | H | 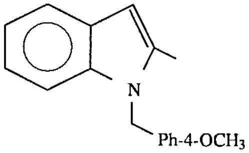 | H | $ClO_4$− |
| 178[(g)] | 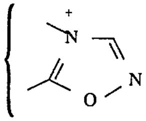 | H | H | 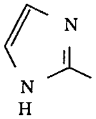 | H | 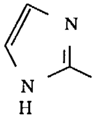 | H | $ClO_4$− |
| 179[(h)] | 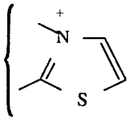 | H | H | 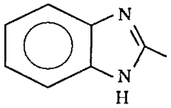 | H | 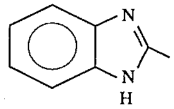 | 9-$CH_3$ | $ClO_4$− |

TABLE 3-continued
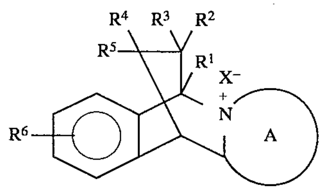
| Example Number | A | $R^1$ | $R^2$ | $R^4$ | $R^3$ | $R^5$ | $R^6$ | X− |
|---|---|---|---|---|---|---|---|---|
| 180[(i)] | 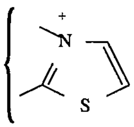 | H | H | 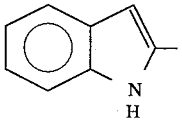 | H | 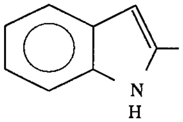 | H | $ClO_4-$ |
| 181 | 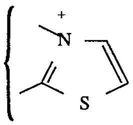 | H | H | 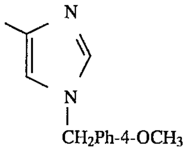 | H | 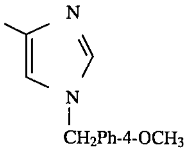 | H | $ClO_4-$ |
| 182 | 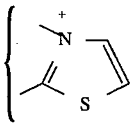 | H | H | 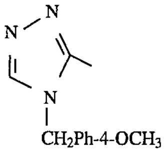 | H | 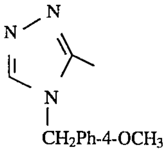 | H | $ClO_4-$ |
| 183 | 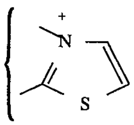 | H | H | 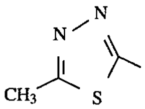 | H | 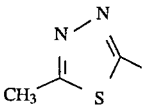 | H | $ClO_4-$ |
| 184 | 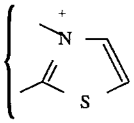 | H | H | 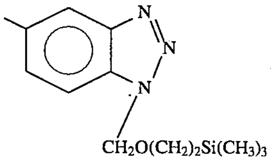 | H | 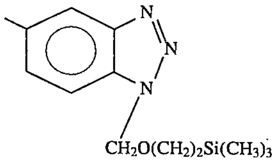 | H | $ClO_4-$ |

TABLE 3-continued
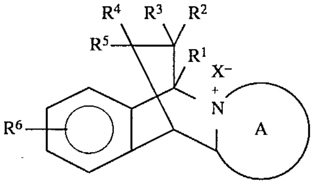
| Example Number | A | $R^1$ | $R^2$ | $R^4$ | $R^3$ | $R^5$ | $R^6$ | X− |
|---|---|---|---|---|---|---|---|---|
| 185 | 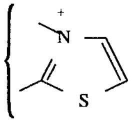 | H | H | 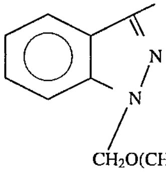 $CH_2O(CH_2)_2Si(CH_3)_3$ | H | 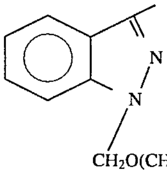 $CH_2O(CH_2)_2Si(CH_3)_3$ | H | $ClO_4$− |
| 186[j] | 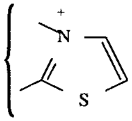 | H | H | 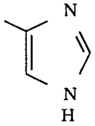 | H | 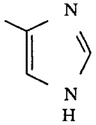 | H | $ClO_4$− |
| 187[k] | 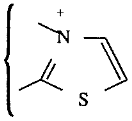 | H | H | 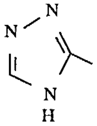 | H | 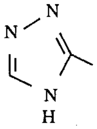 | H | $ClO_4$− |
| 188[l] | 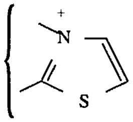 | H | H | 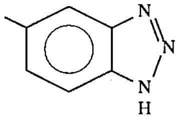 | H | 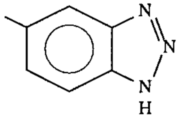 | H | $ClO_4$− |
| 189[m] | 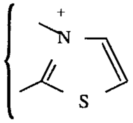 | H | H | 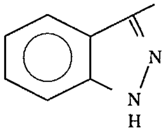 | H | 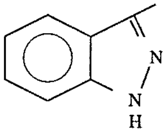 | H | $ClO_4$− |

TABLE 3-continued
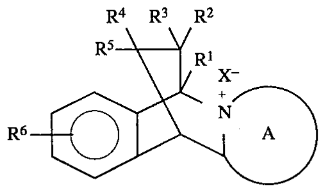
| Example Number | A | $R^1$ | $R^2$ | $R^4$ | $R^3$ | $R^5$ | $R^6$ | X− |
|---|---|---|---|---|---|---|---|---|
| 190 | 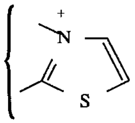 | H | H | Ph | H | Ph | 8-CN | $ClO_4$− |
| 191[n] | 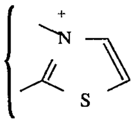 | H | H | Ph | H | Ph | 8-$CO_2H$ | $ClO_4$− |
| 192[o] | 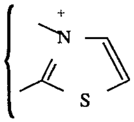 | H | H | Ph | H | Ph | 8-[C(O)OPr] | $ClO_4$− |
| 193[p] | 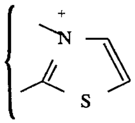 | H | H | Ph | H | Ph | 8-[C(O)O$(CH_2)_{15}CH_3$] | $ClO_4$− |
| 194[o] | 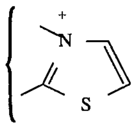 | H | H | 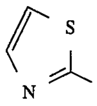 | H | 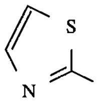 | 9-[OC(O)$(CH_2)_{15}CH_3$] | Br− |
| 195[r] | 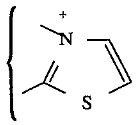 | H | H | 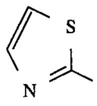 | H | 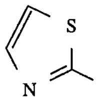 | 9-[OC(O)$(C_2H_5)$] | Br− |

TABLE 3-continued
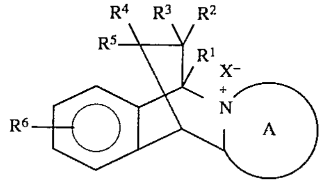
| Example Number | A | $R^1$ | $R^2$ | $R^4$ | $R^3$ | $R^5$ | $R^6$ | $X^-$ |
|---|---|---|---|---|---|---|---|---|
| 196[s] | 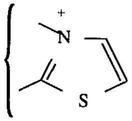 | H | H | 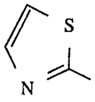 | H | 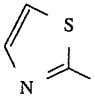 | 9-[OC(O)$(CH_2)_2$—C(O)$OC_2H_5$] | Br− |
| 197[t] | 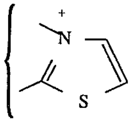 | H | H | 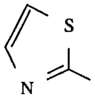 | H | 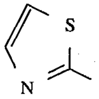 | 9-[OC(O)$(CH_2)_2$C(O)—O$(CH_2)_{15}CH_3$] | Br− |
| 198[u] | 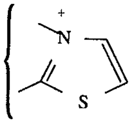 | H | H | 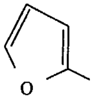 | H | 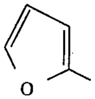 | 7-$PO_3H$-8-$CH_3$ | $ClO_4$− |
| 208[v] | 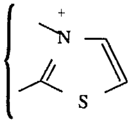 | H | H | 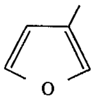 | H | 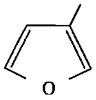 | 9-OC(O)$(CH_2)_7$—CH=CH—$(CH_2)_7CH_3$ | Cl− |
| 209[w] | 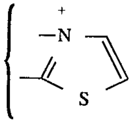 | H | H | 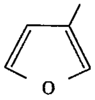 | H | 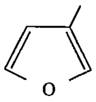 | 9-OC(O)CH=CHC(O)OEt | Cl− |
| 210[x] | 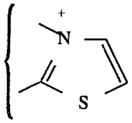 | H | H | 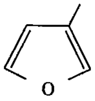 | H | 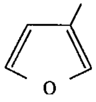 | 9-O$(CH_2)_7CH_3$ | Cl− |

TABLE 3-continued
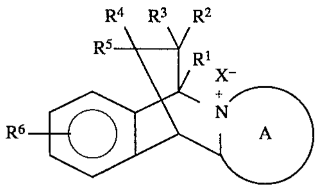
| Example Number | A | $R^1$ | $R^2$ | $R^4$ | $R^3$ | $R^5$ | $R^6$ | X− |
|---|---|---|---|---|---|---|---|---|
| 211[y] | 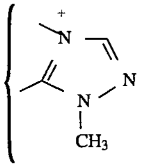 | H | H | 4-pyridyl | H | 4-pyridyl | 8-$NHSO_2CH_3$ | $ClO_4$− |
| 212[z] | 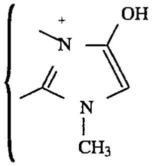 | H | H | 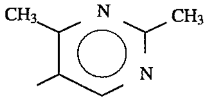 | H | 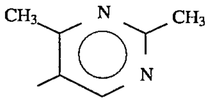 | H | $ClO_4$− |
| 213[aa] | 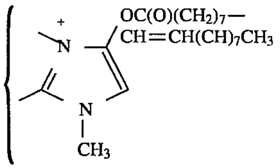 | H | H | 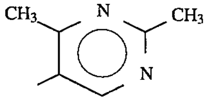 | H | 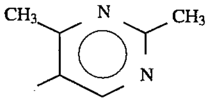 | H | $ClO_4$− |
| 214[ab] | 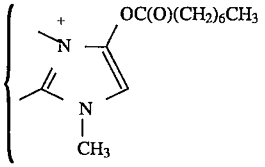 | H | H | 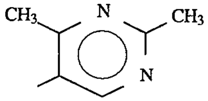 | H | 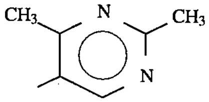 | H | $ClO_4$− |

TABLE 3-continued

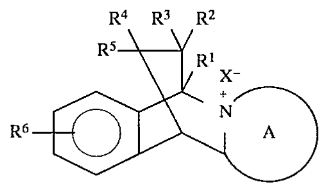

| Example Number | A | $R^1$ | $R^2$ | $R^4$ | $R^3$ | $R^5$ | $R^6$ | X− |
|---|---|---|---|---|---|---|---|---|
| 215[ae] | 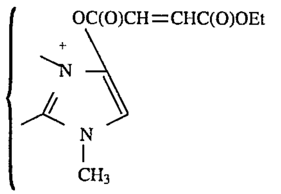 | H | H | 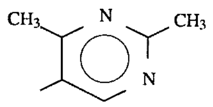 | H | 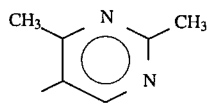 | H | $ClO_4$− |
| 216[ad] | 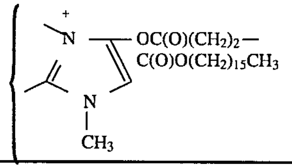 | H | H | 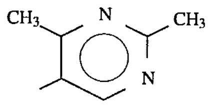 | H | 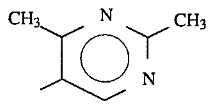 | H | $ClO_4$− |

[a]Olefin of Formula III which was used was (1-phenyl-1-ethynyl)ethylene which can be prepared in situ by the addition of p-toluenesulfonic acid to a mixture of 1-phenyl-1-ethynylmethanol and the heterocyclyl[1,2-b]isoquinolinium salt.
[b]Olefin of Formula III which was used was 1,1-Di(2-thiazolyl)ethylene which can be prepared in situ by the addition of p-toluenesulfonic acid to a mixture of 1,1-Di(2-thiazolyl)-2-trimethylsilylethanol and the heterocyclic[1,2-b] isoquinolinium salt.
[c]Prepared by treating the compound of Example 142 with 48% HBr at about 90° C.
[d]Prepared by treating the compound of Example 144 with trifluoroacetic acid.
[e]Prepared by treating the compound of Example 146 in $CH_2CL_2$ with tetrabutylammonium bromide.
[f]Olefin of Formula III which was used was 1-(3-furanyl)-1-ethoxyallene which can be prepared in situ by the addition of potassium t-butoxide to a mixture of 1-(3-furanyl)-1-ethoxy-2-propyne, and the heterocyclyl[1,2-b]isoquinolinium salt.
[g]Prepared by treating the compound of Example 155 with trifluoroacetic acid.
[h]Prepared by treating the compound of Example 171 in dichloroethane with trifluoroacetic acid.
[i]Prepared by treating the compound of Example 177 with trifluoroacetic acid.
[j]Prepared by treating the compound of Example 181 with trifluoroacetic acid.
[k]Prepared by treating the compound of Example 182 with trifluoroacetic acid.
[l]Prepared by treating the compound of Example 184 in dichloroethane with trifluoroacetic acid.
[m]Prepared by treating the compound of Example 185 in dichloroethane with trifluoroacetic acid.
[n]Prepared by treatment of the compound of Example 190 with aqueous sodium hydroxide containing 6–12% $H_2O_2$.
[o]Prepared by treating the compound of Example 191 with propanol in the presence of dicyclohexylcarbodimide.
[p]Prepared by treating the compound of Example 191 with hexadecanol in the presence of dicyclohexylcarbodimide.
[q]Prepared by treating the compound of Example 139 with heptadecanoyl chloride.

TABLE 3-continued

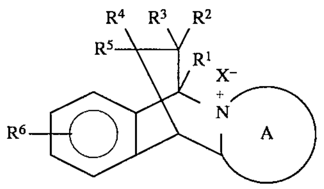

| Example Number | A | $R^1$ | $R^2$ | $R^4$ | $R^3$ | $R^5$ | $R^6$ | X− |
|---|---|---|---|---|---|---|---|---|

[r]Prepared by treating the compound of Example 139 with propionyl chloride.
[s]Prepared by treating the compound of Example 139 with ethylsuccinyl chloride.
[t]Prepared by treating the compound of Example 139 with hexadecylsuccinyl cloride.
[u]Prepared by treatment of the compound of Example 138 with diethylphosphite in the presence of a source of Pd(O), followed by hydrolysis with aqueous hydrochloric acid.
[v]Prepared by treating the compound of Example 206(f) with an excess of $ClC(O)(CH_2)_7CH=CH-(CH_2)_7CH_3$ in the presence of cesium carbonate.
[w]Prepared by treating the compound of Example 206(f) with an excess of $ClC(O)CH=CHCO_2CH_2CH_3$ in the presence of cesium carbonate.
[x]Prepared by treating the compound of Example 206(f) with an excess octyl bromide in the presence of cesium carbonate.
[y]Prepared by treating the compound of Example 133 with stannous chloride in aqueous hydrochloric acid, followed by treating the 8-amino derivative thus formed with methanesulfonyl chloride.
[z]Prepared by treating the compound of Example 160 with 48% HBr.
[aa]Prepared by treating the compound of Example 212 with an excess of $ClC(O)(CH_2)_7CH=CH-(CH_2)_7CH_3$ in the presence of cesium carbonate.
[ab]Prepared by treating the compound of Example 212 with an excess of $ClC(O(CH_2)_6CH_3$ in the presence of cesium carbonate.
[ac]Prepared by treating the compound of Example 212 with an excess of $ClC(O)CH=CHCO_2CH_2CH_3$ in the presence of cesium carbonate.
[ad]Prepared by treating the compound of Example 212 with hexadecylsuccinyl chloride in the presence of cesium carbonate.

EXAMPLE 199

(a)

To a solution of n-butyllithium (2.43 g, 38 mmol, 2.5M in hexane) in 100 ml of ether under argon at −78° C. was added dropwise in 1 h a solution of 1-phenylimidazole (5 g, 35 mmol). The mixture was stirred at −78° C. for 1 h, and then a solution of DMF (2.54 g, 35 mmol) in ether (70 ml) was added. The mixture was stirred for 1 h at −78° C., then at −15° C. for 18 h. The reaction mixture was then extracted with 4N HCl (4×20 ml), the aqueous layers were combined, cooled in an ice-bath, and neutralized with solid sodium bicarbonate. The aqueous layer was extracted with ether (4×35 ml), the organic layer was dried over sodium sulfate and concentrated in vacuo to afford 5.6 g (90%) of 1-phenyl-2-imidazolyl-carboxaldehyde.

(b)

A mixture of 1-phenyl-2-imidazolylcarboxaldehyde (5.6 g, 33 mmol), 4.1 g (66 mmol) of ethylene glycol, 150 ml of toluene and 1.9 g (10 mmol) of p-toluenesulfonic acid monohydrate under argon in a 3 neck-flask equipped with a Dean-Stark trap was refluxed for 6 h separating the water formed. The mixture was cooled to room temperature and poured into an ice-cold 10% sodium carbonate solution. The aqueous layer was extracted with ether, the combined organic layer was washed with brine, dried over sodium sulfate, and concentrated in vacuo to afford 6.1 g of 1-phenyl-2-(1,3-dioxolan-2-yl)imidazole (Formula V: A=1-phenylimidazole; Y=2-(1,3-dioxolan-2-yl).

(c)

A reaction mixture of 6.1 g (28.24 mmol) of 1-phenyl-2-(1,3-dioxalan-2-yl)imidazole and 4.83 g (28.24 mmol) of benzyl bromide was stirred at room temperature for 6 h, triturated with ether, decanted and dried to afford 9.8 g of 3-benzyl-2-(1,3-dioxolan-2-yl)-1-phenylimidazolium bromide (Formula VI: A=1-phenyl-imidazolyl; Y=2(1,3-dioxolan-2-yl); $R^1$=$R^6$=H; $Z^-$=$Br^-$).

(d)

A mixture of 3-benzyl-2-(1,3-dioxolan-2-yl)-1-phenylimidazolium bromide (9.8 g) and 100 ml of 48% HBr was heated on a steam-bath with stirring for 5 h. The mixture was cooled to room temperature, concentrated in vacuo, and the resulting brown residue was redissolved in water. The aqueous solution was filtered and the the filtrate was treated with 10% sodium perchlorate solution. The precipitated product was filtered, washed with water and ether, and dried in vacuo to afford 6.3 g of 1-phenylimidazolo[1,2 -b]isoquinolin-4-ium perchlorate (Formula II: A=1-phenylimidazo; $R^1$=$R^6$=H; $X^-$=$ClO_4^-$), m.p. 208°–210° C. (from methanol).

(e)

A reaction mixture containing 1-phenylimidazo[1,2-b]isoquinolin-4-ium perchlorate (3.44 g; 10 mmol) and 1,1-di(3-furyl)ethylene (2.4 g; 15 mmol) in 75 ml of acetonitrile was allowed to reflux under argon with stirring for 48 h. The reaction mixture was concentrated in vacuo, the residue was passed through a silica column (methylene chloride/methanol, 20:1) to afford 3.2 g (63%) of 11,11-di(3-furyl)-5,10-ethano-5,10-dihydro-1-phenyl-imidazo[1,2-b]isoquinolin-4-ium perchlorate (Formula I: A=1-phenylimidazo; $R^1$=$R^2$=$R^3$=$R^6$=H; $R^4$=$R^5$=3-furyl; $X^-$=$ClO_4^-$).

(f)

11,11-Di(3-furyl)-5,10-ethano-5,10-dihydro-1-phenyl-imidazo-[1,2-b]isoquinolin-4-ium perchlorate (3.2 g, 6.34 mmol) in acetonitrile was converted to the corresponding chloride by passing the salt through Dowex® 1×2-200($Cl^-$) (water/acetonitrile, 7:3). The salt was recrystallized from methylene chloride/ether to afford 1.8 g (64%) of 11,11-di(3-furyl)-5,10-ethano-5,10-dihydro-1-phenylimidazo [1,2-b]isoquinolin-4-ium chloride (Formula I: A=1-phenylimidazo; $R^1$=$R^2$=$R^3$=$R^6$=H; $R^4$=$R^5$=3-furyl; $X^-$=$Cl^-$).

EXAMPLE 200

(a)

To a stirred solution of imidazole (6.808 g, 0.1 mol) in dry DMF (100 ml) at 0° C. under argon was added portionwise 4 g (0.1 mol) of 60% sodium hydride and the mixture was stirred for 30 minutes at room temperature, and cooled to 0° C. To the above mixture was added 3-phenylpropyl bromide (19.91 g, 0.1 mol) and the resulting mixture was stirred at room temperature overnight. The reaction mixture was heated on a steam-bath for 4 hours and stirred at room temperature overnight. The solvent was concentrated in vacuo, the residue was partitioned between methylene chloride and water, the organic layer was dried over sodium sulfate, and concentrated in vacuo. The residual oil was dried in vacuo and purified by silica gel column chromatography to afford 16.1 g (86%) of 1-(3-phenylpropyl)imidazole.

(b)

To a solution of n-butyllithium (5.76 g, 90 mmol, 2.5M in hexane) in 200 ml of ether under argon at −78° C. was added dropwise in 1 hour a solution of 1-(3-phenylpropyl)imidazole (16 g, 86 mmol). The mixture was stirred at −78° C. for 1 h, and then a solution of DMF (9.87 g, 0.135 mol) in ether (15 ml) was added. The mixture was stirred for 1 h at −78° C., then at −15° C. for 18 h. The reaction mixture was then extracted with 4N HCl (4×20 ml), the aqueous layers were combined, cooled in an ice-bath, and neutralized with solid sodium bicarbonate. The aqueous layer was extracted with chloroform (4×100 ml), the organic layer was dried over sodium sulfate and concentrated in vacuo to afford 15 g (81%) of 1-(3-phenylpropyl)-2-imidazolylcarboxaldehyde.

(c)

A mixture of 1-(3-phenylpropyl)-2-imidazolyl-carboxaldehyde (16 g, 75 mmol), 9.27 g (150 mmol) of ethylene glycol, 200 ml of toluene and 3.8 g (10 mmol) of p-toluenesulfonic acid monohydrate under argon in a 3 neck-flask equipped with a Dean-Stark trap was refluxed for 6 h separating the water formed. The mixture was cooled to room temperature, and poured into an ice-cold 10% sodium carbonate solution. The aqueous layer was extracted with ether, the combined organic layer was washed with brine and dried over sodium sulfate, and concentrated in vacuo to afford 18.3 g of 1-(3-phenylpropyl)-2-(1,3-dioxolan-2-yl)imidazole (Formula V: A=1-(3-phenylpropyl)imidazole; Y=2-(1,3-dioxolan-2-yl).

(d)

A reaction mixture of 18 g (70 mmol) of 1-(3-phenylpropyl)-2-(1,3-dioxolan-2-yl)imidazole and 11.93 g (70 mmol) of benzyl bromide was stirred at room temperature for 8 h.

The mixture was triturated with ethyl acetate, decanted and dried to afford 26.1 g (87%) of 3-benzyl-2-(1,3-dioxolan-2-yl)-1-(3-phenylpropyl)imidazolium bromide (Formula VI: A=1-(3-phenylpropyl)imidazole; Y=2-(1,3-dioxolan-2-yl; $R^1$=$R^6$=H; $Z^-$=$Br^-$).

(e)

A mixture of 3-benzyl-2-(1,3-dioxolan-2-yl)-1-(3-phenylpropyl)imidazolium bromide (26 g) and 200 ml of 48% HBr was heated on an oil-bath (120°–130° C.) with stirring for 48 h. The mixture was cooled to room temperature, concentrated in vacuo, and the resulting brown residue was redissolved in water. The aqueous solution was filtered and the filtrate was treated with an aqueous $KPF_6$ solution. The precipitated product was filtered, dissolved in acetonitrile and concentrated, and the mixure was dried in vacuo to afford 28.6 g of 1-(3-phenylpropyl)imidazo-[1,2-b]isoquinolin-4-ium hexafluorophosphate (Formula II: A=1-(3-phenylpropyl) imidazole; $R^1$=$R^6$=H; $X^-$=$PF_6^-$) which was recrystallized from methylene chloride/ethyl acetate.

(f)

A reaction mixture containing 1-(3-phenylpropyl)imidazo-[1,2-b]isoquinolin-4-ium hexafluoro-phosphate (4.32 g; 10 mmol) and 1,1-di(3-furyl)ethylene (2.4 g; 15 mmol) in 125 ml of acetonitrile was allowed to reflux under argon with stirring for 48 h. The reaction mixture was concentrated in vacuo, the residue was passed through a silica column (methylene chloride/methanol, 20:1) to afford 2.8 g of 11,11-di(3-furyl)-5,10-ethano-5,10-dihydro-1-(3-phenylpropyl) imidazo[1,2-b]isoquinolin-4-ium hexafluoro phosphate (Formula I: A=1-(3-phenylpropyl)-imidazole; $R^1$=$R^2$=$R^3$=$R^6$=H; $R^4$=$R^5$=3-furyl; $X^-$=$PF_6^-$).

(g)

11,11-Di(3-furyl)-5,10-ethano-5,10-dihydro-1-(3-phenylpropyl) imidazo[1,2-b]isoquinolin-4-ium hexafluoro-phosphate (2.8 g, 4.73 mmol) in acetonitrile was converted to the corresponding chloride by passing the salt through Dowex® 1×2-200($Cl^-$) (water/acetonitrile, 1:1). The salt was recrystallized from methylene chloride/ether and dried in vacuo to afford 1.3 g (57%) of 11,11-di(3-furyl)-5,10-ethano-5,10-dihydro-1-(3-phenylpropyl) imidazo[1,2-b]isoquinolin-4-ium chloride (Formula I: A=1-(3-phenylpropyl)imidazole; $R^1$=$R^2$=$R^3$=$R^6$=H; $R^4$=$R^5$=3-furyl; $X^-$=$Cl^-$).

EXAMPLE 201

(a)

To a solution of n-butyllithium (13.45 g, 0.21 mol, 2.5M in hexane) in 150 ml of ether under argon at −78° C. was added dropwise in 1 hour a solution of 1-butylimidazole (25 g, 0.2 mol). The mixture was stirred at −78° C. for 1 h, and then a solution of DMF (15.35 g, 0.21 mol) in ether (50 ml) was added. The mixture was stirred for 1 h at −78° C., then at −15° C. for 18 h. The reaction mixture was then extracted with 4N HCl (4×20 ml), the aqueous layers were combined, cooled in an ice-bath, and neutralized with solid sodium bicarbonate. The aqueous layer was extracted with ether (4×35 ml), the organic layer was dried over sodium sulfate and concentrated in vacuo to afford 28.6 g (93%) of 1-butyl-2-imidazolylcarboxaldehyde.

(b)

A mixture of 1-butyl-2-imidazolylcarboxaldehyde (28.6 g, 190 mmol), 23.56 g (380 mmol) of ethylene glycol, 250 ml of toluene and 9 g (50 mmol) of p-toluenesulfonic acid monohydrate under argon in a 3 neck-flask equipped with a Dean-Stark trap was refluxed for 6 h separating the water formed. The mixture was cooled to room temperature, and poured into an ice-cold 10% sodium carbonate solution. The aqueous layer was extracted with ether, the combined organic layer was washed with brine, dried over sodium sulfate, and concentrated in vacuo to afford 19.3 g of 1-butyl-2-(1,3-dioxolan-2-yl)imidazole (Formula V: A=1-butyl-2-imidazole; Y=2-(1,3-dioxolan-2-yl).

(c)

A reaction mixture of 19.3 g (104 mmol) of 1-butyl-2-(1,3-dioxolan-2-yl)imidazole and 17.75 g (104 mmol) of benzyl bromide was stirred at room temperature for 24 h. The mixture was triturated with ethyl aceate, decanted and dried to afford 35.3 g of 3-benzyl-2-(1,3-dioxolan-2-yl)-1-butyl-imidazolium bromide (Formula VI: A=1-butylimidazole; Y=2-(1,3-dioxolan-2-yl); $R^1$=$R^6$=H; $Z^-$=$Br^-$).

(d)

A mixture of 3-benzyl-2-(1,3-dioxolan-2-yl)-1-butyl-imidazolium bromide (35 g) and 300 ml of 48% HBr was heated on an oil-bath (120°–130° C.) with stirring for 48 h. The mixture was cooled to room temperature, concentrated in vacuo, and the resulting brown residue was redissolved in water. The aqueous solution was filtered and the filtrate was treated with an aqueous $KPF_6$ solution. The precipitated product was filtered, washed with water, washed with methanol, and dried in vacuo to afford 22.6 g (62%) of 1-butylimidazo[1,2-b]isoquinolin-4-ium hexafluorophosphate (Formula II: A=1-butylimidazole; $R^1$=$R^6$=H; $X^-$=$PF_6^-$) which was recrystallized from methanol.

(e)

A reaction mixture containing 1-butylimidazo-[1,2-b]isoquinolin-4-ium hexafluorophosphate (3.7 g; 10 mmol) and 1,1-di(3-furyl)ethylene (1.92 g; 10 mmol) in 75 ml of acetonitrile was allowed to reflux under argon with stirring for 4 days. The reaction mixture was concentrated in vacuo, the residue was triturated with ether. The residue was redissolved in acetonitrile, treated with activated charcoal and filtered. The filtrate was concentrated in vacuo to afford 4.3 g of 11,11-di(3-furyl)-5,10-ethano-5,10-dihydro-1-butylimidazo-[1,2 -b]isoquinolin-4-ium hexafluorophosphate (Formula I: A=1-butylimidazole; $R^1$=$R^2$=$R^3$=$R^6$=H; $R^4$=$R^5$=3-furyl; $X^-$=$PF_6^-$).

(f)

11,11-Di(3-furyl)-5,10-ethano-5,10-dihydro-1-butyl-imidazo[1,2-b]isoquinolin-4-ium hexafluorophosphate (4.3 g, 8.11 mmol) in acetonitrile was converted to the corresponding chloride by passing the salt through Dowex® 1×2-200($Cl^-$) (water/acetonitrile, 1:1). The salt was recrystallized from methylene chloride/ether and dried in vacuo to afford 3.8 g of 11,11-di(3-furyl)-5,10-ethano-5,10-dihydro-1-butylimidazo-[1,2-b]isoquinolin-4-ium chloride (Formula I: A=1-butylimidazole; $R^1$=$R^2$=$R^3$=$R^6$=H; $R^4$=$R^5$=3-furyl; $X^-$=$Cl^-$) which was further purified by dissolving the product in methylene chloride, filtering, and concentrating the filtrate in vacuo. The above purification process was repeated with water.

EXAMPLE 202

(a)

A mixture of 1-benzyl-2-(1,3-dioxolan-2-yl)-3-benzylimidazolium bromide (17.3 g) and 450 ml of 48% HBr was heated on an oil-bath (120°–130° C.) and stirred for 48 h. The mixture was concentrated in vacuo at 60° C. and the resulting green colored residue was redissolved in water. The aqueous solution was treated with a sodium perchlorate (2 equiv) solution and the precipitated product was separated by decanting, and crystallized from $CH_3CNEtOAC$. The solid product was collected by filtration, washed with ethanol and dried in vacuo to afford 18.6 g of 1-benzylimidazo [1,2-b]isoquinolin-4-ium perchlorate (Formula II: A=1-benzylimidazole; $R^1$=$R^6$=H; $X^-$=$ClO_4^-$).

(b)

A reaction mixture containing 1-benzylimidazo-[1,2-b] isoquinolin-4-ium perchlorate (2.0 g; 5.58 mmol) and 1,1-di[(1-p-methoxybenzyl)pyrazol-3-yl]ethylene (2.23 g; 5.58 mmol) in 50 ml of nitromethane was allowed to reflux under argon with stirring for 24 hours. The reaction mixture was concentrated in vacuo, the residue was purified by silica gel column chromatography to afford 2.5 g (59%) of 11,11-di [(1-p-methoxybenzyl)pyrazol-3-yl]-5,10-ethano-5,10-dihydro-1-benzylimidazo-[1,2-b]isoquinolin-4-ium perchlorate (Formula I: A=1-benzylimidazole; $R^1$=$R^2$=$R^3$=$R^6$=H; $R^4$=$R^5$=1-p-methoxybenzyl-3-pyrazolyl; $X^-$=$ClO_4^-$).

(c)

A solution of 11,11-di[(1-p-methoxybenzyl)pyrazol-3-yl] -5,10-ethano-5,10-dihydro-1-benzylimidazo-[1,2-b]isoquinolin-4-ium perchlorate (2.5 g, 3.3 mmol) in 25 ml of trifluoroacetic acid was refluxed with stirring under argon for 48 hours. The mixture was concentrated in vacuo, the residue was dissolved in water and acetonitrile and the salt was converted to the corresponding chloride by passing the salt through Dowex® 1×2-200($Cl^-$) (water and acetonitrile, 1:1). The salt was triturated in isopropanol and the solid was dried in vacuo to afford 0.45 g (32%) of 11,11-di(pyrazol-3-yl)-5,10-ethano-5,10-dihydro-1-benzylimidazo-[1,2-b] isoquinolin-4-ium chloride (Formula I: A=1-benzylimidazole; $R^1$=$R^2$=$R^3$=$R^6$=H; $R^4$=$R^5$=3-pyrazolyl; $X^-$=$Cl^-$), m.p. 204°–206° C.

EXAMPLE 203

(a)

To a stirred solution of 2-imidazolylcarboxaldehyde (9.6 g, 0.1 mol) in dry THF (200 ml) at 0° C. under argon was added portionwise 4 g (0.1 mol) of 60% sodium hydride and the mixture was stirred at 0° C. for 15 minutes and at room temperature for 2 hours, and cooled to 0° C. To the above mixture was added diphenylmethyl chloride (20.27 g, 0.1 mol) in 15 ml of THF and the resulting mixture was stirred at room temperature for 3 days. The reaction mixture was heated in an oil-bath at 60°–70° C. for 24 hours. The solvent was concentrated in vacuo, the residue was dissolved in methylene chloride and washed with water. The organic layer was dried over sodium sulfate, concentrated in vacuo, and the residual oil was passed through a silica column (methylene chloride/ether, 9:1) and crystallized from methylene chloride/hexane to afford 10.8 g (39%) of 1-(1,1-diphenylmethyl)-2-imidazolyl-carboxaldehyde.

(b)

To a solution of 7.48 g (0.04 mol) of 2-bromobenzyl alcohol in 250 ml of ether at −40° C. was added in portions 2.5M n-butyllithium (5.12 g, 0.08 mol) in hexane followed by 4.65 g (0.04 mol) of TMEDA, and the reaction mixture was slowly (removing the bath) warmed to room temperature and stirred for 1 hour. The above reaction mixture was cooled to −20° C., 10.8 g (0.041 mol) of 1-(1,1-diphenylmethyl)-2-imidazolyl carboxaldehyde in 50 ml of ether was added, and the resulting reaction mixture was allowed to warm to room temperature. After 1 hour ammonium chloride solution was added to the mixture. The diol was extracted with ethyl acetate, dried over sodium sulfate, and the solvent was removed in vacuo. The residue was triturated with ethyl acetate to afford 6.3 g (42%) of 1-(1,1-diphenylmethyl)-2-[1-hydroxy-(2'-hydroxymethyl)-benzyl] imidazole (Formula IX: A=1-(1,1-diphenylmethyl)imidazole; $R^1$=$R^6$=H).

(c)

A mixture of 6.2 g (16.75 mmol) of 1-(1,1-diphenylmethyl)-2-[1-hydroxy-(2'-hydroxymethyl)-benzyl]imidazole and 40 ml of $POCl_3$ was refluxed with stirring for 4 h. The mixture was cooled, poured into ice, and the mixture was stirred overnight. The resulting dark solution was filtered through a filter pad, and treated with a $KPF_6$ solution. The resulting solid was filtered, washed, and dried to afford 0.7 g of 1-(1,1-diphenylmethyl)-imidazo[1,2-b]isoquinolin-4-ium hexafluorophosphate (Formula II: A=1-(1,1-diphenylmethyl)-imidazole; $R^1$=$R^6$=H; $X^-$=$PF_6^-$).

(d)

A reaction mixture containing 1-(1,1-diphenylmethyl)-imidazo[1,2-b]isoquinolin-4-ium hexafluorophosphate (0.7 g; 1.46 mmol) and 1,1-di(3-furyl)-ethylene (0.3 g; 1.75 mmol) in 20 ml of nitromethane was allowed to reflux under argon with stirring for 4 days. The reaction mixture was concentrated in vacuo, the residue was passed through a silica gel column (methylene chloride/methanol, 9:1) and recrystallized from methylene chloride/ether to afford 200 mg of 11,11-di(3-furyl)-5,10ethano-5,10-dihydro-1-(1,1-diphenylmethyl)imidazo[1,2-b]isoquinolin-4-ium hexafluorophosphate (Formula I: A=1-(1,1-diphenylmethyl)-imidazole; $R^1$=$R^2$=$R^3$=$R^6$=H; $R^4$=$R^5$=3-furyl; $X^-$=$PF_6^-$).

EXAMPLE 204

(a)

A mixture of imidazole (15.4 g, 0.226 mol) and 2-bromomethylnaphthalene (22 g, 0.0995 mol) in 200 ml of methylene chloride was stirred at room temperature overnight. The mixture was stirred with 200 ml of water, the organic layer was washed with water (2×200 ml), and stirred with 30 ml of conc. HCl and 200 ml of water. After filtration for the removal of the solid, the methylene chloride layer was discarded, and the aqueous layer was extracted with 200 ml of ether. The above aqueous layer was basified with 3N NaOH solution, extracted with methylene chloride, and the organic layer was dried over magnesium sulfate. The above organic solution was concentrated in vacuo to afford 13.65 g of 1-(2-naphthylmethyl)imidazole, m.p. 87°–88° C.

(b)

To a solution of n-butyllithium (28 ml, 70 mmol, 2.5M in hexane) in 150 ml of THF and 150 mL ether under argon at −78° C. was added dropwise in 1 hour a solution of 1-(2-naphthylmethyl)-imidazole (13.65 g, 65.6 mmol) in 50 ml of ether/THF (1:1). The mixture was stirred at −78° C. for 1 h, and then a solution of DMF (5.59 ml, 72 mmol) in ether (10 ml) was added. The mixture was stirred for 1 h at −78° C., then at room temperature overnight. The reaction mixture was then extracted with 4N HCl (4×30 ml), the aqueous layers were combined, cooled in an ice-bath, and neutralized with sodium bicarbonate solution. The aqueous layer was extracted with chloroform (4×50 ml), the organic layer was dried over magnesium sulfate and concentrated in vacuo to yield an amber oil. The oil was purified by silica gel column (ethyl acetate/hexane, 1:1) and recrystallized from ethyl acetate/hexane to afford 6.38 g of 1-(2-naphthylmethyl)-2-imidazolylcarboxaldehyde, m.p. 89°–90° C.

(c)

To a mixture of 5.24 g (0.028 mol) of 2-bromobenzyl alcohol in 100 ml of ether and 10 ml TMEDA cooled to −30° C. was added dropwise 26.4 ml (66 mmol) of 2.5M n-butyllithium in hexane. The reaction mixture was stirred at −30° C. for one hour, then the reaction mixture was slowly (removing a bath) warmed to room temperature and stirred for one hour. The above reaction mixture was cooled to −20° C., 6 g (66 mmol) of 1-(2-naphthylmethyl)-2-imidazolylcarboxaldehyde in 50 ml of ether was added, and the resulting reaction mixture was allowed to warm to room temperature overnight. An ammonium chloride solution was added to the mixture. The diol was extracted with ethyl acetate, dried over sodium sulfate, and the solvent was removed in vacuo. The residue crystallized from ethyl acetate/hexane to afford 4.3 g of 1-(2-naphthyl-methyl)-2-[1-hydroxy-(2'-hydroxymethyl)-benzyl]imidazole (Formula IX: A=1-(2-naphthylmethyl)imidazole; $R^1$=$R^6$=H), m.p. 153°–154° C.

(d)

A mixture of 3.6 g of 1-(2-naphthylmethyl)-2-[1-hydroxy-(2'-hydroxymethyl)-benzyl]imidazole and 25 ml of $POCl_3$ was heated to reflux and stirred overnight. The mixture was poured onto ice, treated with an excess of a sodium perchlorate solution, and the product was extracted with methylene chloride. The organic layer was dried over magnesium sulfate and concentrated in vacuo to afford 1.2 g of 1-(2-naphthylmethyl)imidazo[1,2-b]isoquinolin-4-ium perchlorate (Formula II: A=1-(2-naphthylmethyl) imidazole; $R^1$=$R^6$=H; $X^-$=$ClO_4^-$).

(e)

A reaction mixture containing 1-(2-naphthylmethyl)-imidazo[1,2-b]isoquinolin-4-ium perchlorate (1.2 g; 3.88 mmol) and 1,1-di(3-furyl)ethylene (1 g; 6.25 mmol) in 20 ml of acetonitrile and 20 ml ethanol was heated to reflux and stirred overnight. The reaction mixture was concentrated in vacuo and the residue was dissolved in $CH_2Cl_2$ and passed through a silica column (2:1 methylene chloride/ethyl acetate). Evaporation gave the product as the perchlorate salt. This product then was passed through a Dowex® 1X2-200($Cl^-$) ion exchange column to afford 340 mg of 11,11-di(3-furyl)-5,10-ethano-5,10-dihydro-1-(2-naphthylmethyl)imidazo[1,2-b]isoquinolin-4-ium chloride (Formula I: A=1-(2-naphthylmethyl)imidazole; $R^1$=$R^2$=$R^3$=$R^6$=H; $R^4$=$R^5$=3-furyl; $X^-$=$Cl^-$), m.p. 220°–225° C.

EXAMPLE 205

(a)

A mixture of imidazole (15.4 g) and 1-chloromethylnaphthalene (14.9 ml, 0.1 mol) in 200 ml of methylene chloride was stirred at room temperature overnight. The mixture was stirred with 200 ml of water, the layers were separated, the organic layer was washed with water (2×200 ml), the resulting solids were removed by filtration and then the organic layer was stirred with 30 ml of conc. HCl and 200 ml of water. The methylene chloride layer was discarded, and the aqueous layer was extracted with 100 ml of ether. The above aqueous layer was basified with 3N NaOH solution, extracted with methylene chloride, and the organic layer was dried over magnesium sulfate. The above organic solution was concentrated in vacuo to afford 13.58 g of 1-(1-naphthylmethyl)imidazole.

(b)

To a solution of n-butyllithium (28 ml, 2.5M in hexane) in 150 ml of THF and 150 ml ether under argon at −78° C. was added dropwise in 1 hour a solution of 1-(1-naphthylmethyl)imidazole (13.58 g) in 50 ml of ether and THF (1:1). The mixture was stirred at −78° C. for 1 h, and then a solution of DMF (5.59 ml, 72 mmol) in ether (10 ml) was added. The mixture was stirred for 1 h at −78° C., then at room temperature overnight. The reaction mixture was then extracted with 4N HCl (4×30 ml), the aqueous layers were combined, cooled in an ice-bath, and neutralized with sodium bicarbonate solution. The aqueous layer was extracted with chloroform (4×50 ml), the organic layer was dried over magnesium sulfate and concentrated in vacuo to yield an amber oil. The oil was purified by chromatography on silica gel column (ethyl acetate/hexane, 1:1) and recrystallized from ethyl acetate/hexane to afford 3.05 g of 1-(1-naphthylmethyl)-2-imidazolylcarboxaldehyde, m.p. 88°–89° C.

(c)

To a solution of 2.618 g (0.014 mol) of 2-bromobenzyl alcohol in 50 ml of ether and 4.97 ml (33 mmol) of TMEDA cooled to −30° C. was added in portions 13.2 ml (33 mmol) of 2.5M n-butyllithium in hexane and the reaction mixture was slowly (removing a bath) warmed to room temperature and stirred. The above reaction mixture was cooled to −20° C., 3 g (12.7 mol) of 1-(1-naphthylmethyl)-2-imidazolyl carboxaldehyde in 50 ml of ether was added, and the resulting reaction mixture was allowed to warm to room temperature. An ammonium chloride solution was added to the mixture, and the diol was extracted with ethyl acetate, dried over magnesium sulfate, and the solvent was removed in vacuo. The residue was recrystallized from ethyl acetate/hexane to afford 0.92 g of 1-(1-naphthylmethyl)-2-[1-hydroxy-(2-hydroxymethyl)-benzyl]imidazole (Formula IX: A=1-(1-naphthylmethyl) imidazole; $R^1$=$R^6$=H), m.p. 190°–191° C.

(d)

A mixture of 2.58 g of 1-(1-naphthylmethyl)-2-[1-hydroxy-(2'-hydroxymethyl)-benzyl]imidazole and 25 ml of $POCl_3$ was heated to reflux and stirred overnight. The mixture was poured onto ice, the solution was treated with a sodium perchlorate solution, and the resulting solid was extracted with methylene chloride. The organic layer was dried over magnesium sulfate and concentrated in vacuo to afford 2.9 g of 1-(1-naphthylmethyl)imidazo[1,2-b]isoquinolin-4-ium perchlorate (Formula II: A=1-(1-naphthylmethyl)imidazole; $R^1$=$R^6$=H; $X^-$=$ClO_4^-$).

(e)

A reaction mixture containing 1-(1-naphthylmethyl)-imidazo[1,2-b]isoquinolin-4-ium perchlorate (2.9 g; 9.4 mmol) and 1,1-di(3-furyl)ethylene (2.56 g; 16 mmol) in 20 ml of acetonitrile and ethanol (20 ml) was heated to reflux and stirred overnight. The reaction mixture was concentrated in vacuo, the residue was passed through a silica column (methylene chloride/ethyl acetate) to afford, on evaporation, the product as the perchlorate salt which was then passed through a Dowex® 1×2-200($Cl^-$) ion exchange column to afford 1.306 g of 11,11-di(3-furyl)-5,10-ethano-5,10-dihydro-1-(1-naphthylmethyl)imidazo[1,2-b]isoquinolin-4-ium chloride (Formula I: A=1-(1-naphthylmethyl)imidazole; $R^1$=$R^2$=$R^3$=$R^6$=H; $R^4$=$R^5$=3-furyl; $X^-$=$Cl^-$), m.p. 165° C.

EXAMPLE 206

(a)

To a solution of n-butyllithium (10.05, 157 mmol, 2.5M in hexane) in 200 ml of ether under argon at −78° C. was added dropwise in 1 hour a solution of 2-bromothiazole (25 g, 157 mmol) in 200 ml of ether. The mixture was stirred at −78° C. for 1 h, and then a solution of DMF (11.14 g, 152 mmol) in ether (50 ml) was added. The mixture was stirred for 1 h at −78° C., then at −15° C. overnight. The reaction mixture was then extracted with 4N HCl (4×20 ml), the aqueous layers were combined, cooled in an ice-bath, and neutralized with sodium bicarbonate solution. The aqueous layer was extracted with ether (4×35 ml), the organic layer was dried over sodium sulfate and concentrated in vacuo to afford 15.2 g of 2-thiazolylcarboxaldehyde.

(b)

To a mixture of 15.75 g (0.12 mol) of 3-methoxybenzyl alcohol in 100 ml of ether cooled to −30° C. under argon was added in portions 15.37 g (240 mmol) of 2.5M n-butyllithium in hexane followed by 13.95 g (120 mmol) of TMEDA, and the reaction mixture was slowly warmed to room temperature and stirred. The above reaction mixture was cooled to −20° C., 15 g (132 mmol) of 2-thiazolylcarboxaldehyde in 50 ml of ether was added, and the resulting reaction mixture was allowed to warm to room temperature. After 1 hour ammonium chloride solution was added to the mixture. The diol was extracted with ethyl acetate, dried over sodium sulfate, and the solvent was removed in vacuo to yield an oil. The residue was purified by silica gel column chromatography (methylene chloride/methanol, 20:1) to afford 15 g (52%) of 2-[1-hydroxy-(2'-hydroxymethyl-6'-methoxy)-benzyl]thiazole (Formula IX: A=2-thiazole; $R^1$=H; $R^6$-6'-$OCH_3$).

(c)

A mixture of 15 g (60 mmol) of 2-[1-hydroxy-(2'-hydroxy-methyl-6'-methoxy)benzyl]thiazole and 90 ml of $POCl_3$ was refluxed with stirring for 18 hours. The mixture was cooled, poured into ice, and the mixture was stirred overnight. The resulting dark solution was filtered through a filter pad, treated with sodium perchlorate solution, and the resulting solid was extracted with methylene chloride. The organic layer was dried over magnesium sulfate and concentrated in vacuo to afford 10.1 g (53%) of 9-methoxy-thiazolo[3,2-b]isoquinolinium perchlorate (Formula II: A=thiazolo; $R^1$=H; $R^6$=9-$OCH_3$; $X^-$=$ClO_4^-$).

(d)

A mixture of 9-methoxy-thiazolo[3,2-b]isoquinolinium perchlorate (7 g, 22.19 mmol) in 100 ml of 48% HBr was heated for 18 hours at 115° C. The mixture was concentrated in vacuo, the residue was dissolved in warm water and filtered. The filtrate was treated with sodium perchlorate, the resulting solid was filtered, and washed with water to afford 1.0 g (15%) of 9-hydroxy-thiazolo[3,2-b]isoquinolinium perchlorate (Formula II: A=thiazolo; $R^1$=H; $R^6$=9-OH; $X^-$=$ClO_4^-$).

(e)

A reaction mixture containing 9-hydroxy-thiazolo[3,2-b]isoquinolinium perchlorate (0.9 g; 2.98 mmol) and 1,1-di(3-furyl)ethylene (0.64 g; 4 mmol) in 40 ml of ethanol/acetonitrile (3:1) was allowed to reflux under argon with stirring for 24 h and cooled to room temperature. The reaction mixture was concentrated in vacuo, the residue was passed through a silica column (methylene chloride/methanol, 9:1) to afford 1.0 g of 11,11-di(3-furyl)-9-hydroxy-5,10-ethano-5,10-dihydro-thiazolo[3,2-b]isoquinolinium perchlorate (Formula I: A=thiazolo; $R^1$=$R^2$=$R^3$=H; $R^6$=9-OH; $X^-$=$ClO_4^-$).

(f)

11,11-Di(3-furyl)-9-hydroxy-5,10-ethano-5,10-dihydrothiazolo-[3,2-b]isoquinolinium perchlorate (1.0 g, 2.17 mmol) in acetonitrile was converted to the corresponding chloride by passing the salt through Dowex® 1×2-200($Cl^-$) (water/acetonitrile, 1:1). The salt was redissolved in water, filtered, and concentrated in vacuo to afford 0.7 g (60%) of 11,11-di(3-furyl)-9-hydroxy-5,10-ethano-5,10-dihydrothiazolo[3,2-b]isoquinolinium chloride (Formula I: A=thiazolo; $R^1$=$R^2$=$R^3$=H; $R^6$=9-OH; $X^-$=$Cl^-$).

EXAMPLE 207

(a)

A reaction mixture containing 9-methoxy-thiazolo[3,2-b]isoquinolinium perchlorate (1.5 g; 4.75 mmol) and 1,1-di(3-furyl)ethylene (0.95 g; 5.94 mmol) in 30 ml of ethanol/acetonitrile (5:1) was allowed to reflux under argon with stirring for 48 h and cooled to room temperature. The reaction mixture was concentrated in vacuo, the residue was passed through a silica gel column (methylene chloride/methanol, 9:1) to afford 2.1 g of 11,11-di(3-furyl)-9-methoxy-5,10-ethano-5,10-dihydro-thiazo[3,2-b]isoquinolinium perchlorate (Formula I: A=thiazolo; $R^1$=$R^2$=$R^3$=H; $R^6$=9-$OCH_3$; $X^-$=$ClO_4^-$).

(b)

11,11-Di(3-furyl)-9-methoxy-5,10-ethano-5,10-dihydrothiazolo-[3,2-b]isoquinolinium perchlorate (2.1 g, 4 mmol) in acetonitrile was converted to the corresponding chloride by passing the salt through Dowex® 1×2-200 ($Cl^-$) (water/acetonitrile, 1:1). The salt was redissolved in water, filtered, and concentrated in vacuo to afford 0.4 g of 11,11-di(3-furyl)-9-methoxy-5,10-ethano-5,10-dihydrothiazolo[3, 2-b]isoquinolinium chloride (Formula I: A=thiazolo; $R^1$=$R^2$=$R^3$=H; $R^6$=9-$OCH_3$; $X^-$=$Cl^-$).

BIOLOGICAL TEST RESULTS

Representative examples of the compounds of the invention have been found to possess valuable pharmacological properties. In particular, they have been found to bind to the PCP receptor and are thus non-competitive blockers (antagonists) of the effects which excitatory amino acids, such as glutamate, have upon the NMDA receptor. The compounds of the invention are thus useful in the treatment or prevention of neurodegenerative disorders such as Huntington's disease, Alzheimer's disease, amyotrophic lateral sclerosis, Down's Syndrome, senile dementia, glutaric acidaemia type I, multi-infarct dementia, Parkinson's disease, viral encephalopathies (which include, but are not limited thereto, dementia associated with HIV infections) and neuronal damage associated with uncontrolled seizures, as well as in the treatment or prevention of neurotoxic injuries associated with ischemic, hypoxic; or hypoglycemic conditions. Representative examples of such ischemic, hypoxic, or hypoglycemic conditions include strokes or cerebrovascular accidents, carbon monoxide poisoning, hyperinsulinemia, cardiac arrest, drownings, suffocation, spinal or head trauma, coronary artery bypass graft, neonatal anoxic trauma, and perinatal asphyxia.

The compounds of the invention are particularly useful in the treatment or prevention of neurotoxic injuries associated with ischemic, hypoxic; or hypoglycemic conditions, and especially ischemic, hypoxic, or hypoglycemic conditions which are associated with stroke.

The pharmacological properties of representative examples of the compounds of the invention was demonstrated by conventional in vitro and in vivo biological test procedures such as the following:

[$^3$H]TCP Radioreceptor Assay

[$^3$H]TCP binding to PCP recognition sites was performed as described by Vignon et al. Brain Research 1983, 280, 194–197. Male Sprague-Dawley rats were sacrificed by decapitation, and whole brains were homogenized in 10 volumes (wt/vol) of cold Tris-HCl buffer (50 mM, pH 7.7) using a Brinkmann Polytron (setting 6, 30 sec). The homogenate was centrifuged at 40,000 x g for 10 min at 4° C. The supernatant was decanted, and the homogenization and centrifugation steps were repeated twice as described above. Following this, the pellet was resuspended in Tris-HCl (5 mM, pH 7.7) at a tissue concentration of 0.5–0.75 g/ml, and one ml aliquots were frozen at −70° C. until use. The binding characteristics for PCP recognition sites were not altered by the freezing of membrane suspensions.

On the day of the assay, membrane aliquots were thawed, resuspended in fresh 5 mM Tris-HCl buffer at a tissue concentration of 1 mg/ml, and stored on ice until use. Each assay tube contained 100 μl of [$^3$H]TCP at a final concentration of approximately 1 nM, 100 μl of various concentrations of the compounds of interest, 500 μl of the tissue suspension and 300 μl of buffer to a final assay volume of 1 ml and a final protein concentration of 0.5 mg/tube. Nonspecific binding was defined by addition of a final concentration of 100 μM PCP to blank tubes. All tubes were incubated at room temperature for 25 min before termination of the reaction by rapid filtration over Whatman GF/B glass fiber filters that had been presoaked in a solution of 0.5% polyethylenimine for at least 1 hr prior to use. Filters were washed with three 4 ml volumes of cold Tris buffer. Following addition of scintillation cocktail, the amount of bound radioactivity was determined by liquid scintillation spectrometry using a Beckman LS 5000TA liquid scintillation counter with an efficiency for tritium of approximately 55%. Inhibition constants ($K_i$ values) were calculated using the EBDA/LIGAND program (McPherson, J. Pharmacol. Meth. 1985, 14, 213–228), purchased from Elsevier/Biosoft, Inc. The results are reported as $K_i$ values (in nM) which are expressed as the mean of at least two separate determinations, or as a percent (%) inhibition of binding at 10 μM.

Antagonism of NMDA-induced Neurotoxicity in Cultured Neurons

Preparation of Cultured Cortical Neurons

Pregnant, Swiss-Webster mice were obtained from Taconic Farms (Germantown, N.Y.) and sacrificed 16 days post conception. Fetuses were removed and placed in a sterile dish containing Hank's balanced salt solution (HBSS), pH 7.4. Brain cortices were dissected, meninges were removed, the tissue was minced and placed into a solution of HBSS containing 0.25% (w/v) trypsin at 37° C. for 15 minutes. Tissue was then triturated with a sterile pasteur pipet, diluted with minimal essential media (Gibco 330-1430), pH 7.4, supplemented with 10% horse serum, 10% fetal calf serum, 2 mM 1-glutamine, 21 mM d-glucose, 2.2 g/L sodium bicarbonate, 1000 U/ml penicillin, and 1,000 μg/ml streptomycin. Cells were plated onto Falcon primaria 96 well plates at a final density of 50,000 cells/well and incubated at 37° C. in the presence of 5% (v/v) carbon dioxide. After 5 days, plating media was replaced with maintenance media containing minimal essential media (Gibco 330-1430), pH 7.4, supplemented with 10% horse serum, 10% 1-glutamine, 21 mM D-glucose, 2.2 g/l sodium bicarbonate, 1,000 U/ml penicillin, 1,000 μg/ml streptomycin, and 10 μM cytosine arabinoside. On days 7 and 10, media was replaced with maintenance media as above lacking the cytosine arabinoside. Experiments were conducted on day 13.

Neuroprotection Assessment

Day 13 cultured cortical neurons were washed twice with minimal essential media, pH 7.4 and then exposed for 30 minutes to 500 μM N-methyl-D-aspartic acid (NMDA) with or without varying concentrations of test agents. Dizocilpine (MK-801) at a final concentration of 10 μM MK-801 was routinely included as a positive control. MK-801 and test agents were prepared in minimal essential media supplemented with 21 mM d-glucose and 2.2 g/L sodium bicarbonate (MEM). After 30 minutes, media was replaced with MEM alone. Exposure of neurons to test agents was limited to the NMDA treatment period. Twenty-four hours after removal of NMDA, an aliquot of media from each well was removed for assessment of cell injury by determining lactate dehydrogenase (LDH) activity by the method of Wroblewski and LaDue Proc. Soc. Exp. Biol. Med. 1955, 90, 210–213. The results are expressed as an $IC_{50}$ (in nM) value (concentration causing 50% inhibition) for the antagonism of NMDA—induced neurotoxicity.

Table 4 summarizes the results obtained from the testing of representative compounds of the invention in the [$^3$H] TCP radioreceptor assay as well as in the antagonism of NMDA-induced neurotoxicity in cultured neurons.

TABLE 4

| Example Number | [$^3$H]TCP $K_i$(nM) or Percent inhibition @ 10 μM | Antagonism of NMDA-induced neurotoxicity ($IC_{50}$ in nM) |
|---|---|---|
| 1i | 6.1 | 173 |
| 2(b) | 4.2 | — |
| 3(b) | 13 | — |
| 4(e) | 2.9 | 50 |
| 5(c) | 5.0 | 32 |
| 5(e) | 2.0 | 20 |
| 6(d) | 9.2 | 79 |
| 7(F) | 8.2 | 53 |
| 8(b) | 10 | — |
| 9(b) | 89 | — |
| 10(b) | 30 | — |
| 11(g) | 35 | — |
| 2(F) | 7.7 | — |
| 13(b) | 2.9 | 257 |
| 14(E) | 14 | — |
| 15(F) | 20 | 300 |
| 16(E) | 11 | 270 |
| 17 | 640 | — |
| 18(h) | 21 | 480 |
| 19(F) | 30 | — |
| 18(e) | 6% | — |
| 199(f) | 52.2 | — |
| 200(g) | 67.8 | — |
| 201(f) | 36.3 | — |
| 202(c) | 36.5 | — |
| 203(d) | 306 | — |
| 204(e) | 330 | — |
| 205(e) | 329 | — |
| 206(f) | 1.87 | 20.9 |
| 207(b) | 14.1 | — |

Middle Cerebral Artery Occlusion (MCAO) Model with Reperfusion

A 3-vessel rat ischemia model similar to those that have been extensively described in the literature (e.g. Stroke 17, 738–743 (1986), Stroke 20, 513–518 (1989)) was utilized. Under isoflurane anesthesia the right middle cerebral artery (via an approach through the temporalis muscle) and both common carotid arteries were reversibly occluded for varying durations between 60 minutes and 120 minutes. Both male Long Evans hooded rats and male Sprague-Dawley rats weighing between 300 and 420 grams were used. The animals' temperature was maintained throughout the study with heat lamps. A femoral vein and the ipsilateral femoral artery were cannulated for intravenous infusion and arterial blood pressure measurements and blood samples. Infusions of the test compounds were initiated 30 minutes prior to occlusion at a rate of 40 microliters per minute. After reinitiation of blood flow the animals were allowed to regain consciousness. Six hours post-initiation of ischemia the animals were sacrificed and the extent of neuronal damage was quantified with TTC staining. The results are expressed as a percent inhibition (±SEM) of infarct and penumbra region.

Table 5 summarizes the results obtained from the testing of representative compounds of the invention in the MCAO model.

TABLE 5

| Example Number | Dose (mg Test Compound/ kg/min) | % Inhibition (+/− SEM) |
|---|---|---|
| 5e | 0.01 | 20 +/ 13 |
| | 0.03 | 11 +/ 19 |
| | 0.1 | 78 +/ 10 |

The compounds of the invention can be prepared for pharmaceutical use by conventional pharmaceutical procedures that are well known in the art; that is, by formulating a pharmaceutical composition which comprises compounds of the invention or their pharmaceutically acceptable salts together with one or more physiologically acceptable carriers, adjuvants, diluents or vehicles, for oral administration in solid or liquid form, parenteral administration, topical administration or aerosol inhalation administration, and the like.

Solid compositions for oral administration include compressed tablets, pills, powders and granules. In such solid compositions, the active compound is admixed with at least one inert diluent such as starch, calcium carbonate, sucrose or lactose. These compositions may also contain additional substances other than inert diluents, e.g., lubricating agents, such as magnesium stearate, talc and the like.

Liquid compositions for oral administration include pharmaceutically acceptable emulsions, solutions, suspensions, syrups and elixirs containing inert diluents commonly used in the art, such as water and liquid paraffin. Besides inert diluents such compositions may also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. These compositions can also contain adjuvants such as stabilizing, preserving, wetting, emulsifying and dispersing agents.

Preparations according to the invention for topical administration or aerosol inhalation administration include dissolving or suspending a compound of the invention in a pharmaceutically acceptable vehicle such as water, aqueous alcohol, glycol, oil solution or oil-water emulsion, and the like.

If desired, the compounds of the invention can further be incorporated into slow release or targeted delivery systems such as polymer matrices, liposomes, and microspheres.

The percentage of active component in such compositions may be varied so that a suitable dosage is obtained. The dosage administered to a particular patient is variable depending upon the clinician's judgment using as criteria: The route of administration, the duration of treatment, the size and physical condition of the patient, the potency of the active component and the patient's response thereto. An effective dosage amount of the active component can thus readily be determined by the clinician after a consideration of all criteria and using his best judgment on the patient's behalf.

We claim:

1. A method for the treatment or prevention of neurotoxic injuries which comprises administering to a patient in need of such treatment an effective amount of a compound of the formula:

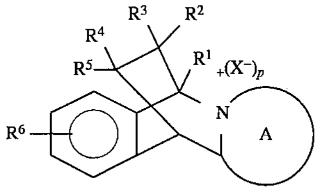

wherein:

$R^1$ is hydrogen, or lower-alkyl;

$R^2$ and $R^3$ are independently hydrogen, or lower-alkyl; or $R^2$ and $R^3$ together form a cycloalkyl ring, or a lower-alkylidene group;

$R^4$ and $R^5$ are independently lower-alkynyl, lower-alkoxy, phenyl (or phenyl substituted by lower-alkoxy, halogen, lower-alkyl, polyfluorolower-alkyl, polychlorolower-alkyl, or hydroxy), a 5- or 6-membered monocyclic aromatic heterocyclic ring system containing from one to three, the same or different, heteroatoms selected from the group consisting of nitrogen, oxygen and sulfur (or said 5- or 6-membered monocyclic aromatic heterocyclic ring system substituted on any available carbon atom thereof by hydroxy, lower-alkyl, oxo, nitro, halogen, or lower-alkoxy; or on any available nitrogen atom thereof by lower-alkyl, tri-lower-alkylsilyl, trilower-alkylsilyl-lower-alkoxy-lower-alkyl, or phenyl-lower-alkyl (or said phenyl-lower-alkyl group substituted on the phenyl group by lower-alkoxy, lower-alkyl or halogen)); a 9- or 10-membered bicyclic aromatic heterocyclic ring system containing from one to two, the same or different, heteroatoms selected from the group consisting of oxygen, nitrogen and sulfur (or said 9- or 10-membered bicyclic aromatic heterocyclic ring system substituted at any available carbon atom thereof by hydroxy, lower-alkyl, oxo, nitro, halogen, or lower-alkoxy; or on any available nitrogen atom thereof by lower-alkyl, trilower-alkylsilyl, trilower-alkylsilyl-lower-alkoxy-lower-alkyl, or phenyl-lower-alkyl (or said phenyl-lower-alkyl group substituted on the phenyl group by lower-alkoxy, lower-alkyl, or halogen)); or a 5- or 6-membered monocyclic nonaromatic heterocyclic ring system containing from one to two, the same or different, heteroatoms selected from the group consisting of nitrogen, oxygen and sulfur (or said 5- or 6-membered nonaromatic heterocyclic ring system substituted on any available carbon atom thereof by hydroxy, lower-alkyl, oxo, nitro, halogen, or lower-alkoxy, or on any available nitrogen atom thereof by lower-alkyl, trilower-alkylsilyl, trilower-alkylsilyl-lower-alkoxy-lower-alkyl, or phenyl-lower-alkyl (or said pheny-lower-alkyl group substituted on the phenyl group by lower-alkoxy, lower-alkyl or halogen));

or $R^2$ and $R^4$ and/or $R^3$ and $R^5$ taken together with the carbon atoms to which they are attached form a bicyclic ring system of the formula

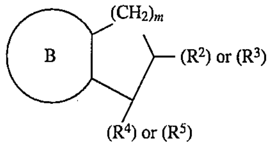

wherein B is:

phenyl, or a 5- or 6-membered monocyclic aromatic heterocyclic ring system containing from one to three, the same or different, heteroatoms selected from the group consisting of nitrogen, oxygen and sulfur, (or said B ring substituted on any available carbon atom thereof by lower-alkoxy, or lower-alkyl), and n is an integer from one to three;

$R^6$ is hydrogen, or from one to four, the same or different, substituents in any of the 7-, 8-, 9-, or 10-positions (if A is a six-membered ring), or in any of the 6-, 7-, 8-, or 9- position (if A is a five-membered ring) selected from the group consisting of lower-alkyl, lower-alkanoyloxy, halogen, nitro, hydroxy, lower-alkoxy, methylenedioxy, polychlorolower-alkyl, $OCO(CH_2)m$, C(O)O alkyl, OC(O)alkyl, C(O)Oalkyl, $CO_2^-$, carboxy, sulfo, $SO_3^-$, $PO_3H$, $PO_3^-$, cyano, polyfluorolower-alkyl, OC(O) alkyl-CH=CH-alkyl, OC(O)-lower-alkenyl-C(O)alkyl, alkoxy, OC(O)alkylC(O)Oalkyl, amino, and lower-alkylsulfonylamino, wherein m is an integer from one to four;

A together with the carbon and nitrogen atoms to which it is attached forms a 5- or 6-membered monocyclic aromatic heterocycle containing from two to three, the same or different, heteroatoms selected from the group consisting of nitrogen, oxygen and sulfur (or said 5- or 6-membered monocyclic aromatic heterocycle substituted on any available carbon atom thereof by hydroxy, OC(O)alkyl-CH=CH-alkyl, OC(O)alkyl, OC(O)lower-alkenyl-C(O)Oalkyl, alkoxy, OC(O)alkylC(O)Oalkyl, nitro, amino, lower-alkylsulfonylamino, lower-alkyl, lower-alkoxy, or halogen; or on any available nitrogen atom thereof by phenyl (or said phenyl group substituted by lower-alkoxy, lower-alkyl or halogen), diphenylmethyl, naphthyl-lower-alkyl (or said naphthyl-lower-alkyl group substituted on the naphthyl group by lower-alkoxy, lower-alkyl or halogen), lower-alkyl, or phenyl-lower-alkyl (or said phenyl-lower-alkyl group substituted on the phenyl group by lower-alkoxy, lower-alkyl or halogen));

$X^-$ is an anion; and p is zero when $R^6$ is a negatively charged radical, and p is one when $R^6$ is other than a negatively charged radical;

or a pharmaceutically acceptable acid-addition salt of basic members thereof; or a hydrate thereof; or a stereoisomer thereof.

2. A method according to claim 1 wherein:

$R^1$ is hydrogen, or lower-alkyl;

$R^2$ and $R^3$ are independently hydrogen, or lower-alkyl; or $R^2$ and $R^3$ together form a cycloalkyl ring, or a lower-alkylidene group;

$R^4$ and $R^5$ are independently lower-alkynyl, lower-alkoxy, phenyl (or phenyl substituted by lower-alkoxy, halogen, lower-alkyl, polyfluorolower-alkyl, polychlorolower-alkyl, or hydroxy), a 5- or 6-membered monocyclic aromatic heterocyclic ring system containing from one to three, the same or different, heteroatoms selected from the group consisting of nitrogen, oxygen and sulfur (or said 5- or 6-membered monocyclic aromatic heterocyclic ring system substituted on any available carbon atom thereof by lower-alkyl, oxo, nitro, halogen, or lower-alkoxy; or on any available nitrogen atom thereof by lower-alkyl, tri-lower-alkylsilyl, trilower-alkylsilyl-lower-alkoxy-lower-alkyl, or phenyl-lower-alkyl (or said phenyl-lower-alkyl group substituted on the phenyl group by lower-alkoxy, lower-alkyl or halogen)); a 9- or 10-membered bicyclic aromatic heterocyclic ring system containing from one to two, the same or different, heteroatoms selected from the group consisting of oxygen, nitrogen and sulfur (or said 9- or 10-membered bicyclic aromatic heterocyclic ring system substituted at any available carbon atom thereof by lower-alkyl, oxo, nitro, halogen, or lower-alkoxy; or on any available nitrogen atom thereof by lower-alkyl, trilower-alkylsilyl, trilower-alkylsilyl-lower-alkoxy-lower-alkyl, or phenyl-lower-alkyl (or said phenyl-lower-alkyl group substituted on the phenyl group by lower-alkoxy, lower-alkyl, or halogen)); or a 5- or 6-membered monocyclic nonaromatic heterocyclic ring system containing from one to two, the same or different, heteroatoms selected from the group consisting of nitrogen, oxygen and sulfur (or said 5- or 6-membered nonaromatic heterocyclic ring system substituted on any available carbon atom thereof by lower-alkyl, oxo, nitro, halogen, or lower-alkoxy, or on any available nitrogen atom thereof by lower-alkyl, trilower-alkylsilyl, trilower-alkylsilyl-lower-alkoxy-lower-alkyl, or phenyl-lower-alkyl (or said pheny-lower-alkyl group substituted on the phenyl group by lower-alkoxy, lower-alkyl or halogen));

or $R^2$ and $R^4$ and/or $R^3$ and $R^5$ taken together with the carbon atoms to which they are attached form a bicyclic ring system of the formula

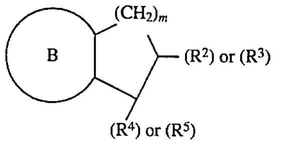

wherein B is:

phenyl, or a 5- or 6-membered monocyclic aromatic heterocyclic ring system containing from one to three, the same or different, heteroatoms selected from the group consisting of nitrogen, oxygen and sulfur, (or said B ring substituted on any available carbon atom thereof by lower-alkoxy, or lower-alkyl), and n is an integer from one to three;

$R^6$ is hydrogen, or from one to four, the same or different, substituents in any of the 7-, 8-, 9-, or 10-positions (if A is a six-membered ring), or in any of the 6-, 7-, 8-, or 9- position (if A is a five-membered ring) selected from the group consisting of lower-alkyl, lower-alkanoyloxy, halogen, nitro, hydroxy, lower-alkoxy, methylenedioxy, polychlorolower-alkyl, $OCO(CH_2)m$, C(O)O alkyl, OC(O)alkyl, C(O)Oalkyl, $CO_2^-$, carboxy, sulfo, $SO_3^-$, $PO_3H$, $PO_3^-$, cyano, and polyfluorolower-alkyl, wherein m is an integer from one to four;

A together with the carbon and nitrogen atoms to which it is attached forms a 5- or 6-membered monocyclic aromatic heterocycle containing from two to three, the same or different, heteroatoms selected from the group consisting of nitrogen, oxygen and sulfur (or said 5- or 6-membered monocyclic aromatic heterocycle substituted on any available carbon atom thereof by lower-alkyl, lower-alkoxy, or halogen; or on any available nitrogen atom thereof by lower-alkyl, or phenyl-lower-alkyl (or said phenyl-lower-alkyl group substituted on the phenyl group by lower-alkoxy, lower-alkyl or halogen));

$X^-$ is an anion; and p is zero when $R^6$ is a negatively charged radical, and p is one when $R^6$ is other than a negatively charged radical;

or a pharmaceutically acceptable acid-addition salt of basic members thereof; or a hydrate thereof; or a stereoisomer thereof.

3. A method according to claim 2 wherein $R^2$ and $R^3$ are independently hydrogen or lower-alkyl; and $R^6$ is hydrogen, or one lower-alkoxy substituent in any of the 7-,8-,9- or 10-positions (if A is a six-membered ring), or in any of the 6-,7-,8 or 9-positions (if A is a five-membered ring); and $R^1$ is hydrogen.

4. A method according to claim 2 wherein $R^4$ and $R^5$ are independently lower-alkoxy, phenyl (or phenyl substituted by lower-alkoxy, halogen, lower-alkyl, polyfluorolower-alkyl, polychlorolower-alkyl, or hydroxy), or a 5- or 6-membered monocyclic aromatic heterocyclic ring system containing from one to three, the same or different, heteroatoms selected from the group consisting of nitrogen, oxygen and sulfur (or said 5- or 6-membered monocyclic aromatic heterocyclic ring system substituted on any available carbon atom thereof by lower-alkyl, oxo, or lower-alkoxy; or on any available nitrogen atom thererof by lower-alkyl, or phenyl-lower-alkyl (or said phenyl-lower-alkyl group substituted on the phenyl group by lower-alkoxy, lower-alkyl or halogen).

5. A method according to claim 4 wherein:

R4 and R5 are independently lower-alkoxy, phenyl (or phenyl substituted by lower-alkoxy, halogen, lower-alkyl, polyfluorolower-alkyl, polychlorolower-alkyl, or hydroxy), or a 5-membered monocyclic aromatic heterocyclic ring system containing from one to three, the same or different, heteroatoms selected from the group consisting of nitrogen, oxygen, and sulfur (or said 5-membered monocyclic aromatic heterocyclic ring system substituted on any available carbon atom thereof by lower-alkyl, oxo, or lower-alkoxy; or on any available nitrogen atom thereof by lower-alkyl, or phenyl-lower-alkyl (or said phenyl-lower-alkyl group substituted on the phenyl group by lower-alkoxy, lower-alkyl or halogen); and A together with the carbon and nitrogen atoms to which it is attached froms a 5-membered monocyclic aromatic heterocycle containing from two-to three, the same or different, heteroatoms selected from the group consisting of nitrogen, oxygen and sulfur (or said 5-membered monocyclic aromatic heterocycle substituted on any available carbon atom thereof by lower-alkyl, lower-alkoxy, or halogen; or on any availabe nitrogen atom thereof by lower-alkyl, or phenyl-lower-alkyl (or said phenyl-lower-alkyl group substituted on the phenyl group by lower-alkoxy, lower alkyl or halogen).

6. A method according to claim 5 wherein $R^2$ and $R^3$ are independently hydrogen or lower-alkyl; and $R^6$ is hydrogen, or one substituent in any of the 6-,7-,8 or 9-positions selected from the group consisting of lower-alkyl, halogen, hydroxy, and lower-alkoxy.

7. A method according to claim 6 wherein:

$R^4$ and $R^5$ are independently lower-alkoxy, phenyl, or a 5-membered monocyclic aromatic heterocyclic ring system containing from one to two, the same or different, heteroatoms selected from the group consisting of nitrogen and oxygen (or said 5-membered monocyclic aromatic heterocyclic ring system substituted on any available carbon atom thereof by oxo, or on any available nitrogen atom thereof by phenyl-lower-alkyl (or said phenyl-lower-alkyl group substituted on the phenyl group by lower-alkoxy); and A together with the carbon and nitrogen atoms to which it it attached forms a 5-membered monocyclic aromatic heterocycle containing from two to three, the same or different, heteroatoms selected from the group consisting of nitrogen and sulfur (or said 5-membered monocyclic aromatic heterocycle substituted on any available carbon atom thereof by lower-alkyl; or on any available nitrogen atom thereof by lower-alkyl, or phenyl-lower-alkyl (or said phenyl-lower-alkyl group substituted on the phenyl group by lower alkoxy); $R^6$ is hydrogen, or one lower-alkoxy substituent in any of the 6-, 7-,8-, or 9-positions: and $R^1$ is hydrogen.

8. A method according to claim 7 wherein:

$R^4$ and $R^5$ are independently ethoxy, phenyl, or a 5-membered monocyclic aromatic heterocyclic ring system selected from furanyl, or pyrazolyl (or said 5-membered aromatic heterocyclic ring system substituted on any available carbon atom thereof by oxo, or on any available nitrogen atom thereof by methoxyphenylmethyl); and A together with the carbon and nitrogen atoms to which it is attached forms a 5-membered monocyclic aromatic heterocycle selected from thiazolyl, imidazolyl, or triazolyl (or said 5-membered monocyclic aromatic heterocycle substituted on any available carbon atom thereof by methyl; or on any available nitrogen atom thereof by methyl, phenylmethyl, or methoxyphenylmethyl; $R^2$ and $R^3$ are independently hydrogen or methyl, and $R^6$ is hydrogen, or 9-methoxy.

9. 11,11-Di(3-Furanyl)-5,10-ethano-5,10-dihydrothiazolo[3,2-b]isoquinolinium $X^-$ according to claim 8.

10. (+)-11,11-Di(3-furanyl)-5,10-ethano-5,10-dihydrothiazolo[3,2-b]isoquinolinium $X^-$ according to claim 9.

11. (+)-11,11-Di(3-furanyl)-5,10-ethano-5,10-dihydrothiazolo[3,2-b]isoquinolinium chloride according to claim 10.

12. A method according to claim 1 wherein $R^6$ is from one to four, the same or different, substituents in any of the 7-, 8-, 9-, or 10- positions (if A is a six-membered ring), or in any of the 6-, 7-, 8-, 9- positions (if A is a five-membered ring) selected from the group consisting of OC(O)alkyl-CH═CH-alkyl, OC(O)-lower-alkenyl-C(O)Oalkyl, alkoxy, OC(O)alkylC(O)Oalkyl, amino and lower-alkylsulfonylamino.

13. A method according to claim 1 wherein A together with the carbon and nitrogen atoms to which it is attacked forms a 5- or 6-membered monocyclic aromatic heterocycle containing from two to three, the same or different, heteroatoms selected from the group consisting of nitrogen, oxygen sulfur with said 5- or 6-membered monocyclic aromatic heterocycle being substituted on any available carbon atom thereof by hydroxy, OC(O)alkyl-CH═CH-alkyl, OC(O)alkyl, OC(O)-lower-alkenyl-C(O)Oalkyl, alkoxy, OC(O)alkylC(O)Oalkyl, nitro, amino or lower-alkylsulfonylamino; or on any available nitrogen atom thereof by phenyl (or said phenyl group substituted by lower-alkoxy, lower-alkyl or halogen), diphenylmethyl, naphthyl-lower-alkyl (or said naphthyl-lower-alkyl group substituted on the naphthyl group by lower-alkoxy, lower-alkyl or halogen).

14. A method according to claim 13 wherein:

$R^4$ and $R^5$ are independently a 5-membered monocyclic aromatic heterocyclic ring system selected from the group consisting of furanyl, thienyl, oxazolyl, thiazolyl, pyrazolyl, triazolyl, pyrrolyl, imidazolyl, isoxazolyl, oxadiazolyl, and thiadiazolyl;

$R^6$ is hydrogen, or one substituent in any of the 6-, 7-, 8-, 9-positions selected from the group consisting of lower-alkoxy and hydroxy;

A together with the carbon and nitrogen atoms to which it is attached forms a 5-membered monocyclic aromatic heterocycle selected from the group consisting of imidazolyl and triazolyl, with said 5-membered monocyclic aromatic heterocycle being substituted on any available nitrogen atom thereof by phenyl, diphenylmethyl, or naphthyl-lower-alkyl; and $X^-$ is an anion.

15. A method according to claim 14 wherein:

$R^1$, $R^2$, $R^3$ and $R^6$ are hydrogen;

$R^4$ and $R^5$ are furanyl;

A together with the carbon and nitrogen atoms to which it is attached forms an imidazole ring which is substituted on the available nitrogen atom thereof by phenyl, diphenylmethyl, or naphthylmethyl; and $X^-$ is an anion.

16. A method according to claim 1 for the treatment or prevention of neurotoxic injuries.

17. A method according to claim 1 wherein said neurotoxic injuries are associated with ischemic, hypoxic, or hypoglycemic conditions.

18. A method according to claim 17 wherein said ischemic, hypoxic, or hypoglycemic conditions are associated with stroke.

19. A method according to claim 8 for the treatment or prevention of neurotoxic injuries which comprises administering to a patient in need of such treatment an effective amount of the compound 11,11-di(3-furanyl)-5,10-ethano-5,10-dihydrothiazolo[3,2-b]isoquinolinium $X^-$.

20. A method according to claim 19 wherein the compound is (+)-11,11-di(3-furanyl)-5,10-ethano-5,10-dihydrothiazolo[3,2-b]isoquinolinium $X^-$.

21. A method according to claim 20 wherein X is chloride.

* * * * *